(12) United States Patent
Le Tiran et al.

(10) Patent No.: US 9,944,620 B2
(45) Date of Patent: *Apr. 17, 2018

(54) INDOLIZINE COMPOUNDS, A PROCESS FOR THEIR PREPARATION AND PHARMACEUTICAL COMPOSITIONS CONTAINING THEM

(71) Applicants: LES LABORATOIRES SERVIER, Suresnes (FR); VERNALIS (R&D) LTD, Winnersh (GB)

(72) Inventors: Arnaud Le Tiran, Croissy sur Seine (FR); Thierry Le Diguarher, Sanit Denis de l'Hôtel (FR); Jérôme-Benoît Starck, Rueil-Malmaison (FR); Jean-Michel Henlin, Suresnes (FR); Guillaume De Nanteuil, Suresnes (FR); Olivier Geneste, Rueil-Malmaison (FR); James Edward Paul Davidson, Great Shelford (GB); James Brooke Murray, Linton (GB); I-Jen Chen, Cambridge (GB)

(73) Assignees: LES LABORATOIRES SERVIER, Suresnes (FR); VERNALIS (R&D) LTD, Winnersh Berkshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/906,330

(22) PCT Filed: Jul. 22, 2014

(86) PCT No.: PCT/FR2014/051885
§ 371 (c)(1),
(2) Date: Jan. 20, 2016

(87) PCT Pub. No.: WO2015/011397
PCT Pub. Date: Jan. 29, 2015

(65) Prior Publication Data
US 2016/0176848 A1    Jun. 23, 2016

(30) Foreign Application Priority Data
Jul. 23, 2013  (FR) ...................................... 13 57265

(51) Int. Cl.
| | |
|---|---|
| *C07D 401/14* | (2006.01) |
| *C07D 471/04* | (2006.01) |
| *A61K 31/4985* | (2006.01) |
| *C07D 487/04* | (2006.01) |
| *C07D 519/00* | (2006.01) |
| *A61K 45/06* | (2006.01) |
| *A61K 31/4725* | (2006.01) |
(Continued)

(52) U.S. Cl.
CPC .......... *C07D 401/14* (2013.01); *A61K 9/2018* (2013.01); *A61K 9/2054* (2013.01); *A61K 9/2059* (2013.01); *A61K 31/475* (2013.01); *A61K 31/4709* (2013.01); *A61K 31/4725* (2013.01); *A61K 31/4985* (2013.01); *A61K 31/5377* (2013.01); *A61K 45/06* (2013.01); *A61N 5/10* (2013.01); *C07D 471/04* (2013.01); *C07D 487/04* (2013.01); *C07D 519/00* (2013.01)

(58) Field of Classification Search
None
See application file for complete search history.

(56) References Cited

U.S. PATENT DOCUMENTS

| | | |
|---|---|---|
| 7,713,994 B2 | 5/2010 | Tsou et al. |
| 7,902,218 B2 | 3/2011 | Thompson, III et al. |
| (Continued) | | |

FOREIGN PATENT DOCUMENTS

| | | |
|---|---|---|
| RU | 2468010 | 11/2012 |
| WO | WO 2003/093297 | 11/2003 |
| (Continued) | | |

OTHER PUBLICATIONS

Porter, J. et al. Tetrahydroisoquinoline amide substituted phenyl pyrazoles as selective Bcl-2 inhibitors. Bioorganic & Medicinal Chemistry Letters. 2009, vol. 19, p. 232.*

(Continued)

*Primary Examiner* — Niloofar Rahmani
(74) *Attorney, Agent, or Firm* — Hueschen and Sage

(57) ABSTRACT

Compounds of formula (I) wherein Ra, Rb, Rc, Rd, T, R3, R4, R5, X, Y and Het are as defined in the description.

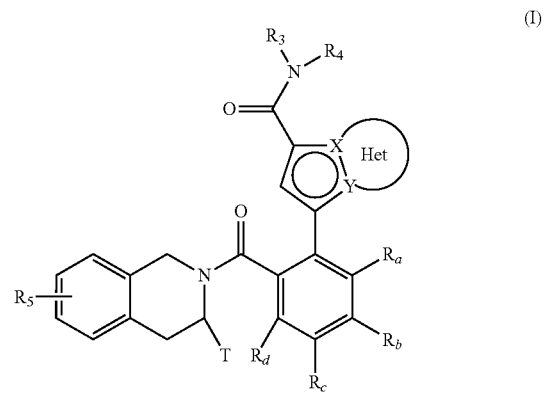

Medicinal products containing the same which are useful in treating pathologies involving a deficit in apoptosis, such as cancer, auto-immune diseases, and diseases of the immune system.

5 Claims, No Drawings

(51) Int. Cl.
  *A61K 31/475*    (2006.01)
  *A61K 31/5377*   (2006.01)
  *A61K 9/20*      (2006.01)
  *A61K 31/4709*   (2006.01)
  *A61N 5/10*      (2006.01)

(56) References Cited

U.S. PATENT DOCUMENTS

| | | |
|---|---|---|
| 8,263,607 B2 | 9/2012 | Shishikura et al. |
| 9,115,159 B2 * | 8/2015 | Le Tiran .................... C07F 9/09 |
| 9,120,791 B2 * | 9/2015 | Le Diguarher ...... C07D 471/00 |
| 2005/0070570 A1 | 3/2005 | Garcia et al. |
| 2017/0143746 A1 | 5/2017 | Le Tiran et al. |
| 2017/0151251 A1 | 6/2017 | Le Diguarher et al. |

FOREIGN PATENT DOCUMENTS

| | | |
|---|---|---|
| WO | WO 2006/023778 | 3/2006 |
| WO | WO 2008/131000 | 10/2008 |
| WO | WO 2009/073545 | 6/2009 |
| WO | WO 2009/102488 | 8/2009 |
| WO | WO 2012/162365 | 11/2012 |
| WO | WO 2013/096051 | 6/2013 |
| WO | WO 2013/096055 | 6/2013 |
| WO | WO 2013/096059 | 6/2013 |
| WO | WO 2013/096060 | 6/2013 |
| WO | WO 2013/098049 | 6/2013 |
| WO | WO 2013/110890 | 8/2013 |

OTHER PUBLICATIONS

Nakamura, I. et al. Transition-Metal-Catalyzed Reactions in Heterocyclic Synthesis. Chem. Rev. 2004, vol. 104, p. 2127.*
International Serach Report for PCT/FR2014/051885 dated Sep. 26, 2014.
Bundgaard, H., Textbook of Drug Design and Development, 1991, 113-191.
Deng, et al., Cancer Cell, 2007, 12, 171-185.
Hanada, et al., Blood, 1993, 82, 1820-1828.
Hockenbery, et al., Proc. Natl. Acad. Sci. USA, 1991, 88, 6961-6965.
Juin, et al., Nature Reviews Cancer, 2013, 13, 455-465.
Kelly, et al., Cell Death and Differentiation, 2011, 18, 1414-1424.
Kirkin, et al., Biochimica et Biophysica Acta, 2004, 1644, 229-249.
Letai, et al., Blood, 2005, 106, 5008.
Monni, et al., Blood, 1997, 90, 1168-1174.
Perez, et al., Bioorganic & Medicinal Chemistry Letters, 2012, 22, 3946-3950.
Porter, et al., Bioorganic & Medicinal Chemistry Letters, 2009, 19, 1767-1772.
Schroeder, et al., Bioorganic & Medicinal Chemistry Letters, 2012, 22, 3951-3956.
Slavov, et al., Proc. Natl. Acad. Sci. USA, 2009, 106, 4079-4084.
Tsujimoto, et al., Science, 1985, 228, 1440-1443.
Vaux, et al., Nature, 1988, 335, 440-442.
Yip, et al., Oncogene, 2008, 27, 6398-6406.

* cited by examiner

INDOLIZINE COMPOUNDS, A PROCESS FOR THEIR PREPARATION AND PHARMACEUTICAL COMPOSITIONS CONTAINING THEM

The present invention relates to new indolizine compounds, to a process for their preparation and to pharmaceutical compositions containing them.

The compounds of the present invention are new and have very valuable pharmacological characteristics in the field of apoptosis and cancerology.

Apoptosis, or programmed cell death, is a physiological process that is crucial for embryonic development and maintenance of tissue homeostasis.

Apoptotic-type cell death involves morphological changes such as condensation of the nucleus, DNA fragmentation and also biochemical phenomena such as the activation of caspases which cause damage to key structural components of the cell, so inducing its disassembly and death. Regulation of the process of apoptosis is complex and involves the activation or repression of several intracellular signalling pathways (Cory S. et al., Nature Review Cancer, 2002, 2, 647-656).

Deregulation of apoptosis is involved in certain pathologies. Increased apoptosis is associated with neurodegenerative diseases such as Parkinson's disease, Alzheimer's disease and ischaemia. Conversely, deficits in the implementation of apoptosis play a significant role in the development of cancers and their chemoresistance, in autoimmune diseases, inflammatory diseases and viral infections. Accordingly, absence of apoptosis is one of the phenotypic signatures of cancer (Hanahan D. et al., Cell 2000, 100, 57-70).

The anti-apoptotic proteins of the Bcl-2 family are associated with numerous pathologies. The involvement of proteins of the Bcl-2 family is described in numerous types of cancer, such as colorectal cancer, breast cancer, small-cell lung cancer, non-small-cell lung cancer, bladder cancer, ovarian cancer, prostate cancer, chronic lymphoid leukaemia, follicular lymphoma, myeloma, prostate cancer, etc. Overexpression of the anti-apoptotic proteins of the Bcl-2 family is involved in tumorigenesis, in resistance to chemotherapy and in the clinical prognosis of patients affected by cancer. There is, therefore, a therapeutic need for compounds that inhibit the anti-apoptotic activity of the proteins of the Bcl-2 family.

In addition to being new, the compounds of the present invention have pro-apoptotic properties making it possible to use them in pathologies involving a defect in apoptosis, such as, for example, in the treatment of cancer, autoimmune diseases and diseases of the immune system.

The present invention relates more especially to compounds of formula (I):

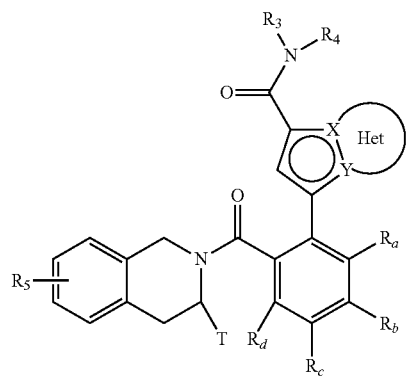

wherein:
X and Y represent a carbon atom or a nitrogen atom, it being understood that they may not simultaneously represent two carbons atoms or two nitrogen atoms, the Het moiety of the group

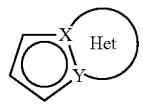

represents an optionally substituted, aromatic or non-aromatic ring composed of 5, 6 or 7 ring members, which may contain, in addition to the nitrogen represented by X or by Y, from one to 3 hetero atoms selected independently from oxygen, sulphur and nitrogen, it being understood that the nitrogen in question may be substituted by a group representing a hydrogen atom, a linear or branched $(C_1-C_6)$alkyl group or a group —C(O)—O-Alk wherein Alk is a linear or branched $(C_1-C_6)$alkyl group, T represents a hydrogen atom, a linear or branched $(C_1-C_6)$alkyl group optionally substituted by from one to three halogen atoms, a group $(C_2-C_4)$alkyl-$NR_1R_2$, or a group $(C_1-C_4)$alkyl-$OR_6$, $R_1$ and $R_2$ independently of one another represent a hydrogen atom or a linear or branched $(C_1-C_6)$alkyl group, or $R_1$ and $R_2$ form with the nitrogen atom carrying them a heterocycloalkyl, $R_3$ represents a linear or branched $(C_1-C_6)$alkyl group, a linear or branched $(C_2-C_6)$alkenyl group, a linear or branched $(C_2-C_6)$alkynyl group, a cycloalkyl group, a $(C_3-C_{10})$cycloalkyl-$(C_1-C_6)$alkyl group wherein the alkyl moiety is linear or branched, a heterocycloalkyl group, an aryl group or a heteroaryl group, it being understood that one or more of the carbon atoms of the preceding groups, or of their possible substituents, may be deuterated, $R_4$ represents an aryl group, a heteroaryl group, a cycloalkyl group or a linear or branched $(C_1-C_6)$alkyl group, it being understood that one or more of the carbon atoms of the preceding groups, or of their possible substituents, may be deuterated, $R_5$ represents a hydrogen or halogen atom, a linear or branched $(C_1-C_6)$alkyl group, or a linear or branched $(C_1-C_6)$alkoxy group, $R_6$ represents a hydrogen atom or a linear or branched $(C_1-C_6)$alkyl group, $R_a$, $R_b$, $R_c$ and $R_d$, each independently of the others, represent $R_7$, a halogen atom, a linear or branched $(C_1-C_6)$alkoxy group, a hydroxy group, a linear or branched $(C_1-C_6)$polyhaloalkyl group, a trifluoromethoxy group, —$NR_7R_7'$, nitro, $R_7$—CO—$(C_0-C_6)$alkyl-, $R_7$—CO—NH—$(C_0-C_6)$alkyl-, $NR_7R_7'$—CO—$(C_0-C_6)$alkyl-, $NR_7R_7'$—CO—$(C_0-C_6)$alkyl-O—, $R_7$—$SO_2$—NH—$(C_0-C_6)$alkyl-, $R_7$—NH—CO—NH—$(C_0-C_6)$alkyl-, $R_7$—O—CO—NH—$(C_0-C_6)$alkyl-, a heterocycloalkyl group, or the substituents of one of the pairs $(R_a,R_b)$, $(R_b,R_c)$ or $(R_c,R_d)$ form together with the carbon atoms carrying them a ring composed of from 5 to 7 ring members, which may contain from one to 2 hetero atoms selected from oxygen and sulphur, it also being understood that one or more carbon atoms of the ring defined hereinbefore may be deuterated or substituted by from one to 3 groups selected from halogen and linear or branched ($C_1$-$C_6$)alkyl, $R_7$ and $R_7'$, each independently of the other, represent a hydrogen, a linear or branched ($C_1$-$C_6$)alkyl, a linear or branched ($C_2$-$C_6$)alkenyl, a linear or branched ($C_2$-$C_6$)alkynyl, an aryl or a heteroaryl, or $R_7$ and $R_7'$, together with the nitrogen atom carrying them, form a heterocycle composed of from 5 to 7 ring members, it being understood that:
"aryl" means a phenyl, naphthyl, biphenyl or indenyl group,
"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens),
"cycloalkyl" means any mono- or bi-cyclic, non-aromatic, carbocyclic group containing from 3 to 10 ring members,
"heterocycloalkyl" means any mono- or bi-cyclic, non-aromatic, condensed or spiro group containing from 3 to 10 ring members and containing from 1 to 3 hetero atoms selected from oxygen, sulphur, SO, $SO_2$ and nitrogen, it being possible for the aryl, heteroaryl, cycloalkyl and heterocycloalkyl groups so defined and the groups alkyl, alkenyl, alkynyl and alkoxy to be substituted by from 1 to 3 groups selected from optionally substituted, linear or branched ($C_1$-$C_6$)alkyl, ($C_3$-$C_6$)spiro, optionally substituted, linear or branched ($C_1$-$C_6$)alkoxy, ($C_1$-$C_6$)alkyl-S—, hydroxy, oxo (or N-oxide where appropriate), nitro, cyano, —COOR', —OCOR', NR'R", linear or branched ($C_1$-$C_6$) polyhaloalkyl, trifluoromethoxy, ($C_1$-$C_6$)alkylsulphonyl, halogen, optionally substituted aryl, heteroaryl, aryloxy, arylthio, cycloalkyl, heterocycloalkyl optionally substituted by one or more halogen atoms or alkyl groups, it being understood that R' and R", each independently of the other, represent a hydrogen atom or an optionally substituted, linear or branched ($C_1$-$C_6$)alkyl group, it being possible for the Het moiety of the group

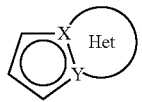

Het defined in formula (I) to be substituted by from one to three groups selected from linear or branched ($C_1$-$C_6$)alkyl, hydroxy, linear or branched ($C_1$-$C_6$)alkoxy, $NR_1'R_1''$ and halogen, it being understood that $R_1'$ and $R_1''$ are as defined for the groups R' and R" mentioned hereinbefore, to their enantiomers and diastereoisomers, and to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Advantageously, the group:

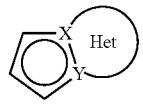

represents one of the following groups: 5,6,7,8-tetrahydroindolizine optionally substituted by an amino group; indolizine; 1,2,3,4-tetrahydropyrrolo[1,2-a]pyrazine optionally substituted by a methyl; pyrrolo[1,2-a]pyrimidine. The groups 5,6,7,8-tetrahydroindolizine and indolizine are more especially preferred.

In preferred compounds of the invention, T represents a hydrogen atom, a methyl group (and more especially an (R)-methyl), a group 2-(morpholin-4-yl)ethyl, 3-(morpholin-4-yl)propyl, —$CH_2$—OH, 2-aminoethyl, 2-(3,3-difluoropiperidin-1-yl)ethyl, 2-[(2,2-difluoroethyl)amino]ethyl or 2-(3-methoxyazetidin-1-yl)ethyl.

Preferably, $R_a$ and $R_d$ each represent a hydrogen atom and ($R_b$,$R_c$), together with the carbon atoms carrying them, form a 1,3-dioxolane group or a 1,4-dioxane group; or $R_a$, $R_c$ and $R_d$ each represent a hydrogen atom and $R_b$ represents a hydrogen, a halogen, a methyl or a methoxy; or $R_a$, $R_b$ and $R_d$ each represent a hydrogen atom and $R_c$ represents a hydroxy or methoxy group. Even more preferably, $R_a$ and $R_d$ each represent a hydrogen atom and ($R_b$,$R_c$), together with the carbon atoms carrying them, form a 1,3-dioxolane group; or $R_a$, $R_c$ and $R_d$ each represent a hydrogen atom and $R_b$ represents a halogen. Preference is given to the $R_4$ group being a 4-hydroxyphenyl.

In preferred compounds of the invention, $R_3$ represents a linear ($C_1$-$C_6$)alkyl, aryl or heteroaryl group, it being possible for the latter two groups to be substituted by from one to three groups selected from halogen, linear or branched ($C_1$-$C_6$)alkyl, linear or branched ($C_1$-$C_6$)alkoxy, cyano and heterocycloalkyl-($C_1$-$C_6$)alkyl wherein the alkyl moiety is linear or branched. Even more preferably, $R_3$ represents a heteroaryl group selected from the following group: 1H-indole, 2,3-dihydro-1H-indole, 1H-indazole, pyridine, 1H-pyrrolo[2,3-b]pyridine, 1H-pyrazole, imidazo[1,2-a] pyridine, pyrazolo[1,5-a]pyrimidine, [1,2,4]triazolo[1,5-a] pyrimidine, and 1H-pyrazolo[3,4-b]pyridine, all of which may be substituted by a linear or branched ($C_1$-$C_6$)alkyl group.

Preferred compounds according to the invention are included in the following group:
N-(4-hydroxyphenyl)-3-(6-{[(3R)-3-methyl-3,4-dihydroisoquinolin-2(1H)-yl]carbonyl}-1,3-benzodioxol-5-yl)-N-{1-[2-(morpholin-4-yl)ethyl]-1H-indol-5-yl}-5,6,7,8-tetrahydroindolizine-1-carboxamide,
N-(4-hydroxyphenyl)-3-(6-{[(3S)-3-[2-(morpholin-4-yl) ethyl]-3,4-dihydroisoquinolin-2(1H)-yl]carbonyl}-1,3-benzodioxol-5-yl)-N-phenyl-5,6,7,8-tetrahydroindolizine-1-carboxamide,
N-{3-fluoro-4-[2-(morpholin-4-yl)ethoxy]phenyl}-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide,
N-(4-hydroxyphenyl)-3-(6-{[(3R)-3-methyl-3,4-dihydroisoquinolin-2(1H)-yl]carbonyl}-1,3-benzodioxol-5-yl)-N-(pyridin-4-yl)indolizine-1-carboxamide,
N-(4-hydroxyphenyl)-3-(6-{[(3R)-3-methyl-3,4-dihydroisoquinolin-2(1H)-yl]carbonyl}-1,3-benzodioxol-5-yl)-N-(2-methylpyridin-4-yl)indolizine-1-carboxamide, N-(4-hydroxyphenyl)-3-(6-{[(3R)-3-methyl-3,4-dihydroisoquinolin-2(1H)-yl]carbonyl}-1,3-benzodioxol-5-yl)-N-(1-methyl-1H-pyrrolo[2,3-b]pyridin-5-yl)indolizine-1-carboxamide, N-(4-hydroxyphenyl)-3-(6-{[(3R)-3-[3-(morpholin-4-yl)propyl]-3,4-dihydroisoquinolin-2(1H)-yl]carbonyl}-1,3-benzodioxol-5-yl)-N-phenyl-5,6,7,8-tetrahydroindolizine-1-carboxamide, N-(2,6-dimethylpyridin-4-yl)-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide, N-(4-hydroxyphenyl)-3-(6-{[(3R)-3-methyl-3,4-dihydroisoquinolin-2(1H)-yl]carbonyl}-1,3-benzodioxol-5-yl)-N-(pyridin-4-yl)-5,6,7,8-tetrahydroindolizine-1-carboxamide, 3-(5-chloro-2-{[(3R)-3-methyl-3,4-dihydroisoquinolin-2(1H)-yl]carbonyl}phenyl)-N-(4-hydroxyphenyl)-N-(1-methyl-1H-pyrrolo[2,3-b]pyridin-5-yl)indolizine-1-carboxamide, N-(4-hydroxyphenyl)-N-(2-methoxypyridin-4-yl)-3-(6-{[(3R)-3-methyl-3,4-dihydroisoquinolin-2(1H)-yl]carbonyl}-1,3-benzodioxol-5-yl)indolizine-1-carboxamide, their enantiomers and diastereoisomers, and addition salts thereof with a pharmaceutically acceptable acid or base.

The invention relates also to a process for the preparation of compounds of formula (I), which process is characterised in that there is used as starting material the compound of formula (II):

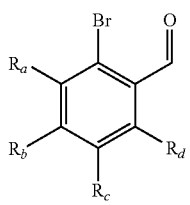

(II)

wherein $R_a$, $R_b$, $R_c$ and $R_d$ are as defined for formula (I), which compound of formula (II) is subjected to a Heck reaction, in an aqueous or organic medium, in the presence of a palladium catalyst, of a base, of a phosphine and of the compound of formula (III):

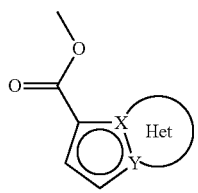

(III)

wherein the groups X, Y and Het are as defined for formula (I), to obtain the compound of formula (IV):

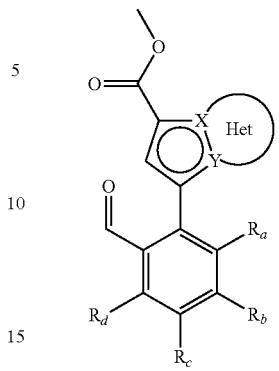

(IV)

wherein $R_a$, $R_b$, $R_c$, $R_d$, X, Y and Het are as defined for formula (I), the aldehyde function of which compound of formula (IV) is oxidised to a carboxylic acid to form the compound of formula (V):

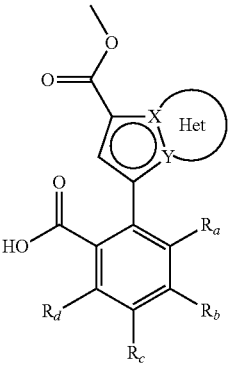

(V)

wherein $R_a$, $R_b$, $R_c$, $R_d$, X, Y and Het are as defined for formula (I), which compound of formula (V) is then subjected to peptide coupling with a compound of formula (VI):

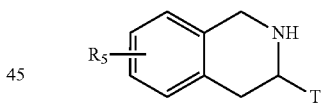

(VI)

wherein T and $R_5$ are as defined for formula (I),
to yield the compound of formula (VII):

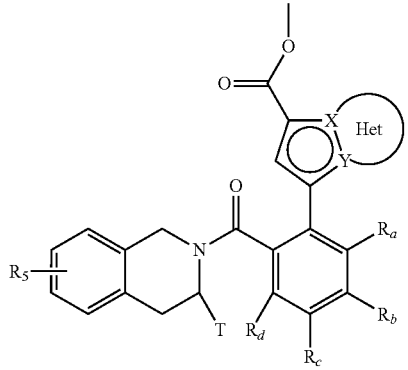

(VII)

wherein $R_a$, $R_b$, $R_c$, $R_d$, T, $R_5$, X, Y and Het are as defined for formula (I),
the ester function of which compound of formula (VII) is hydrolysed to yield the corresponding carboxylic acid or carboxylate, which may be converted into an acid derivative such as the corresponding acyl chloride or anhydride before being coupled with an amine $NHR_3R_4$ wherein $R_3$ and $R_4$ have the same meanings as for formula (I), to yield the compound of formula (I),
which compound of formula (I) may be purified according to a conventional separation technique, which is converted, if desired, into its addition salts with a pharmaceutically acceptable acid or base and which is optionally separated into its isomers according to a conventional separation technique,
it being understood that, at any time considered appropriate in the course of the above-described process, certain groups (hydroxy, amino . . . ) of the reagents or intermediates of synthesis may be protected and then deprotected according to the requirements of synthesis.

More particularly, when one of the groups $R_3$ or $R_4$ of the amine $NHR_3R_4$ is substituted by a hydroxy function, the latter may be subjected beforehand to a protection reaction prior to any coupling with the carboxylic acid formed from the compound of formula (VII), or with a corresponding acid derivative thereof, the resulting protected compound of formula (I) subsequently undergoes a deprotection reaction and is then optionally converted into one of its addition salts with a pharmaceutically acceptable acid or base.

The compounds of formulae (II), (III), (VI) and the amine $NHR_3R_4$ are either commercially available or can be obtained by the person skilled in the art using conventional chemical reactions described in the literature.

Pharmacological study of the compounds of the invention has shown that they have pro-apoptotic properties. The ability to reactivate the apoptotic process in cancerous cells is of major therapeutic interest in the treatment of cancers, auto-immune diseases and diseases of the immune system.

More especially, the compounds according to the invention will be useful in the treatment of chemo- or radio-resistant cancers, and in malignant haemopathies and small-cell lung cancer.

Among the cancer treatments envisaged there may be mentioned, without implying any limitation, cancers of the bladder, brain, breast and uterus, chronic lymphoid leukaemias, colorectal cancer, cancers of the œsophagus and liver, lymphoblastic leukaemias, non-Hodgkin lymphomas, melanomas, malignant haemopathies, myelomas, ovarian cancer, non-small-cell lung cancer, prostate cancer and small-cell lung cancer. Among non-Hodgkin lymphomas, there may be mentioned more preferably follicular lymphomas, mantle cell lymphomas, diffuse large B-cell lymphomas, small lymphocytic lymphomas and marginal zone B-cell lymphomas.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragées, sublingual tablets, sachets, paquets, capsules, glossettes, lozenges, suppositories, creams, ointments, dermal gels, and drinkable or injectable ampoules.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the association of a compound of formula (I) with an anticancer agent selected from genotoxic agents, mitotic poisons, antimetabolites, proteasome inhibitors, kinase inhibitors and antibodies, and also to pharmaceutical compositions comprising that type of association and their use in the manufacture of medicaments for use in the treatment of cancer.

The compounds of the invention may also be used in association with radiotherapy in the treatment of cancer.

Finally, the compounds of the invention may be linked to monoclonal antibodies or fragments thereof or linked to scaffold proteins that can be related or not to monoclonal antibodies.

Antibody fragments must be understood as fragments of Fv, scFv, Fab, F(ab')2, F(ab'), scFv-Fc type or diabodies, which generally have the same specificity of binding as the antibody from which they are descended. According to the present invention, antibody fragments of the invention can be obtained starting from antibodies by methods such as digestion by enzymes, such as pepsin or papain, and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers such as those supplied by the company Applied Biosystems, etc.

Scaffold proteins that can be related or not to monoclonal antibodies are understood to mean a protein that contains or not an immunoglobulin fold and that yields a binding capacity similar to a monoclonal antibody. The man skilled in the art knows how to select the protein scaffold. More particularly, it is known that, to be selected, such a scaffold should display several features as follow (Skerra A., J. Mol. Recogn., 13, 2000, 167-187): phylogenetically good conservation, robust architecture with a well-known three-dimensional molecular organization (such as, for example, crystallography or NMR), small size, no or only a low degree of post-translational modifications, easy to produce, express and purify. Such a protein scaffold can be, but without limitation, a structure selected from the group consisting in fibronectin and preferentially the tenth fibronectin type III domain (FNfn10), lipocalin, anticalin (Skerra A., J. Biotechnol., 2001, 74(4):257-75), the protein Z derivative from the domain B of staphylococcal protein A, thioredoxin A or any protein with a repeated domain such as an "ankyrin repeat" (Kohl et al., PNAS, 2003, vol. 100, No. 4, 1700-1705), "armadillo repeat", "leucine-rich repeat" or "tetratricopeptide repeat".

There could also be mentioned a scaffold derivative from toxins (such as, for example, scorpion, insect, plant or mollusc toxins) or protein inhibitors of neuronal nitric oxide synthase (PIN).

The following Preparations and Examples illustrate the invention without limiting it in any way.

General Procedures

All reagents and anhydrous solvents are obtained from commercial sources and were used without further purification or drying. Flash chromatography is performed on an ISCO CombiFlash Rf 200i apparatus with pre-packed silica-gel cartridges (SiliaSep™ F60 (40-63 m, 60 Å). Thin layer chromatography was conducted with 5×10 cm plates coated with Merck Type 60 $F_{254}$ silica gel. Microwave heating was performed with a CEM Discover® SP apparatus.

Analytical LC-MS

The compounds of the invention were characterized by high-performance liquid chromatography coupled with mass spectroscopy (HPLC-MS) on either an Agilent HP1200 rapid-resolution apparatus coupled to a 6140 mass detector with a multi-mode source (m/z range 150 to 1000 atomic mass units or amu) or an Agilent HP1100 apparatus coupled to a 1946D mass detector with an electrospray ionisation source (m/z range 150 to 1000 amu). The conditions and methods listed below are identical for both machines.

Detection: UV detection at 230, 254 and 270 nm.
Injection Volume: 2 μL
Mobile Phases: A—Water+10 mMol/ammonium formate+ 0.08% (v/v) formic acid at pH ca 3.5.
B—95% Acetonitrile+5% A+0.08% (v/v) formic acid
Method A (3.75 min; either positive (pos) or positive and negative (pos/neg) ionisation)
Column: Gemini 5 m, C18, 30 mm×4.6 mm (Phenomenex).
Temperature: 35° C.
Gradient:

| Time (min) | Solvent A (%) | Solvent B (%) | Flow (mL/min) |
|---|---|---|---|
| 0 | 95 | 5 | 2 |
| 0.25 | 95 | 5 | 2 |
| 2.50 | 95 | 5 | 2 |
| 2.55 | 5 | 95 | 3 |
| 3.60 | 5 | 95 | 3 |
| 3.65 | 5 | 95 | 2 |
| 3.70 | 95 | 5 | 2 |
| 3.75 | 95 | 5 | 2 |

Method B (1.9 min; either positive (pos) or positive and negative (pos/neg) ionisation)
Column: Gemini 5 μm, C18, 30 mm×4.6 mm (Phenomenex).
Temperature: 35° C.
Gradient:

| Time (min) | Solvent A (%) | Solvent B (%) | Flow (mL/min) |
|---|---|---|---|
| 0 | 95 | 5 | 1.1 |
| 0.12 | 95 | 5 | 1.1 |
| 1.30 | 5 | 95 | 1.1 |
| 1.35 | 5 | 95 | 1.7 |
| 1.85 | 5 | 95 | 1.7 |
| 1.90 | 5 | 95 | 1.1 |
| 1.95 | 95 | 5 | 1.1 |

Preparation 1: 6-[1-(Methoxycarbonyl)-5,6,7,8-tetrahydro-3-indolizinyl]-1,3-benzodioxole-5-carboxylic acid Step A: 1-Formyl-2-piperidine-carboxylic acid To a solution of 40 g of a racemic mixture of 2-piperidine-carboxylic acid (0.310 mmol) in 300 mL of formic acid placed at 0° C. there are added, dropwise, 200 mL (2.15 mmol) of acetic anhydride. The batch is then stirred at ambient temperature overnight. Then, the reaction mixture is cooled to 0° C., hydrolysed by adding 250 mL of water, and stirred for half an hour at 0° C. before being concentrated to dryness. The oil thereby obtained is taken up in 200 mL of methanol and then concentrated to dryness. The title product is obtained in the form of an oil in a yield of 98%. It is used directly, without being otherwise purified, in the next Step.

$^1$H NMR: δ (400 MHz; dmso-d6; 300K): 13.0 (m, 1H OH); 8.0-8.05 (2s, 1H aldehyde); 4.9-4.5 (2d, 1H α to the N and COOH); 4.1-2.6 (m, 2H α to the N); 2.2-1.2 (m, 6H piperidine)

IR: ν: —OH: 2000-3000 cm$^{-1}$ acid; ν: >C═O 1703 cm$^{-1}$ wide band

Step B: Methyl 5,6,7,8-tetrahydro-1-indolizine-carboxylate

To a solution of 10 g of the carboxylic acid obtained in Step A (63.6 mmol) in 65 mL of dichloromethane there are successively added 13.4 g of tosyl chloride (70.4 mmol), 11.5 mL of methyl 2-chloroacrylate (113.5 mmol) and then, dropwise, 17.8 mL of N,N,N-triethylamine (127.2 mmol). The reaction mixture is then refluxed for 1 hour 30 minutes. It is then placed at ambient temperature, and there are then added 5 mL of methyl 2-chloroacrylate (48.9 mmol) and, dropwise, 9 mL of N,N,N-triethylamine (64 mmol). The batch is refluxed overnight.

The reaction mixture is then diluted with methylene chloride, washed successively with 1N HCl solution, saturated NaHCO$_3$ solution and then saturated NaCl solution until a neutral pH is obtained. The organic phase is then dried over MgSO$_4$, filtered, concentrated to dryness and purified by chromatography over silica gel (heptane/AcOEt gradient). The title product is obtained in the form of an oil.

$^1$H NMR: δ (400 MHz; CDCl$_3$; 300K): 6.55-6.40 (d, 2H, tetrahydroindolizine); 3.91 (t, 3H methyl ester); 3.78 (s, 3H tetrahydroindolizine); 3.08 (t, 2H, tetrahydroindolizine); 1.95-1.85 (m, 4H, tetrahydroindolizine)

IR: ν:>C═O 1692 cm$^{-1}$ ester

Step C: Methyl 3-(6-formyl-1,3-benzodioxol-5-yl)-5,6,7,8-tetrahydro-1-indolizine-carboxylate To a solution of 6.4 g of the ester obtained in Step B (35.7 mmol) in 12 mL of N,N-dimethylacetamide, there are successively added 12.3 g of 6-bromo-1,3-benzodioxole-5-carbaldehyde (53.6 mmol) and 7 g of potassium acetate (71.4 mmol), and then the batch is stirred under argon for 20 minutes. There are then added 1.3 g of palladium catalyst PdCl$_2$(PPh$_3$)$_2$(1.8 mmol). The reaction mixture is then heated at 130° C. for one hour before adding 139 μL of H$_2$O thereto. Heating is maintained at that same temperature overnight. The mixture is allowed to return to ambient temperature and it is then diluted with AcOEt. Animal charcoal (2 g per g of product) is added and the batch is stirred at ambient temperature for 1 hour and then filtered. The organic phase is then washed with water, dried over magnesium sulphate and concentrated to dryness. The crude product thereby obtained is purified over silica gel (heptane/ACOEt gradient). The title product is obtained in the form of an oil.

$^1$H NMR: δ:(400 MHz; dmso-d6; 353° K): 9.65 (s, 1H, H aldehyde); 7.3-7.15 (2s, 2H, aromatic Hs); 6.45 (s, 1H tetrahydroindolizine); 6.20 (s, 2H methylenedioxy); 3.70 (s, 3H methyl ester); 3.5-4.0 (m, 2H tetrahydroindolizine); 3.05 (m, 2H tetrahydroindolizine); 1.85 (m, 4H tetrahydroindolizine)

IR: ν: >C═O 1695 cm$^{-1}$ ester; ν: >C═O 1674 cm$^{-1}$

Step D: 6-[1-(Methoxycarbonyl)-5,6,7,8-tetrahydro-3-indolizinyl]-1,3-benzodioxole-5-carboxylic acid A solution containing 3.37 g of the compound obtained in Step C (10.3 mmol) in 9.3 mL of acetone and 8.8 mL (80.24 mmol) of 2-methyl-2-butene is prepared and placed at 0° C. There are added, dropwise, 9.3 mL of an aqueous solution containing a mixture of 3.3 g of NaClO$_2$ (36.05 mmol) and 3.6 g of Na$_2$PO$_4$ (25.75 mmol). The batch is then stirred at ambient temperature for 7 hours. The reaction mixture is then concentrated in order to remove the acetone. Then solid then obtained is filtered off, washed with water and then dried at 40° C. in vacuo overnight. The title product is obtained in the form of a solid, which is subsequently used without being otherwise purified.

$^1$H NMR: δ (400 MHz; dmso-d6; 300K): 12.10 (m, 1H, H carboxylic acid); 7.40-6.88 (2s, 2H, aromatic Hs); 6.20 (s, 1H, H tetrahydroindolizine); 6.18 (s, 2H, H methylenedioxy); 3.70 (s, 3H, methyl ester); 3.55 (t, 2H tetrahydroindolizine); 3.00 (t, 2H tetrahydroindolizine); 1.80 (m, 4H, H tetrahydroindolizine)

IR: ν: —OH: 3000-2000 cm$^{-1}$ acid; ν: >C=O 1686-1676 cm$^{-1}$ ester+acid; ν: >C=C< 1608 cm$^{-1}$

Preparation 2: 2-[2-(tert-Butoxycarbonyl)-8-(methoxycarbonyl)-1,2,3,4-tetrahydropyrrolo[1,2-a]pyrazin-6-yl]-4-chlorobenzoic acid

Step A: 1-tert-Butyl 3-methyl 4-formyl-1,3-piperazinedicarboxylate

To a solution of pentafluorophenol in 520 mL of anhydrous ether placed at 0° C. there are successively added 49 g of 1-ethyl-3-(3'-dimethylaminopropyl)-carbodiimide (286 mmol) in portions and 12 mL of formic acid (312 mmol). The batch is stirred at ambient temperature for 2 hours. There is then added a mixture of 32 g of 1-tert-butyl 3-methyl 1,3-piperazinedicarboxylate (130 mmol) and 18 mL of triethylamine (130 mmol) dissolved in 520 mL of CH$_2$Cl$_2$. The batch is stirred overnight at ambient temperature. The reaction mixture is hydrolysed with 1N aqueous HCl solution and extracted with CH$_2$Cl$_2$. The organic phases are then combined and then washed with saturated aqueous NaHCO$_3$ solution and then with saturated aqueous NaCl solution until neutral. After drying over MgSO$_4$, filtering and concentrating to dryness, the product is isolated by chromatography over silica gel (petroleum ether/AcOEt gradient: 0-30%). The title product is obtained in the form of an oil.

IR: ν: C=O: 1674-1745 cm$^{-1}$ m/z (C$_{12}$H$_{20}$N$_2$O$_5$): 272.1 (M+); 295.121 (M+Na)$^+$; 567.253 (2M+Na)$^+$

Step B: Lithium 4-(tert-butoxycarbonyl)-1-formyl-2-piperazinecarboxylate

To a solution of 28 g of the compound obtained in Step A (103 mmol) in 515 mL of dioxane there are added 4.8 g of LiOH (113 mmol) dissolved in 100 mL of H$_2$O. The batch is stirred at ambient temperature for 4 hours. The reaction mixture is then concentrated to dryness and then co-evaporated several times with ethyl acetate. The title product is obtained in the form of a solid and is used directly in the following cyclisation step.

$^{13}$C NMR: δ (500 MHz; dmso-d6; 300K): 46 (s, C piperazine); 42-38 (m, C piperazine); 58-53 (s, C piperazine); 28.5 (s, C $^t$Bu)

IR: ν: C=O: 1650 cm$^{-1}$; 2800 cm$^{-1}$

Step C: 2-tert-Butyl 8-methyl 3,4-dihydropyrrolo[1,2-a]pyrazine-2,8(1H)-dicarboxylate To a suspension of 29 g of the compound obtained in Step B (103 mmol) in 800 mL of dichloromethane there are successively added 24 g of tosyl chloride (124 mmol), 12.6 mL of methyl 2-chloroacrylate (124 mmol) and then 35 mL of triethylamine (247 mmol). The batch is stirred at reflux for 2 hours. After cooling, the reaction mixture is diluted with ethyl acetate and the organic phase is washed with saturated NaCl solution until neutral. After drying over MgSO$_4$, filtering and concentrating to dryness, the title product is isolated by chromatography over silica gel (petroleum ether/AcOEt gradient: 0-20%) in the form of a solid.

$^1$H NMR: δ (400 MHz; dmso-d6; 300K): 6.8-6.43 (m, 2H, H pyrrole); 4.75-3.75 (m, 6H, H piperazine); 3.73 (s, 3H, H COOCH3); 1.48 (s, 9H, H $^t$Bu)

IR: ν: C=O (conjugated ester): 1712 cm$^{-1}$; C=O (carbamate): 1677 cm$^{-1}$

Step D: 2-[2-(tert-Butoxycarbonyl)-8-(methoxycarbonyl)-1,2,3,4-tetrahydropyrrolo[1,2-a]pyrazin-6-yl]-4-chlorobenzoic acid The procedure is in accordance with the protocol described in Steps C and D of Preparation 1, replacing the 6-bromo-1,3-benzodioxole-5-carbaldehyde used in Step C with 2-bromo-4-chlorobenzaldehyde.

Preparation 3: 4-Chloro-2-[1-(methoxycarbonyl)-5,6,7,8-tetrahydro-3-indolizinyl]-benzoic acid The procedure is in accordance with the process of Preparation 1, replacing the 6-bromo-1,3-benzodioxole-5-carbaldehyde used in Step C with 2-bromo-4-chlorobenzaldehyde.

Preparation 4: 7-[2-(tert-Butoxycarbonyl)-8-(methoxycarbonyl)-1,2,3,4-tetrahydropyrrolo[1,2-a]pyrazin-6-yl]-2,3-dihydro-1,4-benzodioxine-6-carboxylic acid

Step A: 2-tert-Butyl 8-methyl 3,4-dihydropyrrolo[1,2-a]pyrazine-2,8(1H)-dicarboxylate The procedure is in accordance with the process described in Steps A-C of Preparation 2.

$^1$H NMR: δ (400 MHz; dmso-d6; 300K): 6.8-6.43 (m, 2H, H pyrrole); 4.75-3.75 (m, 6H, H piperazine); 3.73 (s, 3H, H COOCH3); 1.48 (s, 9H, H $^t$Bu)

IR: ν: C=O (conjugated ester): 1712 cm$^{-1}$; C=O (carbamate): 1677 cm$^{-1}$

Step B: 7-[2-(tert-Butoxycarbonyl)-8-(methoxycarbonyl)-1,2,3,4-tetrahydropyrrolo[1,2-a]pyrazin-6-yl]-2,3-dihydro-1,4-benzodioxine-6-carboxylic acid The procedure is in accordance with the protocol described in Steps C and D of Preparation 1, replacing the 6-bromo-1,3-benzodioxole-5-carbaldehyde used in Step C with 7-bromo-2,3-dihydro-1,4-benzodioxine-6-carbaldehyde.

Preparation 5: 4-Chloro-2-[1-(methoxycarbonyl)-3-indolizinyl]benzoic acid

Step A: 1-(Carboxymethyl)-1,2-dihydropyridinium bromide

To a solution of 16.2 mL of pyridine (200 mmol) in 120 mL of ethyl acetate there are added, in portions, 27.8 g (200 mmol) of bromoacetic acid. The batch is then stirred at ambient temperature overnight. The precipitate thereby obtained is filtered off and then washed with cold ethyl acetate. After drying, the title product is obtained in the form of a powder which is used directly in the next Step.

$^1$H NMR: δ (400 MHz; dmso-d6; 300K): 9.15 (d, 2H, aromatic Hs pyridine); 8.7 (t, 1H, aromatic H); 8.25 (t, 2H, aromatic H); 5.65 (s, 2H, H CH$_2$COOH)

IR: ν: C=O: 1732 cm$^{-1}$; —OH acid: 2800 cm$^{-1}$

Step B: Methyl 1-indolizinecarboxylate

To a suspension of 6.55 g of the pyridinium salt obtained in Step A (30 mmol) in 240 mL of toluene there are successively added 16.7 mL of methyl acrylate (150 mmol), 4.2 mL of triethylamine (30 mmol) and then, in portions, 20.9 g of MnO$_2$ (240 mmol). The batch is then heated at 90° C. for 3 hours. After cooling, the reaction mixture is filtered over a cake of Celite and concentrated to dryness. The title product is then isolated by purification over silica gel (heptane/AcOEt gradient: 0-10%) in the form of an oil which crystallises in the cold state.

$^1$H NMR: δ (300 MHz; dmso-d6; 300K): 8.5 (d, 1H, H indolizine); 8.05 (d, 1H, H indolizine); 7.6 (s, 1H, H indolizine); 7.15 (m, 2H, H indolizine); 6.85 (m, 1H, H indolizine); 4.25 (q, 2H, —C(O)CH$_2$CH$_3$); 1.35 (t, 3H, —C(O)CH$_2$CH$_3$)

IR: ν: C=O ester: 1675 cm$^{-1}$; aromatic C=C moieties: 1634 cm$^{-1}$

Step C: 4-Chloro-2-[1-(methoxycarbonyl)-3-indolizinyl]benzoic acid

The procedure is in accordance with the protocol described in Steps C and D of Preparation 1, replacing the 6-bromo-1,3-benzodioxole-5-carbaldehyde used in Step C with 2-bromo-4-chlorobenzaldehyde.

Preparation 6: 2-[2-(tert-Butoxycarbonyl)-8-(methoxycarbonyl)-1,2,3,4-tetrahydropyrrolo[1,2-a]pyrazin-6-yl]-4-fluorobenzoic acid The procedure is in accordance with the protocol described in Preparation 2, replacing the 2-bromo-4-chlorobenzaldehyde used in Step D with 2-bromo-4-fluorobenzaldehyde.

Preparation 7: 6-[2-(tert-Butoxycarbonyl)-8-(methoxycarbonyl)-1,2,3,4-tetrahydropyrrolo[1,2-a]pyrazin-6-yl]-1,3-benzodioxole-5-carboxylic acid The procedure is in accordance with the protocol described in Preparation 2, replacing the 2-bromo-4-chlorobenzaldehyde used in Step D with 6-bromo-1,3-benzodioxole-5-carbaldehyde.

Preparation 8: 6-[1'-(Methoxycarbonyl)-5',6'-dihydro-8'H-spiro[1,3-dioxolane-2,7'-indolizin]-3'-yl]-1,3-benzodioxole-5-carboxylic acid Step A: Methyl 8-formyl-1,4-dioxa-8-azaspiro[4.5]decane-7-carboxylate 24 g of methyl 1,4-dioxa-8-azaspiro[4.5]decane-9-carboxylate (111 mmol) are dissolved in 80 mL of ethyl acetate and 80 mL of dichloromethane. There are added 26 g of (4-nitrophenyl)formate (155 mmol) and the batch is stirred at ambient temperature for 1 hour. The reaction mixture is evaporated to dryness and taken up in ethyl acetate. The organic phase is then successively washed with 1N NaOH solution, water and then with saturated NH$_4$Cl solution until a neutral pH is obtained. It is then dried over magnesium sulphate, filtered and concentrated to dryness. The oil thereby obtained is purified by flash chromatography (heptane/ethyl acetate gradient). The title product is obtained in the form of an oil.

$^1$H NMR: δ (400 MHz; dmso-d6; 300K): 8.15 (s, 1H, CHO); 5.0-4.75 (m, 1H, tertiary H); 4.3-3.7 (m, 5H, 4H ethylenedioxy+1H aliphatic piperidine); 3.70 (s, 3H, Me); 3.4-2.9 (2m, 1H, H aliphatic piperidine); 2.3-1.75 (m, 2H, H aliphatic piperidine); 1.7-1.5 (m, 2H, H aliphatic piperidine)

Step B: 8-Formyl-1,4-dioxa-8-azaspiro[4.5]decane-7-carboxylic acid 15.25 g of the compound obtained in Step A (62.7 mmol) is dissolved in 160 mL of dioxane. A solution of 125 mL of 1M KOH is added dropwise and the batch is stirred at ambient temperature for 1 hour. There are then added 125 mL of 1M HCl and the compound is extracted with dichloromethane. The organic phase is dried over MgSO$_4$, filtered and concentrated to dryness. The title product is obtained in the form of a powder.

$^1$H NMR: δ (400 MHz; dmso-d6; 300K) 13.5-12 (m, 1H, OH); 8.1+8.0 (2s, 1H, CHO); 4.9+4.6 (2m, 1H, tertiary H); 4.0-3.8 (m, 4H, ethylenedioxy); 4.2+3.7 (2 ms, 1H, H aliphatic piperidine); 3.4+2.9 (2m, 1H, H aliphatic piperidine); 2.4-1.5 (m, 4H, H aliphatic piperidine)

IR: ν: OH: 3500-2000 cm$^{-1}$; —C=O (acid+aldehyde): 1731+1655 cm$^{-1}$

Step C: Methyl 5',6'-dihydro-8'H-spiro[1,3-dioxolane-2, 7'-indolizine]-1'-carboxylate To a solution of 13.5 g (62.7 mmol) of the acid obtained in Step B in 380 mL of dichloromethane there are successively added 39.5 mL (238.4 mmol) of triethylamine and then, in portions, 12.5 g (65.6 mmol) of para-toluenesulphonyl chloride and 23.7 mL (238.4 mmol) of methyl chloroacrylate. The batch is stirred at 80° C. for 18 hours. The reaction mixture is then filtered over Celite. The filtrate is then washed with saturated NaHCO$_3$ solution and then with saturated NH$_4$Cl solution. The organic phase is dried over MgSO$_4$, filtered and concentrated to dryness. The oil thereby obtained is purified by flash chromatography (heptane/ethyl acetate gradient). The product is obtained in the form of a solid.

$^1$H NMR: δ (400 MHz; dmso-d6; 300K) 6.70 (d, 1H, pyrrole); 6.40 (d, 1H, pyrrole); 4.05 (t, 2H, H aliphatic, piperidine); 4.00 (m, 4H, ethylenedioxy); 3.70 (s, 3H, methyl); 3.15 (s, 2H, H aliphatic piperidine); 2.05 (t, 2H, H aliphatic piperidine)

IR: ν: —C=O (ester): 1689 cm$^{-1}$

Step D: Methyl 3'-(6-formyl-1,3-benzodioxol-5-yl)-5',6'-dihydro-8'H-spiro[1,3-dioxolane-2, 7'-indolizine]-1'-carboxylate The procedure is in accordance with the process of Step C of Preparation 1.

Step E: 6-[1'-(Methoxycarbonyl)-5',6'-dihydro-8'H-spiro[1,3-dioxolane-2,7'-indolizin]-3'-yl]-1,3-benzodioxole-5-carboxylic acid The procedure is in accordance with the process of Step D of Preparation 1.

Preparation 9: 6-[1-(Methoxycarbonyl)-3-indolizinyl]-1,3-benzodioxole-5-carboxylic acid The procedure is in accordance with the protocol described in Preparation 5, replacing the 2-bromo-4-chlorobenzaldehyde used in Step C with 6-bromo-1,3-benzodioxole-5-carbaldehyde.

Preparation 10: 4-Methyl-2-[1-(methoxycarbonyl)-5,6,7,8-tetrahydro-3-indolizinyl]-benzoic acid The procedure is in accordance with the protocol described in Preparation 1, replacing the 6-bromo-1,3-benzodioxole-5-carbaldehyde used in Step C with 2-bromo-4-methylbenz-aldehyde.

Preparation 11: 2-[1-(Methoxycarbonyl)-5,6,7,8-tetrahydro-3-indolizinyl]benzoic acid The procedure is in accordance with the protocol described in Preparation 1, replacing the 6-bromo-1,3-benzodioxole-5-carbaldehyde used in Step C with 2-bromobenzaldehyde.

Preparation 12: 6-[8-(Methoxycarbonyl)pyrrolo[1,2-a]pyrimidin-6-yl]-1,3-benzodioxole-5-carboxylic acid

Step A: Methyl pyrrolo[1,2-a]pyrimidine-8-carboxylate

To a solution of 6.2 g of methyl 2-pyrimidin-2-ylacetate (40.75 mmol) in 250 mL of acetone there are successively added 14.04 g (167 mmol) of $NaHCO_3$ in the form of a powder, 13.2 mL (203.75 mmol) of chloroacetaldehyde and then 3.54 g (40.75 mmol) of lithium bromide. The batch is heated at 60° C. for 24 hours. The reaction mixture is then concentrated to dryness, taken up in ethyl acetate, washed with water, dried over $MgSO_4$, filtered and then concentrated to dryness. The solid thereby obtained is then purified by chromatography over silica gel (AcOEt). The expected product is obtained in the form of an oil.

Mass spectrum:
Empirical formula: $C_8H_8N_2O_2$
LC/MS: m/z=[M+H]$^+$=177

Step B: Methyl 6-(6-formyl-1,3-benzodioxol-5-yl)pyrrolo[1,2-a]pyrimidine-8-carboxylate To a solution of 3.93 g of the compound obtained in Step A (22.3 mmol) in 80 mL of anhydrous dimethylacetamide there are added 7.66 g (33.45 mmol) of 6-bromo-1,3-benzodioxole-5-carbaldehyde and 4.4 g (44.6 mmol) of potassium acetate. The batch is degassed under nitrogen for 15 minutes. There are then added 1.56 g (2.23 mmol) of $PdCl_2(PPh_3)_4$ catalyst. The reaction mixture is heated at 130° C. for 16 hours under an inert atmosphere. After drying, the residue is taken up in dichloromethane; the batch is filtered over a cake of Celite and then the filtrate is washed with water, dried over $MgSO_4$ and concentrated to dryness. The black solid is then chromatographed over silica gel ($CH_2Cl_2$/MeOH 5%). The expected product is obtained in the form of a solid.

Mass Spectrum:
Empirical formula: $C_{17}H_{12}N_2O_3$
LC/MS: m/z=[M+H]$^+$=325

Step C: 6-[8-(Methoxycarbonyl)pyrrolo[1,2-a]pyrimidin-6-yl]-1,3-benzodioxole-5-carboxylic acid To a solution of 2.91 g (8.97 mmol) of the aldehyde obtained in Step B in 140 mL of acetone cooled to 0° C. there are added 2-methylbutene and then, dropwise, a mixture of 2.8 g (17.94 mmol) of $NaH_2PO_4.2H_2O$ and 2.84 g (31.4 mmol) of $NaClO_2$ dissolved in 30 mL of water. The batch is stirred at ambient temperature for 4 hours. The reaction mixture is then concentrated in vacuo to remove the acetone, placed at 0° C. and then acidified to pH=2-3 by adding 5N HCl solution dropwise. The formation of a precipitate is observed, which is filtered off, washed with water and then with diethyl ether and dried in vacuo.

$^1$H NMR: δ (400 MHz; dmso-d6; 300K): 12.7 (m, 1H, COOH); 8.45 (d, 1H, aromatic H, H pyrrolo[1,2-a]pyrimidine); 8.19 (d, 1H, aromatic H, H pyrrolo[1,2-a]pyrimidine); 6.9 (dd, 1H, aromatic H, H pyrrolo[1,2-a]pyrimidine); 7.51 (s, 1H, aromatic H); 7.21 (s, 1H, aromatic H); 7.07 (s, 1H, aromatic H); 6.2 (s, 2H, aliphatic Hs, O—$CH_2$—O); 3.8 (s, 3H, aliphatic Hs, COOCH$_3$)

IR: ν —OH—: 3300 to 1800 cm$^{-1}$; ν —CO—: 1705 cm$^{-1}$, ν>C=C<: 1616 cm$^{-1}$

Preparation 13: 4-Methoxy-2-[1-(methoxycarbonyl)-5,6,7,8-tetrahydro-3-indolizinyl]-benzoic acid The procedure is in accordance with the protocol described in Preparation 1, replacing the 6-bromo-1,3-benzodioxole-5-carbaldehyde used in Step C with 2-bromo-4-methoxy-benzaldehyde.

Preparation 14: 5-Methoxy-2-[1-(methoxycarbonyl)-5,6,7,8-tetrahydro-3-indolizinyl]-benzoic acid The procedure is in accordance with the protocol described in Preparation 1, replacing the 6-bromo-1,3-benzodioxole-5-carbaldehyde used in Step C with 2-bromo-5-methoxy-benzaldehyde.

Preparation 15: 7-[1-(Methoxycarbonyl)-5,6,7,8-tetrahydro-3-indolizinyl]-2,3-dihydro-1,4-benzodioxine-6-carboxylic acid The procedure is in accordance with the process of Preparation 1, replacing the 6-bromo-1,3-benzodioxole-5-carbaldehyde used in Step C with 7-bromo-2,3-dihydro-1,4-benzodioxine-6-carbaldehyde.

Preparation 16: 2-[1-(Methoxycarbonyl)-3-indolizinyl]benzoic acid

The procedure is in accordance with the process of Preparation 5, replacing the 2-bromo-4-chlorobenzaldehyde used in Step C with 2-bromo-benzaldehyde.

Preparation 17: 4-Fluoro-2-[1-(methoxycarbonyl)-3-indolizinyl]benzoic acid

The procedure is in accordance with the process of Preparation 5, replacing the 2-bromo-4-chlorobenzaldehyde used in Step C with 2-bromo-4-fluorobenzaldehyde.

Preparation 18: 4-Fluoro-2-[1-(methoxycarbonyl)-5,6,7,8-tetrahydro-3-indolizinyl]-benzoic acid The procedure is in accordance with the process of Preparation 1, replacing the 6-bromo-1,3-benzodioxole-5-carbaldehyde used in Step C with 2-bromo-4-fluorobenzaldehyde.

Preparation 1': (3R)-3-Methyl-1,2,3,4-tetrahydroisoquinoline hydrochloride

Step A: {(3S)-2-[(4-Methylphenyl)sulphonyl]-1,2,3,4-tetrahydroisoquinolin-3-yl}methyl 4-methylbenzenesulphonate To a solution of 30.2 g of [(3S)-1,2,3,4-tetrahydroisoquinolin-3-yl]methanol (185 mmol) in 750 mL of dichloromethane there are successively added 91.71 g of tosyl chloride (481 mmol) and then, dropwise, 122.3 mL of N,N,N-triethylamine (740 mmol). The reaction mixture is then stirred at ambient temperature for 20 hours. It is then diluted with dichloromethane, washed successively with 1M HCl solution, saturated NaHCO$_3$ solution and then saturated NaCl solution until neutral. The organic phase is then dried over MgSO$_4$, filtered and concentrated to dryness. The solid obtained is then dissolved in a minimum volume of dichloromethane and then cyclohexane is added until a precipitate is formed. This precipitate is then filtered off and washed with cyclohexane. After drying, the title product is obtained in the form of crystals.

$^1$H NMR: δ (400 MHz; dmso-d6; 300K): 7.75 (d, 2H, aromatic Hs, ortho O-tosyl); 7.6 (d, 2H, aromatic Hs, ortho N-tosyl); 7.5 (d, 2H, aromatic Hs, meta O-tosyl); 7.3 (d, 2H, aromatic Hs, meta N-tosyl); 7.15-6.9 (m, 4H, aromatic Hs, tetrahydroisoquinoline); 4.4-4.15 (dd, 2H, aliphatic Hs, tetrahydroisoquinoline); 4.25 (m, 1H, aliphatic H, tetrahydroisoquinoline); 4.0-3.8 (2dd, 2H, aliphatic Hs, CH$_2$—O-tosyl); 2.7 (2dd, 2H, aliphatic Hs, tetrahydroisoquinoline); 2.45 (s, 3H, O—SO$_2$-Ph-CH$_3$); 2.35 (s, 3H, N—SO$_2$-Ph-CH$_3$)

IR: ν: —SO$_2$: 1339-1165 cm$^{-1}$

Step B: (3R)-3-Methyl-2-[(4-methylphenyl)sulphonyl]-1,2,3,4-tetrahydroisoquinoline To a suspension of 8.15 g (214.8 mmol) of LiAlH$_4$ in 800 mL of methyl tert-butyl ether (MTBE) there are added 101.2 g of the ditosyl compound obtained in Step A (214.8 mmol) dissolved in 200 mL of MTBE. The batch is then heated at 50° C. for 2 hours. It is allowed to cool and placed at 0° C., and there are then added, dropwise, 12 mL of 5N NaOH solution. The batch is stirred at ambient temperature for 45 minutes. The solid thereby obtained is then filtered off and washed with MTBE and then with dichloromethane. The filtrate is then concentrated to dryness. The title product is then obtained in the form of a solid.

$^1$H NMR: δ (400 MHz; dmso-d6; 300K): 7.70 (d, 2H, aromatic Hs, ortho N-tosyl); 7.38 (d, 2H, aromatic Hs, meta N-tosyl); 7.2-7.0 (m, 4H, aromatic Hs, tetrahydroisoquinoline); 4.4 (m, 2H, aliphatic Hs, tetrahydroisoquinoline); 4.3 (m, 1H, aliphatic H, tetrahydroisoquinoline); 2.85-2.51 (2dd, 2H, aliphatic Hs, tetrahydroisoquinoline); 2.35 (s, 3H, N—SO$_2$-Ph-CH$_3$); 0.90 (d, 3H, tetrahydroisoquinoline-CH$_3$)

IR: ν: —SO$_2$: 1332-1154 cm$^{-1}$

Step C: (3R)-3-Methyl-1,2,3,4-tetrahydroisoquinoline

To a solution of 31.15 g (103.15 mmol) of the monotosyl compound obtained in Step B in 500 mL of anhydrous methanol there are added, in portions, 3.92 g (161 mmol) of magnesium turnings. The batch is stirred in the presence of ultrasound for 96 hours. The reaction mixture is then filtered and the solid is washed several times with methanol. The filtrate is then concentrated to dryness. After purification by column chromatography over silica gel (dichloromethane/EtOH/NH$_4$OH), the title product is obtained in the form of an oil.

$^1$H NMR: δ (400 MHz; dmso-d6; 300K): 7.05 (m, 4H, aromatic Hs, tetrahydroisoquinoline); 3.90 (m, 2H, aliphatic Hs, tetrahydroisoquinoline); 2.85 (m, 1H, aliphatic H, tetrahydroisoquinoline); 2.68-2.4 (2dd, 2H, aliphatic Hs, tetrahydroisoquinoline); 1.12 (d, 3H, tetrahydroisoquinoline-CH$_3$); 2.9-2.3 (m, broad, 1H, HN (tetrahydroisoquinoline))

IR: ν: —NH: 3248 cm$^{-1}$

Step D: (3R)-3-Methyl-1,2,3,4-tetrahydroisoquinoline hydrochloride

To a solution of 14.3 g (97.20 mmol) of the compound obtained in Step C in 20 mL of anhydrous ethanol there are added, dropwise, 100 mL of a 1M solution of HCl in ether. The batch is stirred at ambient temperature for 1 hour and then filtered. The crystals thereby obtained are washed with ethyl ether. After drying, the title product is obtained in the form of crystals.

$^1$H NMR: δ (400 MHz; dmso-d6; 300K): 9.57 (m, broad, 2H, NH$_2^+$ (tetrahydroisoquinoline)); 7.22 (m, 4H, aromatic Hs, tetrahydroisoquinoline); 4.27 (s, 2H, aliphatic Hs, tetrahydroisoquinoline); 3.52 (m, 1H, aliphatic H, tetrahydroisoquinoline); 3.03-2.85 (2dd, 2H, aliphatic Hs, tetrahydroisoquinoline); 1.39 (d, 3H, tetrahydroisoquinoline-CH$_3$)

IR: ν: —NH$_2$+: 3000-2300 cm$^{-1}$; ν: aromatic —CH: 766 cm$^{-1}$

Preparation 2': (3S)-3-[2-(Morpholin-4-yl)ethyl]-1,2,3,4-tetrahydroisoquinoline hydrochloride

Step A: tert-Butyl (3S)-3-(2-morpholino-2-oxoethyl)-3,4-dihydro-1H-isoquinoline-2-carboxylate To a solution of 3 g (10.30 mmol) of [(3S)-2-(tert-butoxycarbonyl)-1,2,3,4-tetrahydroisoquinolin-3-yl]acetic acid in 100 mL of dichloromethane there are added, dropwise, 1.10 mL (11.32 mmol) of morpholine and, still dropwise, 4.3 mL (30.9 mmol) of triethylamine, 2.20 g (12.40 mmol) of 1,2-dichloromethane and 1.70 g (1.68 mmol) of hydroxybenzotriazole. The batch is stirred at ambient temperature for 15 hours. The reaction mixture is then diluted with dichloromethane and washed successively with 1M HCl solution, saturated NaHCO$_3$ solution and then saturated NaCl solution until neutral. The organic phase is then dried over MgSO$_4$, filtered and concentrated to dryness. After purification by column chromatography over silica gel (dichloromethane/MeOH), the title product is obtained in the form of an oil.

$^1$H NMR: δ (400 MHz; dmso-d6; 300K): 7.20-7.10 (m, 4H, aromatic Hs, tetrahydroisoquinoline); 4.70 (m, 1H, aliphatic Hs, CH tetrahydroisoquinoline); 4.75-4.20 (2m, 2H, aliphatic Hs, CH₂ alpha to N tetrahydroisoquinoline); 3.60 (m, 8H, aliphatic Hs, morpholine); 3.00 and 2.70 (2dd, 2H, aliphatic H, tetrahydroisoquinoline); 2.50-2.20 (2d, 2H, aliphatic Hs, CH₂CO); 1.40 (s, 9H, ᵗBu)

IR: ν: C═O: 1687; 1625 cm⁻¹

Step B: 1-(Morpholin-4-yl)-2-[(3S)-1,2,3,4-tetrahydroisoquinolin-3-yl]ethanone hydrochloride To a solution of 2.88 g (7.18 mmol) of the compound obtained in Step A in 16 mL of dichloromethane there are added, dropwise, 80 mL (80 mmol) of a 1M solution of HCl in ether. The batch is stirred at ambient temperature for 15 hours and then the suspension is filtered and the precipitate is washed with ether. After drying, the title product is obtained in the form of a solid.

¹H NMR: δ (400 MHz; dmso-d6; 300K): 9.80-9.50 (m, 2H, NH₂⁺); 7.30-7.10 (m, 4H, aromatic Hs, tetrahydroisoquinoline); 4.30 (m, 2H, aliphatic Hs, CH₂ alpha to N tetrahydroisoquinoline); 3.80 (m, 1H, aliphatic Hs, CH tetrahydroisoquinoline); 3.70-3.40 (2m, 8H, aliphatic Hs, morpholine); 3.15 and 2.8 (m, 4H, aliphatic H, CH₂ tetrahydroisoquinoline and CH₂CO)

IR: ν: —NH₂+: 2800-1900 cm⁻¹; ν: C═O: 1620 cm⁻¹

Step C: (3S)-3-[2-(Morpholin-4-yl)ethyl]-1,2,3,4-tetrahydroisoquinoline hydrochloride A solution of 2.2 g (7.44 mmol) of the compound obtained in Step B in 22 mL of MTBE and 5 mL of dichloromethane is prepared. After cooling in an ice bath at 0° C., there are added thereto, dropwise, 15 mL (15 mmol) of 1M LiAlH₄ solution in tetrahydrofuran. The batch is then stirred at ambient temperature for 6 hours. It is placed at 0° C., and there is then added, dropwise, 1 mL of 5N NaOH solution. The batch is stirred at ambient temperature for 45 minutes. The solid is then filtered off and washed with MTBE and then with dichloromethane and the filtrate is concentrated to dryness. The oil thereby obtained is diluted with dichloromethane and there are added, dropwise, 6.3 mL of a 1M solution of HCl in ether. The batch is stirred at ambient temperature for 1 hour and then filtered. The crystals thereby obtained are washed with ethyl ether. After drying, the title product is obtained in the form of a solid.

¹H NMR: δ (400 MHz; dmso-d6; 300K): 11.35+9.80 (2m, 2H, NH₂⁺); 10.00 (m, H, NH⁺); 7.20 (m, 4H, aromatic Hs, tetrahydroisoquinoline); 4.30 (s, 2H, aliphatic Hs, CH₂ alpha to N tetrahydroisoquinoline); 4.00+3.85 (2m, 4H, aliphatic Hs, CH₂ alpha to N morpholine); 3.70 (m, 1H, aliphatic Hs, CH tetrahydroisoquinoline); 3.55-3.30 (m, 4H, aliphatic Hs, CH alpha to O morpholine and CH₂-morpholine); 3.15 (dd, 1H, aliphatic H, CH₂ tetrahydroisoquinoline); 3.10 (m, 2H, aliphatic H, CH alpha to 0 morpholine); 2.90 (dd, 1H, aliphatic H, CH₂ tetrahydroisoquinoline); 2.30+2.15 (2m, 2H, aliphatic H, CH₂-tetrahydroisoquinoline)

IR: ν: NH⁺/—NH₂+: between 3500 and 2250 cm⁻¹; ν: C═C: weak 1593 cm⁻¹; ν: aromatic C—H: 765 cm⁻¹

Preparation 3': tert-Butyl {2-[(3S)-1,2,3,4-tetrahydroisoquinolin-3-yl]ethyl}-carbamate

Step A: Benzyl (3S)-3-(2-hydroxyethyl)-3,4-dihydroisoquinoline-2(1H)-carboxylate The title compound is obtained starting from (3S)-2-[(benzyloxy)carbonyl]-1,2,3,4-tetrahydroisoquinoline-3-carboxylic acid based on a protocol from the literature (Jinlong Jiang et al *Bioorganic & Medicinal Chemistry Letters,* 14, 1795, 2004).

Step B: Benzyl (3S)-3-{2-[(methylsulphonyl)oxy]ethyl}-3,4-dihydroisoquinoline-2(1H)-carboxylate To a solution of 10.6 g of the compound of Step A (35.6 mmol) in 350 mL of anhydrous CH₂Cl₂ placed at 0° C. there are successively added 10.1 mL of triethylamine (71.2 mmol) and then, dropwise, 3.1 mL of methanesulphonyl chloride (39 mmol). The reaction mixture is then stirred at ambient temperature for 2 hours. Hydrolysis is then carried out by slowly adding water. The product is extracted several times with CH₂Cl₂. The organic phases are then combined and successively washed with 1N HCl solution, saturated NaCl solution, saturated NaHCO₃ solution and saturated NaCl solution until neutral. They are then dried over MgSO₄ and concentrated to dryness. After purification by chromatography over silica gel (petroleum ether/AcOEt gradient), the expected product is obtained in the form of a foam.

LC/MS: m/z=(M+H)⁺=375

Step C: Benzyl (3S)-3-(cyanomethyl)-3,4-dihydroisoquinoline-2(1H)-carboxylate To a solution of 15.4 g of the compound obtained in Step B (41.02 mmol) in 250 mL of anhydrous DMSO there are added 22 g (449 mmol) of sodium cyanide. The batch is then heated at 60° C. for 12 hours. It is allowed to cool and then the reaction mixture is diluted by adding ethyl acetate. Hydrolysis is then carried out with saturated NaHCO₃ solution. After extracting two more times with ethyl acetate, the organic phases are combined, washed with H₂O, dried over MgSO₄ and concentrated to dryness. After purification by chromatography over silica gel (hexane/AcOEt 7/3), the expected product is obtained in the form of an oil.

LC/MS: m/z=[M+H]⁺=307.1

Step D: Benzyl (3S)-3-(2-aminoethyl)-3,4-dihydroisoquinoline-2(1H)-carboxylate To a solution of 15.4 g of the compound obtained in Step C (50.3 mmol) in 300 mL of anhydrous THF placed at 0° C. there are added, dropwise, a 1N solution of BH₃-THF. The reaction mixture is allowed to come back to ambient temperature gradually and then the batch is stirred for 14 hours. The reaction mixture is then hydrolysed by slowly adding saturated NH₄Cl solution. After extracting twice with ethyl acetate, the organic phases are combined and dried over MgSO₄. After concentrating to dryness, the expected product is obtained in the form of a foam which is used directly without purification in the next protection step.

Step E: Benzyl (3S)-3-{2-[(tert-butoxycarbonyl)amino]ethyl}-3,4-dihydroisoquinoline-2(1H)-carboxylate To a solution of 15.6 g of the compound obtained in Step D (50.3 mmol) in 670 mL of CH₂Cl₂ there are successively added, in portions, 13.2 g (60.36 mmol) of Boc₂O, 14 mL of triethylamine (100.6 mmol) and DMAP in a catalytic amount. The batch is stirred at ambient temperature for 5 hours. The reaction mixture is then hydrolysed with water and extracted twice with CH₂Cl₂. The organic phases are combined, washed with water and dried over MgSO₄. After concentration to dryness and purification by chromatography over silica gel (heptane/AcOEt gradient), the expected product is obtained in the form of an oil.
LC/MS: m/z=(M+H)$^+$=411

Step F: tert-Butyl {2-[(3S)-1,2,3,4-tetrahydroisoquinolin-3-yl]ethyl}carbamate To a solution of 10.4 g of the compound obtained in Step E (25.5 mmol) in 210 mL of anhydrous MeOH there are added 2.71 g (2.55 mmol) of Pd/C 10%. The batch is degassed for 30 minutes and is then stirred under a hydrogen atmosphere for 16 hours. The reaction mixture is then filtered and concentrated to dryness. The expected product is obtained in the form of a solid which is taken up in a mixture of pentane/Et$_2$O (90/10), triturated and filtered. After drying, the product is obtained in the form of a solid.

$^1$H NMR: δ (400 MHz; dmso-d6; 300K): 7.1-6.98 (m, 4H, aromatic Hs, tetrahydroisoquinoline); 6.83 (m, 1H, CH$_2$NHBoc); 3.85 (s, 2H, aliphatic Hs, tetrahydroisoquinoline); 3.09 (q, 2H, CH$_2$NHBoc); 2.73 (m, 1H, aliphatic Hs, tetrahydroisoquinoline); 2.70 and 2.39 (2m, 2H, aliphatic Hs, tetrahydroisoquinoline); 1.63 (m, 2H, aliphatic Hs); 1.38 (s, 9H, NHCOOtBu)
IR: v: >NH: 3378, −3201 cm$^{-1}$ (amine, amide); v: >C=O: 1683 cm$^{-1}$ (amide); v: >NH: 1524 cm$^{-1}$ (amide); v: >C=O: 1168 cm$^{-1}$
LC/MS: m/z=[M+H]$^+$=277

Preparation 4': (3R)-3-[3-(Morpholin-4-yl)propyl]-1,2,3,4-tetrahydroisoquinoline

Step A: {(3S)-2-[(4-Methylphenyl)sulphonyl]-1,2,3,4-tetrahydroisoquinolin-3-yl}methyl 4-methylbenzenesulphonate The procedure is the same as that of Step A of Preparation 1'.

Step B: tert-Butyl 2-({(3R)-2-[(4-methylphenyl)sulphonyl]-1,2,3,4-tetrahydroisoquinolin-3-yl}methyl)-3-(morpholin-4-yl)-3-oxopropanoate To a suspension of 1 g of NaH (60%) (25.08 mmol) in 30 mL of MTBE there are added, dropwise, a solution of 5 g of tert-butyl 3-morpholino-3-oxopropanoate (21.81 mmol) in 20 mL of anhydrous MTBE. This suspension stirred at ambient temperature for 1 hour and then the compound obtained in Step A is added in the form of a powder. The batch is stirred at 60° C. for 30 hours. 100 mL of saturated ammonium chloride solution are added. The resulting solution is extracted with dichloromethane. The organic phase is then dried over MgSO$_4$, filtered and concentrated to dryness. After purification by column chromatography over silica gel (dichloromethane/MeOH), the expected product is obtained in the form of an oil.

$^1$H NMR (500 MHz; dmso-d6) δ ppm: 7.63/7.59 (2d, 2H), 7.3/7.26 (2d, 2H); 7.13 (m, 2H), 7.09/6.97 (2t, 2H), 4.64/4.55/4.36/4.28 (2AB, 2H), 4.25/4.11 (2m, 1H), 3.81 (m, 1H), 3.73/3.48 (m, 4H), 3.57-3.32 (m, 4H), 2.51 (m, 2H), 2.32/2.31 (2s, 3H), 1.88/1.79 (2m, 2H), 1.39/1.38 (2s, 9H).
IR (ATR) cm$^{-1}$: v: >C=O: 1731 (ester); v: >C=O: 1644 (amide); v: —SO2: 1334-1156; v: >C—O—C<: 1155; γ: >CH—Ar: 815-746-709

Step C: 2-({(3R)-2-[(4-Methylphenyl)sulphonyl]-1,2,3,4-tetrahydroisoquinolin-3-yl}methyl)-3-(morpholin-4-yl)-3-oxopropanoic acid To a solution of 9.5 g (17.97 mmol) of the compound obtained in Step B in 40 mL of dioxane there are added, dropwise, 20 mL of a 4M solution of HCl in dioxane. The batch is stirred at ambient temperature for 48 hours and then the solution is concentrated to dryness. After drying, the expected product is obtained in the form of an oil.

$^1$H NMR (400 MHz; dmso-d6) δ ppm: 12.75 (m, 1H), 7.6 (2*d, 2H); 7.3 (2*d, 2H), 7.1/6.95 (2*m, 4H), 4.7/4.2 (d, 2H), 4.25/4.12 (2*m, 1H), 3.9-3.3 (m, 9H), 2.55 (d, 2H), 2.3 (2*s, 3H), 1.8 (t, 2H)
IR (ATR) cm$^{-1}$: v: —OH: 3500 to 2000; v: >C=O: 1727 (acid); v: >C=O: 1634 (amide); v: —SO2: 1330-1155

Step D: 3-{(3R)-2-[(4-Methylphenyl)sulphonyl]-1,2,3,4-tetrahydroisoquinolin-3-yl}-1-(morpholin-4-yl)propan-1-one To a solution of 7.80 g (16.51 mmol) of the compound obtained in Step C in 100 mL of DMSO there are added 1.16 g (19.83 mmol) of solid sodium chloride and then, dropwise, 5 mL of water. The batch is stirred at 130° C. for 1 hour and then the solution is concentrated to ¾. The reaction mixture is then diluted with dichloromethane and washed successively with saturated lithium chloride solution and then with saturated NaCl solution. The organic phase is then dried over MgSO$_4$, filtered and concentrated to dryness. After purification by column chromatography over silica gel (cyclohexane/ethyl acetate), the expected product is obtained in the form of an oil.

$^1$H NMR (400 MHz; dmso-d6) δ ppm: 7.65 (d, 2H), 7.3 (d, 2H); 7.15/7 (2m, 4H), 4.6 (d, 1H), 4.25 (d, 1H), 4.2 (m, 1H), 3.5 (m, 4H), 3.4 (2 m, 4H), 2.6 (2 dd, 2H), 2.35 (s, 3H), 2.3 (m, 2H), 1.5 (quad., 2H)
IR (ATR) cm$^{-1}$: v: >C=O: 1639; v: —SO2: 1331-1156; γ: >CH—Ar: 815-675

Step E: (3R)-2-[(4-Methylphenyl)sulphonyl]-3-[3-(morpholin-4-yl)propyl]-1,2,3,4-tetrahydroisoquinoline To a solution of 6.0 g (14.0 mmol) of the compound obtained in Step D in 60 mL of MTBE and 14 mL of dichloromethane there are added 1.06 g (28 mmol) of LAH in portions over 5 minutes. The batch is stirred at ambient temperature for 15 hours. There are added, dropwise, 1.5 mL of water and stirring is carried out for 15 minutes. There are then added, dropwise, 1.5 mL of 5M sodium hydroxide solution and stirring is carried out for 15 minutes. The reaction mixture is then diluted with MTBE and dichloromethane. The suspension is then filtered and the precipitate is washed with MTBE and dichloromethane. The organic phase is then dried over MgSO$_4$, filtered and concentrated to dryness. After purification by column chromatography over silica gel (dichloromethane/EtOH/NH$_4$OH), the expected product is obtained in the form of an oil.

$^1$H NMR (400 MHz; dmso-d6) δ ppm: 7.68 (d, 2H), 7.32 (d, 2H); 7.1 (unresolved peak, 4H), 4.65/4.23 (AB, 2H), 4.2 (m, 1H), 3.55 (t, 4H), 2.7/2.6 (ABx, 2H), 2.35 (s, 3H), 2.25 (t, 4H), 2.2 (t, 2H), 1.4/1.3 (2m, 4H)
IR (ATR) cm$^{-1}$: v: —SO2: 1333-1158

Step F: (3R)-3-[3-(Morpholin-4-yl)propyl]-1,2,3,4-tetrahydroisoquinoline

To a solution of 1.50 g (3.62 mmol) of the compound obtained in Step E in 20 mL of anhydrous methanol there are added 2.0 g (82.3 mmol), in portions, of magnesium turnings. The batch is stirred in the presence of ultrasound for 96 hours. The reaction mixture is then filtered, the solid is washed several times with methanol, and the filtrate is concentrated to dryness. After purification by column chromatography over silica gel (dichloromethane/EtOH/NH$_4$OH), the expected product is obtained in the form of an oil.

$^1$H NMR (400 MHz; dmso-d6) δ ppm: 7.3 (d, 2H), 7.1 (t, 2H); 7.1 (d+t, 3H), 7 (d, 2H), 3.9 (s, 2H), 3.55 (t, 4H), 2.75 (m, 1H), 2.72/2.45 (dd, 2H), 2.35 (t, 4H), 2.25 (t, 2H), 1.6 (m, 2H), 1.45 (m, 2H)

IR (ATR) cm$^{-1}$: ν: >NH2+/NH+: 3500-2300; ν: >C—O—C<: 1115

High-Resolution Mass Spectroscopy (ESI+−/FIA/HR): Empirical formula: C$_{16}$H$_{24}$N$_2$O
[M+H]$^+$, calculated: 261.1961
[M+H]$^+$, measured: 261.1959

Preparation 5': (3S)-3-[2-(3,3-Difluoropiperidin-1-yl)ethyl]-1,2,3,4-tetrahydroisoquinoline hydrochloride The procedure is in accordance with the process of Preparation 2', replacing the morpholine used in Step A with 3,3-difluoro-1-piperidine.

$^1$H NMR: δ (400 MHz; dmso-d6; 300K): 11.3 (m, 1H, NH$^+$); 10.2-9.8 (m, 2H, NH$_2$$^+$); 7.25 (m, 4H, aromatic Hs, tetrahydroisoquinoline); 4.3 (broad s, 2H, aliphatic Hs, CH tetrahydroisoquinoline); 4.0-3.3 (m, 7H, aliphatic Hs); 3.15-2.95 (dd, 2H, aliphatic Hs, CH tetrahydroisoquinoline); 2.4-1.9 (m, 6H, aliphatic Hs, H 3,3-difluoro-1-piperidine)

IR: ν: NH$^+$/NH$_2$$^+$: between 300 and 2500 cm$^{-1}$; ν: C—F: 1204 cm$^{-1}$ Preparation 6': (3S)-3-[2-(3-Methoxyazetidin-1-yl)ethyl]-1,2,3,4-tetrahydroisoquinoline hydrochloride The procedure is in accordance with the process of Preparation 2', replacing the morpholine used in Step A with 3-methoxyazetidine.

$^1$H NMR: δ (400 MHz; dmso-d6; 300K): 11.3 (m, 1H, NH$^+$); 10.00 (m, 2H, NH$_2$$^+$); 7.20 (m, 4H, aromatic Hs, tetrahydroisoquinoline); 4.4 (m, 1H, aliphatic H, 3-methoxy azetidine); 4.30 (s, 2H, aliphatic Hs, tetrahydroisoquinoline); 4.2-3.45 (m, 4H, 3-methoxyazetidine); 4.2-3.6 (m, 3H, aliphatic Hs); 3.1 and 2.95 (dd, 2H, aliphatic Hs); 3.25 (s, 3H, OCH$_3$)

Preparation 7': (3S)-3-Methyl-1,2,3,4-tetrahydroisoquinoline hydrochloride

The procedure is in accordance with the process of Preparation 1', replacing the [(3S)-1,2,3,4-tetrahydroisoquinolin-3-yl]methanol used in Step A with [(3R)-1,2,3,4-tetrahydroisoquinolin-3-yl]methanol.

Preparation 1": N-(4-{[tert-Butyl(dimethyl)silyl]oxy}phenyl)-1-methyl-1H-pyrazol-4-amine Step A: 4-{[tert-Butyl(dimethyl)silyl]oxy}aniline The title compound is obtained starting from 4-aminophenol in THF in the presence of imidazole and tert-butyl (dimethyl)silyl chloride in accordance with the protocol described in the literature (S. Knaggs et al, *Organic & Biomolecular Chemistry*, 3(21), 4002-4010; 2005).

$^1$H NMR: δ (400 MHz; dmso-d6; 300K): 6.45-6.55 (dd, 4H, aromatic Hs); 4.60 (m, 2H, NH$_2$-Ph); 0.90 (s, 9H, Si(CH$_2$)$_2$CH(CH$_3$)$_2$); 0.10 (s, 6H, Si (CH$_2$)$_2$CH(CH$_3$)$_2$)
IR: ν: —NH$_2$+: 3300-3400 cm$^{-1}$ Step B: N-[4-[tert-Butyl(dimethyl)silyl]oxyphenyl]-1-methyl-pyrazol-4-amine To a solution of 30.8 g (0.137 mol) of the compound of Step A in 525 mL of anhydrous toluene there are successively added 29.8 g of sodium tert-butylate (0.310 mol), 4.55 g of Pd$_2$(dba)$_3$ (also referred to as tris(dibenzylideneacetone) dipalladium(0)) (4.96 mmol), 4.81 g of 2-di-tert-butylphosphino-2',4',6'-tri-isopropyl-1,1'-biphenyl (9.91 mmol) and 12.8 mL of 4-bromo-1-methyl-1H-pyrazole (0.124 mol). The batch is degassed under argon for 30 minutes and then refluxed for 3 hours. It is allowed to cool. The reaction mixture is concentrated to dryness and then taken up in dichloromethane, filtered over Celite and then concentrated to dryness again. The residue is then purified by chromatography over silica gel (gradient CH$_2$Cl$_2$/AcOEt) to provide the expected product in the form of a solid.

$^1$H NMR: δ (400 MHz; dmso-d6; 300K): 7.55 (s, 1H, pyrazole); 7.23 (s, 1H, pyrazole); 7.18 (broad s, 1H, NH$_2$-Ph); 6.64 (m, 4H, aromatic Hs); 3.77 (s, 3H, CH$_3$-pyrazole); 0.90 (s, 9H, Si (CH$_2$)$_2$CH(CH$_3$)$_2$); 0.12 (s, 6H, Si (CH$_2$)$_2$CH(CH$_3$)$_2$)

IR: ν —NH$^+$: 3275 cm$^{-1}$; ν Ar and C═N: 1577 and 1502 cm$^{-1}$; ν —Si—C—: 1236 cm$^{-1}$; ν —Si—O—: 898 cm$^{-1}$; ν —Si—C—: 828, 774 cm$^{-1}$ Preparation 2": N-(4-{[tert-Butyl(dimethyl)silyl]oxy}phenyl)-1-methyl-1H-indol-5-amine The procedure is in accordance with the process of Preparation 1", replacing the 4-bromo-1-methyl-1H-pyrazole used in Step B with 5-bromo-1-methyl-1H-indole.

Preparation 3": N-(4-{[tert-Butyl(dimethyl)silyl]oxy}phenyl)-1-[2-(morpholin-4-yl)ethyl]-1H-indol-5-amine Step A: 5-Bromo-1-[2-(morpholin-4-yl)ethyl]-1H-indole To a suspension of NaH (4.5 g; 112 mmol) in anhydrous THF (300 mL) placed at 0° C. there are added, in portions, 5-bromo-1H-indole (10.4 g; 51 mmol). After stirring for 20 minutes at 0° C., 4-(2-chloroethyl)morpholine hydrochloride (10.4 g; 56 mmol) is added in portions over 1 hour. After stirring overnight at ambient temperature, the reaction mixture is placed at 80° C. for 5 hours. It is then poured over a mixture of aqueous sodium bicarbonate and dichloromethane. The aqueous phase is extracted with dichloromethane. The organic phase is dried over MgSO$_4$ and concentrated to dryness, and the residue is purified by chromatography over silica gel (CH$_2$Cl$_2$/MeOH gradient) to provide the expected product in the form of an oil.

$^1$H NMR: δ (400 MHz; CDCl3; 300K): 7.75 (d, 1H); 7.30 (dd, 1H); 7.20 (d, 1H); 7.15 (d, 1H); 6.40 (d, 1H); 4.20 (t, 2H); 3.70 (m, 4H); 2.75 (t, 2H); 2.45 (m, 4H)

Step B: 5-Bromo-1-[2-(morpholin-4-yl)ethyl]-1H-indole

The procedure is in accordance with the process of Preparation 1", replacing the 4-bromo-1-methyl-1H-pyrazole used in Step B with the compound obtained in Step A.

¹H NMR: δ (400 MHz; dmso-d6; 300K): 7.35 (d, 1H); 7.15 (s, 1H); 6.85 (d, 3H); 6.70 (d, 2H); 7.30 (d, 1H); 6.25 (d, 1H); 4.20 (t, 2H); 3.55 (m, 4H); 2.65 (t, 2H); 2.45 (m, 4H); 1.45 (s, 9H), 0.15 (s, 6H)

Preparation 4": N-(4-{[tert-Butyl(dimethyl)silyl]oxy}phenyl)-1-[2-(morpholin-4-yl)ethyl]-2,3-dihydro-1H-indol-5-amine The procedure is in accordance with the process of Preparation 2", replacing the 5-bromoindole used in Step A with 5-bromo-2,3-dihydro-1H-indole.

Preparation 5": N-(4-{[tert-Butyl(dimethyl)silyl]oxy}phenyl)-4-fluoroaniline

The procedure is in accordance with the process of Preparation 1", replacing the 4-bromo-1-methyl-1H-pyrazole used in Step B with 1-bromo-4-fluorobenzene.

Preparation 6": N-(4-{[tert-Butyl(dimethyl)silyl]oxy}phenyl)-3-fluoro-4-methylaniline The procedure is in accordance with the process of Preparation 1", replacing the 4-bromo-1-methyl-1H-pyrazole used in Step B with 4-bromo-2-fluoro-1-methylbenzene.

Preparation 7": N-(4-{[tert-Butyl(dimethyl)silyl]oxy}phenyl)-1-methyl-1H-indazol-5-amine The procedure is in accordance with the process of Preparation 1", replacing the 4-bromo-1-methyl-1H-pyrazole used in Step B with 5-bromo-1-methyl-1H-indazole.

Preparation 8": 4-{[tert-Butyl(dimethyl)silyl]oxy}-N-phenylaniline

To a solution of 12 g of 4-anilinophenol (64.7 mmol) in 200 mL of acetonitrile there are added, at ambient temperature, 6.7 g of imidazole (97.05 mmol) and 11.7 g of tert-butyl-(chloro)dimethylsilane (77.64 mmol). The batch is stirred at 70° C. for 4 hours. The reaction mixture is then poured into water and extracted with ether. The organic phase is then dried over magnesium sulphate, then filtered and evaporated to dryness. The crude product thereby obtained is then purified by chromatography over silica gel (petroleum ether/dichloromethane gradient). The title product is obtained in the form of a powder.

¹H NMR: δ (400 MHz; dmso-d6; 300K): 7.84 (s, 1H NH); 7.17 (t, 2H aniline); 6.98 (d, 2H phenoxy); 6.94 (d, 2H aniline); 6.76 (d, 2H phenoxy); 6.72 (t, 1H aniline); 0.95 (s, 9H tert-butyl); 0.15 (s, 6H dimethyl)
IR: ν: >NH: 3403 cm⁻¹; >Ar: 1597 cm⁻¹

Preparation 9": 4-Benzyloxy-N-phenyl-aniline

To a solution of 4-hydroxy-N-phenyl-aniline (30 g; 162 mmol) in acetonitrile (400 mL) there are added 58 g of Cs₂CO₃ (178 mmol) and stirring is carried out for 15 minutes at ambient temperature. Benzyl bromide (22.5 mL; 178 mmol) is then added dropwise and then the reaction mixture is refluxed for 4 hours. After filtering and rinsing with acetonitrile, the filtrate is concentrated and chromatographed over silica gel (petroleum ether/AcOEt gradient). The title product is then obtained in the form of a colourless solid.

Preparation 10": N-(4-{[tert-Butyl(dimethyl)silyl]oxy}phenyl)-3-fluoro-4-[2-(morpholin-4-yl)ethoxy]aniline The procedure is in accordance with the process of Preparation 3", replacing the 5-bromo-1H-indole used in Step A by 4-bromo-2-fluorophenol.

¹H NMR: δ (400 MHz; dmso-d6; 300K): 7.75 (d, 1H); 7 (dd, 1H); 6.9 (d, 2H); 6.75 (m, 3H); 6.7 (ddd, 1H); 4.05 (t, 2H); 3.6 (t, 4H); 2.65 (t, 2H); 2.45 (t, 4H); 0.95 (s, 9H); 0.2 (s, 6H)

Preparation 11": N-(4-{[tert-Butyl(dimethyl)silyl]oxy}phenyl)pyridin-4-amine

The procedure is in accordance with the process of Preparation 1", replacing the 4-bromo-1-methyl-1H-pyrazole used in Step B with 4-bromopyridine.
IR: ν —NH—: 3200 and 2500 cm⁻¹; ν —Si—O—: 902 cm⁻¹; ν —Si—C—: 820 cm⁻¹

Preparation 12": 3-[(4-{[tert-Butyl(dimethyl)silyl]oxy}phenyl)amino]benzonitrile The procedure is in accordance with the process of Preparation 1", replacing the 4-bromo-1-methyl-1H-pyrazole used in Step B with 3-bromobenzonitrile.

Preparation 13": N-(4-{[tert-Butyl(dimethyl)silyl]oxy}phenyl)-3-fluoroaniline

The procedure is in accordance with the process of Preparation 1", replacing the 4-bromo-1-methyl-1H-pyrazole used in Step B with 1-bromo-3-fluorobenzene.

Preparation 14": N-(4-{[tert-Butyl(dimethyl)silyl]oxy}phenyl)-3,4-difluoroaniline The procedure is in accordance with the process of Preparation 1", replacing the 4-bromo-1-methyl-1H-pyrazole used in Step B with 4-bromo-1,2-difluorobenzene.

Preparation 15": 4-{[tert-Butyl(dimethyl)silyl]oxy}-N-{4-[(3,3-difluoropiperidin-1-yl)methyl]phenyl}aniline Step A: 1-(4-Bromobenzyl)-3,3-difluoropiperidine To a solution of 4-bromobenzaldehyde (500 mg; 2.7 mmol) in 12 mL of dichloromethane there are added, in the order stated, 3,3-difluoropiperidine hydrochloride (470 mg; 3 mmol), sodium triacetoxyborohydride (860 mg; 4 mmol) and acetic acid (0.17 mL; 3 mmol). After stirring for 1 hour at ambient temperature, the reaction mixture is poured over a mixture of aqueous sodium bicarbonate and dichloromethane. The aqueous phase is extracted with dichloromethane. The organic phase is dried over MgSO₄, concentrated to dryness and the residue is purified by chromatography over silica gel (CH₂Cl₂/MeOH gradient) to provide the expected product in the form of an oil.

¹H NMR: δ (400 MHz; dmso-d6; 300K): 7.55 (dd, 2H); 7.25 (dd, 2H); 3.55 (s, 2H); 2.7 (t, 2H); 2.35 (t, 2H); 1.85 (m, 2H); 1.65 (m, 2H)

Step B: 4-{[tert-Butyl(dimethyl)silyl]oxy}-N-{4-[(3,3-difluoropiperidin-1-yl)methyl]-phenyl}aniline The procedure is in accordance with the process of Preparation 1", replacing the 4-bromo-1-methyl-1H-pyrazole used in Step B with 1-[(4-bromophenyl)methyl]-3,3-difluoropiperidine.

Preparation 16": N-(4-{[tert-Butyl(dimethyl)silyl]oxy}phenyl)quinolin-6-amine

The procedure is in accordance with the process of Preparation 1", replacing the 4-bromo-1-methyl-1H-pyrazole used in Step B with 6-bromo-quinoline.
IR: ν —NH—: 3300 cm$^{-1}$ Preparation 17": N-(4-{[tert-Butyl(dimethyl)silyl]oxy}phenyl)-2-methylpyridin-4-amine The procedure is in accordance with the process of Preparation 1", replacing the 4-bromo-1-methyl-1H-pyrazole used in Step B with 4-bromo-2-methyl-pyridine.
IR: ν —NH—: 3200 and 3100 cm$^{-1}$ Preparation 18": N-(4-{[tert-Butyl(dimethyl)silyl]oxy}phenyl)-1-methyl-1H-pyrrolo[2,3-b]pyridin-5-amine The procedure is in accordance with the process of Preparation 1", replacing the 4-bromo-1-methyl-1H-pyrazole used in Step B with 5-bromo-1-methyl-1H-pyrrolo[2,3-b]pyridine (obtained in accordance with a protocol from the literature: Heterocycles, 60(4), 865, 2003).
IR: ν:—NH—: 3278 cm$^{-1}$; ν: aromatic —C═C— moieties: 1605 cm$^{-1}$ Preparation 19": N-(4-{[tert-Butyl(dimethyl)silyl]oxy}phenyl)pyridin-3-amine The procedure is in accordance with the process of Preparation 1", replacing the 4-bromo-1-methyl-1H-pyrazole used in Step B with 3-bromo-pyridine.

Preparation 20": 4-{[tert-Butyl(dimethyl)silyl]oxy}-N-{4-[(3,3-difluoropiperidin-1-yl)-ethyl]phenyl}aniline Step A: 2-(4-Bromophenyl)-1-(3,3-difluoropiperidin-1-yl)ethanone To a solution of 4-bromophenylacetic acid (4 g; 18.6 mmol) and 3,3-difluoropiperidine hydrochloride (2.5 g; 20.4 mmol) in dichloromethane (190 mL) there are added EDC (3.8 g; 22.3 mmol), HOBt (3 g; 22.3 mmol) and triethylamine (1.3 mL; 593 mmol). The reaction mixture is stirred for 17 hours at ambient temperature and is then poured over a mixture of aqueous sodium bicarbonate and ethyl acetate. The aqueous phase is extracted with ethyl acetate. The organic phase is washed with 0.1N hydrochloric acid, with water and with brine before being dried over MgSO$_4$ and concentrated to dryness. The residue is purified by chromatography over silica gel (petroleum ether/ethyl acetate gradient) to provide the expected product in the form of a solid.
$^1$H NMR: δ (400 MHz; dmso-d6; 300K): 7.5 (d, 2H); 7.2 (d, 2H); 3.8 (t, 2H); 3.7 (s, 3H); 3.5 (t, 2H); 2 (m, 2H); 1.6 (m, 2H)

Step B: 1-[2-(4-Bromophenyl)ethyl]-3,3-difluoropiperidine

To a solution of the compound of Step A (4.6 g; 14.5 mmol) in anhydrous THF (145 mL) there is added a 1M solution of borane dimethyl sulphide in THF (14.5 mL; 14.5 mmol). The reaction mixture is heated at 80° C. over 3 hours and then the solvent is evaporated off under reduced pressure. The residue is treated with methanol (50 mL) and then with 5N HCl (5.8 mL). After stirring overnight at ambient temperature and refluxing for 3 hours, the pH of the reaction mixture is adjusted to 8 with saturated sodium bicarbonate solution; the aqueous phase is then extracted with dichloromethane. The organic phase is dried over MgSO$_4$ and concentrated to dryness, and the residue is purified by chromatography over silica gel (CH$_2$Cl$_2$/MeOH gradient) to provide the expected product in the form of an oil.
$^1$H NMR: δ (400 MHz; dmso-d6; 300K): 7.45 (d, 2H); 7.20 (d, 2H); 2.71 (m, 2H); 2.69 (t, 2H); 2.58 (dd, 2H); 2.45 (dd, 2H); 1.86 (m, 2H); 1.63 (m, 2H)

Step C: 4-{[tert-Butyl(dimethyl)silyl]oxy}-N-{4-[(3,3-difluoropiperidin-1-yl)ethyl]-phenyl}aniline The procedure is in accordance with the process of Preparation 1", replacing the 4-bromo-1-methyl-1H-pyrazole used in Step B by the compound of Step B.
$^1$H NMR: δ (400 MHz; dmso-d6; 300K): 7.7 (s, 1H); 7.45 (d, 2H); 7.39 (t, 2H); 7.31 (t, 1H); 7.0 (m, 4H); 6.9 (d, 2H); 6.81 (d, 2H); 5.05 (s, 2H); 2.7 (t, 2H); 2.6 (t, 2H); 2.5 (t, 2H); 2.45 (t, 2H); 1.89 (m, 2H); 1.68 (m, 2H)

Preparation 21": 4-{[tert-Butyl(dimethyl)silyl]oxy}-N-{4-[2-(3,3-difluoropyrrolidin-1-yl)ethyl]phenyl}aniline The procedure is in accordance with the process of Preparation 19", replacing the 3,3-difluoropiperidine hydrochloride in Step A with 3,3-difluoropyrrolidine hydrochloride.
$^1$H NMR: δ (400 MHz; dmso-d6; 300K): 7.7 (s, 1H); 7.45 (d, 2H); 7.35 (t, 2H); 7.34 (t, 1H); 7.05-6.85 (m, 8H); 5.05 (s, 2H); 2.9 (t, 2H); 2.75-2.25 (m, 8H)

Preparation 22": N-(4-{[tert-Butyl(dimethyl)silyl]oxy}phenyl)-2,6-dimethylpyridin-4-amine The procedure is in accordance with the process of Preparation 1", replacing the 4-bromo-1-methyl-1H-pyrazole used in Step B with 4-bromo-2,6-dimethylpyridine.
IR: ν: —NH—: 3300 and 2700 cm$^{-1}$; ν:—Si—O—: 900 cm$^{-1}$; ν: —Si—C—: 823 cm$^{-1}$ Preparation 23": N-(4-{[tert-Butyl(dimethyl)silyl]oxy}phenyl)-1-[2-(morpholin-4-yl)-ethyl]-1H-pyrazol-4-amine The procedure is in accordance with the process of Preparation 2", replacing the 5-bromoindole used in Step A with 4-bromo-1H-pyrazole.
$^1$H NMR: δ (400 MHz; dmso-d6; 300K): 7.61 (s, 1H); 7.25 (s, 1H); 7.18 (s, 1H); 6.65 (m, 4H); 4.15 (t, 2H); 3.55 (t, 4H); 2.7 (t, 2H); 2.4 (t, 4H); 0.95 (s, 9H); 0.15 (s, 6h)

Preparation 24": N-(4-{[tert-Butyl(dimethyl)silyl]oxy}phenyl)-3-fluoropyridin-4-amine The procedure is in accordance with the process of Preparation 1", replacing the 4-bromo-1-methyl-1H-pyrazole used in Step B with 4-bromo-3-fluoro-pyridine.

IR: ν —NH—: 3200 and 3000 cm⁻¹; ν —Si—O—: 900 cm⁻¹; ν —Si—C—: 820 cm⁻¹

Preparation 25": N-(4-{[tert-Butyl(dimethyl)silyl]oxy}phenyl)imidazo[1,2-a]-pyridin-7-amine The procedure is in accordance with the process of Preparation 1", replacing the 4-bromo-1-methyl-1H-pyrazole used in Step B with 7-bromoimidazo[1,2-a]pyridine (prepared starting from 4-bromopyridin-2-amine in accordance with a protocol in the literature: WO 2008124323 A1).
IR: ν —NH—: 3300-3000 cm⁻¹; ν —C=N—: 1652 cm⁻¹; ν —C=C—: 1610 cm⁻¹; ν —Si—C—: 1236 cm⁻¹; ν —Si—O—: 898 cm⁻¹; ν —Si—C—: 828, 774 cm⁻¹

Preparation 26": N-(4-{[tert-Butyl(dimethyl)silyl]oxy}phenyl)-2-methyl-imidazo[1,2-a]pyridin-7-amine The procedure is in accordance with the process of Preparation 1", replacing the 4-bromo-1-methyl-1H-pyrazole used in Step B with 7-bromo-2-methyl-imidazo[1,2-a]pyridine (prepared starting from 4-bromopyridin-2-amine in accordance with a protocol in the literature: A. J. Helliot et al *J. Heterocyclic Chemistry* 19, 1437, 1982).
IR: ν —NH—: 3300-3000 cm⁻¹; ν —C=N—: 1652 cm⁻¹; ν —C=C—: 1610 cm⁻¹; ν —Si—C—: 1236 cm⁻¹; ν —Si—O—: 898 cm⁻¹; ν —Si—C—: 828, 774 cm⁻¹

Preparation 27": N-(4-{[tert-Butyl(dimethyl)silyl]oxy}phenyl)-6-methylpyridin-3-amine The procedure is in accordance with the process of Preparation 1", replacing the 4-bromo-1-methyl-1H-pyrazole used in Step B with 3-bromo-6-methyl-pyridine.
IR: ν —NH—: 3251 cm⁻¹; ν aromatic —C=C— moieties: 1605 cm⁻¹

Preparation 28": N-(4-{[tert-Butyl(dimethyl)silyl]oxy}phenyl)-5-fluoropyridin-3-amine The procedure is in accordance with the process of Preparation 1", replacing the 4-bromo-1-methyl-1H-pyrazole used in Step B with 3-bromo-5-fluoro-pyridine.
IR: ν —NH—: 3400-3000 cm⁻¹; ν —C—F—: 1245 cm⁻¹

Preparation 29": N-(4-{[tert-Butyl(dimethyl)silyl]oxy}phenyl)-2-methoxypyridin-4-amine The procedure is in accordance with the process of Preparation 1", replacing the 4-bromo-1-methyl-1H-pyrazole used in Step B with 4-bromo-2-methoxy-pyridine.
IR: ν —NH—: 3200 and 3000 cm⁻¹; ν aromatic —C=C— moieties: 1618, 1601 cm⁻¹

Preparation 30": N-(4-{[tert-Butyl(dimethyl)silyl]oxy}phenyl)-2-(propan-2-yl)pyridin-4-amine The procedure is in accordance with the process of Preparation 1", replacing the 4-bromo-1-methyl-1H-pyrazole used in Step B with 4-bromo-2-(propan-2-yl)pyridine.
IR: ν —NH—: 3300 and 3100 cm⁻¹

Preparation 31": N-(4-{[tert-Butyl(dimethyl)silyl]oxy}phenyl)pyrazolo[1,5-a]-pyrimidin-6-amine The procedure is in accordance with the process of Preparation 1", replacing the 4-bromo-1-methyl-1H-pyrazole used in Step B with 6-bromopyrazolo[1,5-a]pyrimidine.
IR: ν —NH—: 3272 cm⁻¹; ν —C=N—: 1634 cm⁻¹; ν —C=C—: 1616 cm⁻¹

Preparation 32": N-(4-{[tert-Butyl(dimethyl)silyl]oxy}phenyl)-3,3a-dihydro[1,2,4]triazolo[1,5-a]pyrimidin-6-amine The procedure is in accordance with the process of Preparation 1", replacing the 4-bromo-1-methyl-1H-pyrazole used in Step B with 6-bromo-3,3a-dihydro[1,2,4]triazolo[1,5-a]-pyrimidine prepared in accordance with the literature (WO 2011015343) starting from 4H-1,2,4-triazol-3-amine and 2-bromopropanedial.
IR: ν —NH—: 3244 cm⁻¹

Preparation 33": N-(4-{[tert-Butyl(dimethyl)silyl]oxy}phenyl)pyridin-4-amine 1-oxide The procedure is in accordance with the process of Preparation 1", replacing the 4-bromo-1-methyl-1H-pyrazole used in Step B with 4-bromopyridine 1-oxide prepared in accordance with the literature (WO 2009117269) starting from 4-bromopyridine.
IR: ν —NH—: 3246 cm⁻¹; ν aromatic —C=C— moieties: 1618 cm⁻¹
Mass Spectrum:
Empirical formula: $C_{17}H_{24}N_2O_2Si$
$[M]^+$. measured m/z: 316
$[M-O]^+$. measured m/z: 300
$[M-C_4H_9]^+$. measured m/z: 259

Preparation 34": N-[4-[tert-Butyl(dimethyl)silyl]oxyphenyl]-1-methyl-pyridin-1-ium-4-amine chloride The procedure is in accordance with the process of Preparation 1", replacing the 4-bromo-1-methyl-1H-pyrazole used in Step B with 4-bromo-1-methyl-pyridin-1-ium chloride prepared in accordance with the literature starting from 4-bromopyridine.

Preparation 35": N-[4-[tert-Butyl(dimethyl)silyl]oxyphenyl]-1-methyl-pyrazolo[3,4-b]pyridin-5-amine The procedure is in accordance with the process of Preparation 1", replacing the 4-bromo-1-methyl-1H-pyrazole used in Step B with 5-bromo-1-methyl-pyrazolo[3,4-b]pyridine prepared in accordance with the literature (WO 2006052568).
¹H NMR (400 MHz, dmso-d6) δ ppm: 8.33 (d, 1H), 7.94 (bs, 1H), 7.92 (s, 1H), 7.71 (d, 1H), 6.95 (d, 2H), 6.76 (d, 2H), 4.01 (s, 3H), 0.95 (s, 9H), 0.17 (s, 6H)
IR (ATR) cm⁻¹: 3290 ν>OH; 1503 ν Ar; 1249 γ —Si—CH₃

Preparation 36": N-[4-[tert-Butyl(dimethyl)silyl]oxyphenyl]-3-methyl-pyrazolo[1,5-a]pyrimidin-6-amine The procedure is in accordance with the process of Preparation 1", replacing the 4-bromo-1-methyl-1H-pyrazole used in Step B with 6-bromo-3-methyl-pyrazolo[1,5-a]pyrimidine prepared in accordance with the literature (WO 2011015343 and WO2011049917).

¹H NMR (400 MHz, dmso-d6) δ ppm: 8.49 (d, 1H), 8.4 (d, 1H), 7.98 (m, 1H), 7.87 (s, 1H), 7 (d, 2H), 6.81 (d, 2H), 2.29 (s, 3H), 0.98 (s, 9H), 0.2 (s, 6H)

IR (ATR) cm⁻¹: 3257 ν>NH

The amines NHR₃R₄ wherein R₃ and R₄, each independently of the other, represent an aryl or heteroaryl group are obtained in accordance with processes described in the literature (Surry D. S. et al., *Chemical Science*, 2011, 2, 27-50, Charles M. D. et al., *Organic Letters*, 2005, 7, 3965-3968). The reaction protecting the hydroxy function of the 4-anilinophenol described in Preparation 8″ can be applied to various secondary amines NHR₃R₄ (as defined hereinbefore) having one or more hydroxy functions, when they are available commercially. Alternatively, the secondary amines having at least one hydroxy substituent may be synthesised directly in a protected form, i.e. starting from reagents whose hydroxy function has been protected beforehand. Among the protecting groups, tert-butyl(dimethyl)silyloxy and benzyloxy are especially preferred.

Among the amines NHR₃R₄ having a hydroxy substituent that are used for synthesising the compounds of the invention there may be mentioned: 4-(4-toluidino)phenol, 4-(4-chloroanilino)phenol, 4-(3-fluoro-4-methylanilino)phenol, 4-[4-(trifluoromethoxy)anilino]-phenol, 4-[4-hydroxyanilino]phenol, {4-[(1-methyl-1H-indol-6-yl)amino]phenyl}-methanol, 4-(2,3-dihydro-1H-indol-6-ylamino)phenol, 4-[(1-methyl-2,3-dihydro-1H-indol-6-yl)amino]phenol, 4-[(1-methyl-1H-indol-6-yl)amino]phenol, 4-[(1-methyl-1H-indol-6-yl)amino]cyclohexanol, 4-[(1-methyl-1,2,3,4-tetrahydro-6-quinolinyl)amino]phenol, 4-[(4-methyl-3,4-dihydro-2H-1,4-benzoxazin-7-yl)amino]phenol, 4-[4-(diethylamino)anilino]-phenol, 4-(2,3-dihydro-1H-inden-5-ylamino)phenol, 4-[(1-methyl-1H-indazol-5-yl)amino]-phenol, 4-[(1'-methyl-1',2'-dihydrospiro[cyclopropane-1,3'-indol]-5'-yl)amino]phenol, 4-[(1,3,3-trimethyl-2,3-dihydro-1H-indol-5-yl)amino]phenol, 4-[4-methoxy-3-(trifluoromethyl)anilino]phenol, 4-[4-(methylsulphanyl)-3-(trifluoromethyl)anilino]phenol, 2-fluoro-4-[(1-methyl-1H-indol-5-yl)amino]phenol, 4-[(1-ethyl-1H-indol-5-yl)amino] phenol, 4-[(1-ethyl-2,3-dihydro-1H-indol-5-yl)amino] phenol, 4-[(1-isopropyl-2,3-dihydro-1H-indol-5-yl)amino] phenol, 4-(butylamino)phenol, 3-[(1-methyl-1H-indol-5-yl)amino]-1-propanol, 4-[(1-methyl-1H-indol-5-yl)amino]-1-butanol, 4-[(3-fluoro-4-methylphenyl)-amino]phenol, 4-[(3-chloro-4-methylphenyl)amino]phenol, 4-[(4-fluorophenyl)amino]-phenol, 4-[(1-methyl-1H-pyrrolo[2,3-b]pyridin-5-yl)amino]phenol, 4-[(4-fluorophenyl)-amino]phenol, 4-[(2-fluorophenyl)amino]phenol, 4-[(3-fluorophenyl)amino] phenol, 4-[(2,4-difluorophenyl)amino]phenol, 4-[(3,4-difluorophenyl)amino]phenol, 3-[(4-hydroxy-phenyl) amino]benzonitrile, 4-[(3-methoxyphenyl)amino]phenol, 4-[(3,5-difluorophenyl)-amino]phenol, 4-[(3-methylphenyl) amino]phenol, 4-[(4-hydroxyphenyl)amino]benzonitrile, 4-[(3-chlorophenyl)amino]phenol, 4-(pyrimidin-2-ylamino) phenol, 4-[(cyclobutyl-methyl)amino]phenol, 2-[(4-hydroxyphenyl)amino]benzonitrile, 4-{[(1-methyl-1H-pyrazol-4-yl)methyl]amino}phenol, 4-[(cyclopropylmethyl) amino]phenol, 4-{[(1-methyl-1H-pyrazol-3-yl)methyl] amino}phenol, 4-(but-2-yn-1-ylamino)phenol, 4-(pyrazin-2-yl-amino)phenol, 4-(pyridin-2-ylamino)phenol, 4-(pyridazin-3-ylamino)phenol, 4-(pyrimidin-5-ylamino) phenol, 4-(pyridin-3-ylamino)phenol, 4-[(3,5-difluoro-4-methoxyphenyl)-amino]phenol, 4-(pyridin-4-ylamino)phenol, 4-[(3-fluoro-4-methoxyphenyl)amino]phenol, 2-(phenylamino)pyrimidin-5-ol, 5-[(4-hydroxyphenyl) amino]-2-methoxybenzonitrile, 4-{[3-(trifluoromethyl)phenyl]amino}phenol, 4-(methylamino)phenol, 4-(ethylamino) phenol and 4-(propan-2-ylamino)phenol.

The hydroxy function(s) of the secondary amines listed above is (are) protected beforehand by a suitable protecting group prior to any coupling to an acid derivative of the compound of formula (VII) as defined in the preceding general process.

EXAMPLE 1

N-(4-Hydroxyphenyl)-3-(6-{[(3R)-3-methyl-3,4-dihydroisoquinolin-2(1H)-yl]carbonyl}-1,3-benzodioxol-5-yl)-N-(1-methyl-1H-indol-5-yl)-5,6,7,8-tetrahydroindolizine-1-carboxamide Step A: Methyl 3-(6-{[(3R)-3-methyl-3,4-dihydroisoquinolin-2(1H)-yl]carbonyl}-1,3-benzodioxol-5-yl)-5,6,7,8-tetrahydroindolizine-1-carboxylate To a solution of 2 g of the compound of Preparation 1 in 20 mL of dichloromethane there are added, at ambient temperature, 5.5 mL of N,N,N-triethylamine (6.96 mmol), the compound of Preparation 1' (6.96 mmol), and then 0.94 g of hydroxybenzotriazole (HOBT) and 1.34 g of 1-ethyl-3-(3'-dimethylaminopropyl)-carbodiimide (EDC) (6.96 mmol). The reaction mixture is then stirred at ambient temperature overnight; it is then poured onto a solution of ammonium chloride and extracted with ethyl acetate. The organic phase is then dried over magnesium sulphate, and then filtered and evaporated to dryness. The crude product thereby obtained is then purified by chromatography over silica gel (heptane/AcOEt gradient) to yield the expected product.

¹H NMR: δ (400 MHz; dmso-d6; 300K): 7.2-6.8 (m, 4H, aromatic Hs, H tetrahydroisoquinoline); 7.10 (s, 1H, aromatic H, benzodioxole); 6.92 (s, 1H, aromatic H, benzodioxole); 6.25 (m, 1H, H tetrahydroindolizine); 6.10 (s, 2H, aliphatic Hs, OCH₂O); 4.80 (m, 1H, aliphatic H, H tetrahydroisoquinoline); 4.20 (m, 1H, aliphatic H, H tetrahydroisoquinoline); 4.1-3.5 (m, 3H); 3.60 (s, 3H, COOCH₃); 2.90 (m, 2H, aliphatic Hs, H tetrahydroindolizine); 2.45 (m, 2H, aliphatic Hs, H tetrahydroisoquinoline); 1.70 (m, 4H, aliphatic Hs, H tetrahydroindolizine); 0.80 (m, 3H, aliphatic Hs, CH₃-THIQ).

IR: ν: >C=O 1694 cm⁻¹ (conjugated ester); ν: >C=O 1624 cm⁻¹ (amide); ν: >C—Ar 772-742 cm⁻¹

Step B: Lithium 3-(6-{[(3R)-3-methyl-3,4-dihydroisoquinolin-2(1H)-yl]carbonyl}-1,3-benzodioxol-5-yl)-5, 6,7,8-tetrahydroindolizine-1-carboxylate To a solution containing 8.26 mmol of the compound of Step A in 24 mL of dioxane there is added a solution of lithium hydroxide (675 mg, 16.1 mmol). The batch is placed in a microwave oven at 140 W, 100° C. for a period of 2 hours 30 minutes. The reaction mixture is then filtered and evaporated. The solid thereby obtained is dried at 40° C. in an oven in the presence of P₂O₅.

Step C: N-(4-{[tert-Butyl(dimethyl)silyl]oxy}phenyl)-3-(6-{[(3R)-3-methyl-3,4-dihydroisoquinolin-2(1H)-yl]carbonyl}-1,3-benzodioxol-5-yl)-N-(1-methyl-1H-indol-5-yl)-5, 6, 7,8-tetrahydroindolizine-1-carboxamide To a solution containing 4.73 mmol of the compound of Step B in 47 mL of dichloromethane there are added, dropwise, 1.2 mL of oxalyl chloride at 0° C. The reaction mixture is stirred at ambient temperature for 11 hours and is then co-evaporated several times with dichloromethane. The product thereby obtained is suspended in 37 mL of dichloromethane and is then added to a solution containing 7.1 mmol of the compound obtained in Preparation 2" in 10 mL of dichloromethane in the presence of 0.6 mL of pyridine (7.1 mmol). The batch is stirred at ambient temperature overnight. The reaction mixture is concentrated, purified by chromatography over silica gel (dichloromethane/methanol gradient) to yield the expected product.

Step D: N-(4-Hydroxyphenyl)-3-(6-{[(3R)-3-methyl-3,4-dihydroisoquinolin-2(1H)-yl]-carbonyl}-1,3-benzodioxol-5-yl)-N-(1-methyl-H-indol-5-yl)-5,6,7,8-tetrahydroindolizine-1-carboxamide To a solution containing 2.3 mmol of the compound obtained in Step C in 4 mL of methanol there is added 0.646 g (11.5 mmol) of potassium hydroxide dissolved in 8 mL of methanol. The batch is stirred at ambient temperature for 30 minutes. The reaction mixture is then diluted with dichloromethane and washed successively with 1N HCl solution, saturated NaHCO$_3$ solution and then saturated NaCl solution until a neutral pH is obtained. The organic phase is then dried over magnesium sulphate, filtered and evaporated. The crude product thereby obtained is purified over silica gel (dichloromethane/methanol gradient) and then lyophilised to provide the expected product.

High-Resolution Mass Spectroscopy (ESI+):

Empirical formula: $C_{42}H_{38}CN_4O_5$

[M+H]$^+$, calculated: 679.2920

[M+H]$^+$, measured: 679.2908

EXAMPLE 2

N-(4-Hydroxyphenyl)-3-(6-{[(3R)-3-methyl-3,4-dihydroisoquinolin-2(1H)-yl]carbonyl}-1,3-benzodioxol-5-yl)-N-{1-[2-(morpholin-4-yl)ethyl]-1H-indol-5-yl}-5,6,7,8-tetrahydroindolizine-1-carboxamide hydrochloride The procedure is in accordance with the processes described in Steps A-D of Example 1 using the appropriate reagents. After the step of purification over silica gel (cf. Step D), the solid is then dissolved in dichloromethane and 2 mL of 1N HCl in ether are added. The entire batch is stirred for 1 hour and then evaporated to dryness. The hydrochloride thereby obtained is dissolved in a mixture of water/acetonitrile until dissolution is complete and is then lyophilised.

Elemental Microanalysis: (%, Theoretical:Measured)

% C=69.32:68.93; % H=5.94:5.74; % N=8.6:8.51; % Cl—=4.35:4.6

Unless otherwise mentioned, the compounds of the following Examples are synthesised in accordance with the process of Example 1 using, in Step A: (i) the appropriate acid obtained according to one of Preparations 1 to 18 and (ii) the appropriate tetrahydroisoquinoline compound obtained according to one of Preparations 1' to 7' and, in Step C: (iii) the suitable NHR$_3$R$_4$ amine (a non-exhaustive list is proposed in Preparations 1" to 36").

EXAMPLE 3

6-(5-Chloro-2-{[(3R)-3-methyl-3,4-dihydroisoquinolin-2(1H)-yl]-carbonyl}phenyl)-N-(4-hydroxyphenyl)-N-(1-methyl-1H-indol-5-yl)-1,2,3,4-tetrahydropyrrolo[1,2-a]pyrazine-8-carboxamide hydrochloride The procedure is in accordance with the process of Example 1, replacing, on the one hand, the compound of Preparation 1 used in Step A with the compound of Preparation 2 and, on the other hand, the compound of Preparation 1" used in Step C with N-(4-{[tert-butyl(dimethyl)silyl]oxy}phenyl)-1-methyl-1H-indol-5-amine, it being understood that the product thereby obtained is not subjected to a step of conversion into a salt in the presence of HCl in ether as is described in Step D of Example 1. The compound thereby obtained is deprotected in the presence of 10 equivalents of trifluoroacetic acid in dichloromethane (10 mL/mmol) at ambient temperature overnight. The product is then isolated by concentrating the reaction mixture to dryness. Finally, it is subjected to a step of conversion into a salt in the presence of HCl in ether.

Elemental Microanalysis: (%, Theoretical:Measured)

% C=67.99:65.52; % H=5.28:4.49; % N=9.91:9.24; % Cl=10.03:9.95; % Cl—=5.02:5.45

High-Resolution Mass Spectroscopy (ESI+):

Empirical formula: $C_{40}H_{36}ClN_5O_3$

[M+H]$^+$, calculated: 670.2585

[M+H]$^+$, measured: 670.2587

EXAMPLE 4

3-[5-Chloro-2-(3,4-dihydroisoquinolin-2(1H)-ylcarbonyl)phenyl]-N-(4-hydroxyphenyl)-N-{1-[2-(morpholin-4-yl)ethyl]-1H-indol-5-yl}-5,6,7,8-tetrahydroindolizine-1-carboxamide Elemental Microanalysis: % Measured (Theoretical)

% C=70.85 (71.65); % H=5.39 (5.88); % N=9.11 (9.28); % Cl=4.48 (4.7)

EXAMPLE 5

3-[5-Chloro-2-(3,4-dihydroisoquinolin-2(1H)-ylcarbonyl)phenyl]-N-(4-hydroxyphenyl)-N-{1-[2-(morpholin-4-yl)ethyl]-2,3-dihydro-1H-indol-5-yl}-5,6,7,8-tetrahydroindolizine-1-carboxamide Step A: N-(4-{[tert-Butyl(dimethyl)silyl]oxy}phenyl)-3-[5-chloro-2-(3,4-dihydroisoquinolin-2(1H)-ylcarbonyl)phenyl]-N—{1-[2-(morpholin-4-yl)ethyl]-2,3-dihydro-1H-indol-5-yl}-5,6,7,8-tetrahydroindolizine-1-carboxamide The procedure is in accordance with the protocols described in Steps A-C of Example 1 using the compound of Preparation 3 and 1,2,3,4-tetrahydroisoquinoline in Step A, and the compound of Preparation 4" in Step C.

Step B: 3-[5-Chloro-2-(3,4-dihydroisoquinolin-2(1H)-ylcarbonyl)phenyl]-N-(4-hydroxy-phenyl)-N-{1-[2-(morpholin-4-yl)ethyl]-2,3-dihydro-H-indol-5-yl}-5, 6,7,8-tetrahydroindolizine-1-carboxamide To a solution of 1.3 g (1.45 mmol) of the compound of Step A in 13 mL of acetic acid there is added, at ambient temperature, sodium cyanoborohydride (900 mg; 15 mmol). After stirring for 2 hours, the reaction mixture is concentrated to dryness, and then diluted with methanol (8 mL) and treated with a 1M solution of potassium hydroxide in methanol (6.3 mL; 6.3 mmol). After 1 hour at ambient temperature, the reaction mixture is concentrated to dryness, and then chromatographed over silica gel (dichloromethane/methanol gradient) and then lyophilised to provide the expected product in the form of a powder.

Elemental Microanalysis: % Measured (Theoretical)

% C=70.74 (71.46); % H=5.74 (6.13); % N=9 (9.26); % Cl=4.46 (4.69)

EXAMPLE 6

N-(4-Hydroxyphenyl)-2-methyl-6-(7-{[(3R)-3-methyl-3,4-dihydroisoquinolin-2(1H)-yl]carbonyl}-2,3-dihydro-1,4-benzodioxin-6-yl)-N-(1-methyl-1H-indol-5-yl)-1,2,3,4-tetrahydropyrrolo[1,2-a]pyrazine-8-carboxamide hydrochloride The procedure is analogous to that described for Example 7, in Step A substituting the compound of Preparation 2 with the compound of Preparation 4.

Elemental Microanalysis: (%, Theoretical:Measured)

% C=69.39:69.13; % H=5.69:4.98; % N=9.41:9.37; % Cl—=4.76:4.65

EXAMPLE 7

6-(5-Chloro-2-{[(3R)-3-methyl-3,4-dihydroisoquinolin-2(1H)-yl]-carbonyl}phenyl)-N-(4-hydroxyphenyl)-2-methyl-N-(1-methyl-1H-indol-5-yl)-1,2,3,4-tetrahydropyrrolo[1,2-a]pyrazine-8-carboxamide Step A: tert-Butyl 8-[(4-{[tert-butyl(dimethyl)silyl]oxy}phenyl)(1-methyl-1H-indol-5-yl)-carbamoyl]-6-(5-chloro-2-{[(3R)-3-methyl-3,4-dihydroisoquinolin-2(1H)-yl]carbonyl}-phenyl)-3,4-dihydropyrrolo[1,2-a]pyrazine-2(1H)-carboxylate The procedure is in accordance with the protocols described in Steps A-C of Example 1 using the compounds of Preparations 2 and 1' in Step A, and the compound of Preparation 2" in Step C.

Step B: tert-Butyl 6-(5-chloro-2-{[(3R)-3-methyl-3,4-dihydroisoquinolin-2(1H)-yl]-carbonyl}phenyl)-8-[(4-hydroxyphenyl)(1-methyl-1H-indol-5-yl)carbamoyl]-3,4-dihydropyrrolo[1,2-a]pyrazine-2(1H)-carboxylate To a solution of the compound of Step A (1.1 g; 1.25 mmol) in methanol (6 mL) there is added a 1M solution of potassium hydroxide in methanol (6.2 mL; 6.2 mmol). After 2 hours at ambient temperature, the methanol is evaporated off in vacuo and the residue is taken up in a mixture composed of dichloromethane and saturated sodium bicarbonate solution. The combined organic phases are dried over $MgSO_4$ and concentrated to dryness. The residue obtained is purified by chromatography over silica gel ($CH_2Cl_2$/MeOH gradient) to provide the expected product in the form of a solid.

IR: ν: NH: 3450 cm$^{-1}$; ν: CO: 1745-1620 cm$^{-1}$

Step C: tert-Butyl 6-(5-chloro-2-{[(3R)-3-methyl-3,4-dihydroisoquinolin-2(1H)-yl]-carbonyl}phenyl)-8-[{4-[(2,2-dimethylpropanoyl)oxy]phenyl}(1-methyl-1H-indol-5-yl)carbamoyl]-3,4-dihydropyrrolo[1,2-a]pyrazine-2(1H)-carboxylate To a solution of the compound of Step B (0.7 g; 0.93 mmol) in dichloromethane (7 mL) there are added, at ambient temperature, triethylamine (0.2 mL; 1.39 mmol) and then pivaloyl chloride (0.11 mL; 0.93 mmol). After stirring for 2 hours at ambient temperature, the reaction mixture is washed with water and with brine, dried over $MgSO_4$ and concentrated to dryness. The residue obtained is used as is in the next Step without being analysed.

Step D: 2,2-Dimethyl 4-[{[6-(5-chloro-2-{[(3R)-3-methyl-3,4-dihydroisoquinolin-2(1H)-yl]carbonyl}phenyl)-1,2,3,4-tetrahydropyrrolo[1,2-a]pyrazin-8-yl]carbonyl}(1-methyl-1H-indol-5-yl)amino]phenyl propanoate To a solution of the compound of the preceding Step (0.82 g; 0.93 mmol) in dichloromethane (9 mL) there is added, at 0° C., trifluoroacetic acid (0.7 mL; 13.9 mmol) dropwise. After stirring for 15 hours at ambient temperature, saturated sodium bicarbonate solution is slowly added to the reaction mixture and then the phases are separated. The aqueous phase is extracted with dichloromethane. The combined organic phases are dried over $MgSO_4$ and concentrated to dryness. The residue obtained is purified by chromatography over silica gel ($CH_2Cl_2$/MeOH gradient) to provide the expected product in the form of a solid.

LC/MS: m/z=[M+H]$^+$=754.30

Step E: 2,2-Dimethyl 4-[{[6-(5-chloro-2-{[(3R)-3-methyl-3,4-dihydroisoquinolin-2(1H)-yl]carbonyl}phenyl)-2-methyl-1,2,3,4-tetrahydropyrrolo[1,2-a]pyrazin-8-yl]carbonyl}(1-methyl-1H-indol-5-yl)amino]phenyl propanoate To a solution of the compound of the preceding Step (0.41 g; 0.54 mmol) in dichloromethane (2 mL) there are added, at ambient temperature, formaldehyde (48 μL; 1.74 mmol) and then sodium triacetoxyborohydride (161 mg; 0.76 mmol). After stirring for 2 hours at ambient temperature, the reaction mixture is diluted with dichloromethane and then washed with saturated sodium bicarbonate solution. The organic phase is dried over $MgSO_4$ and concentrated to dryness. The residue obtained is purified by chromatography over silica gel ($CH_2Cl_2$/MeOH gradient). The expected product is obtained in the form of a solid.

LC/MS: m/z=[M+H]$^+$=768.32

Step F: 6-(5-Chloro-2-{[(3R)-3-methyl-3,4-dihydroisoquinolin-2(1H)-yl]carbonyl}-phenyl)-N-(4-hydroxyphenyl)-2-methyl-N-(1-methyl-1H-indol-5-yl)-1,2,3,4-tetrahydropyrrolo[1,2-a]pyrazine-8-carboxamide To a solution of the compound of the preceding Step (0.25 g; 0.32 mmol) in dioxane (1 mL) there is added a solution of lithium hydroxide (27 mg; 0.65 mmol) in water (1 mL). After stirring for 5 hours at ambient temperature, the reaction mixture is concentrated and diluted with saturated sodium bicarbonate solution. The aqueous phase is extracted with CH$_2$Cl$_2$. The organic phase is dried over MgSO$_4$ and concentrated to dryness. The residue obtained is purified by chromatography over silica gel (CH$_2$Cl$_2$/MeOH gradient). The expected product is then obtained in the form of a solid.

Elemental Microanalysis: (%, Theoretical:Measured)
% C=71.97:71.51; % H=5.6:5.25; % N=10.24:10.12

EXAMPLE 8

3-(5-Chloro-2-{[(3R)-3-methyl-3,4-dihydroisoquinolin-2(1H)-yl]-carbonyl}phenyl)-N-(4-hydroxyphenyl)-N-{1-[2-(morpholin-4-yl)ethyl]-1H-indol-5-yl}indolizine-1-carboxamide hydrochloride Elemental Microanalysis: (%, Theoretical:Measured)
% C=69:69.16; % H=5.41:4.82; % N=8.75:8.69; % Cl—=4.43:4.13

EXAMPLE 9

6-(5-Fluoro-2-{[(3R)-3-methyl-3,4-dihydroisoquinolin-2(1H)-yl]carbonyl}-phenyl)-N-(4-fluorophenyl)-N-(4-hydroxyphenyl)-1,2,3,4-tetrahydropyrrolo[1,2-a]-pyrazine-8-carboxamide hydrochloride The procedure is in accordance with the process of Example 1, replacing, on the one hand, the compound of Preparation 1 used in Step A with the compound of Preparation 6 and, on the other hand, the compound of Preparation 1″ used in Step C with the compound of Preparation 5″, it being understood that the product thereby obtained is not subjected to a step of conversion into a salt in the presence of HCl in ether as is described in Step D of Example 1. The compound thereby obtained is deprotected in the presence of 10 equivalents of trifluoroacetic acid in dichloromethane (10 mL/mmol) at ambient temperature overnight. The product is then isolated by concentrating the reaction mixture to dryness. Finally, it is subjected to a step of conversion into a salt in the presence of HCl in ether.

Elemental Microanalysis: (%, Theoretical:Measured)
% C=67.83:67.41; % H=5.08:4.61; % N=8.55:8.39; % Cl—=5.41:5.28

EXAMPLE 10

6-(5-Fluoro-2-{[(3R)-3-methyl-3,4-dihydroisoquinolin-2(1H)-yl]-carbonyl}phenyl)-N-(3-fluoro-4-methylphenyl)-N-(4-hydroxyphenyl)-1,2,3,4-tetrahydropyrrolo[1,2-a]pyrazine-8-carboxamide hydrochloride The procedure is in accordance with the process of Example 1, replacing, on the one hand, the compound of Preparation 1 used in Step A with the compound of Preparation 6 and, on the other hand, the compound of Preparation 1″ used in Step C with the compound of Preparation 6″, it being understood that the product thereby obtained is not subjected to a step of conversion into a salt in the presence of HCl in ether as is described in Step D of Example 1. The compound thereby obtained is deprotected in the presence of 10 equivalents of trifluoroacetic acid in dichloromethane (10 mL/mmol) at ambient temperature overnight. The product is then isolated by concentrating the reaction mixture to dryness. Finally, it is subjected to a step of conversion into a salt in the presence of HCl in ether.

Elemental Microanalysis: (%, Theoretical:Measured)
% C=68.21:68.29; % H=5.27:4.91; % N=8.37:8.34; % Cl—=5.3:5.17

EXAMPLE 11

N-(4-Hydroxyphenyl)-6-(6-{[(3R)-3-methyl-3,4-dihydroisoquinolin-2(1H)-yl]carbonyl}-1,3-benzodioxol-5-yl)-N-(1-methyl-1H-indazol-5-yl)-1,2,3,4-tetrahydropyrrolo[1,2-a]pyrazine-8-carboxamide hydrochloride The procedure is in accordance with the process of Example 1, replacing, on the one hand, the compound of Preparation 1 used in Step A with the compound of Preparation 7 and, on the other hand, the compound of Preparation 1″ used in Step C with N-(4-{[tert-butyl(dimethyl)silyl]oxy}phenyl)-1-methyl-1H-indazol-5-amine, it being understood that the product thereby obtained is not subjected to a step of conversion into a salt in the presence of HCl in ether as is described in Step D of Example 1. The compound thereby obtained is deprotected in the presence of 10 equivalents of trifluoroacetic acid in dichloromethane (10 mL/mmol) at ambient temperature overnight. The product is then isolated by concentrating the reaction mixture to dryness. Finally, it is subjected to a step of conversion into a salt in the presence of HCl in ether.

Elemental Microanalysis: (%, Theoretical:Measured)
% H=5.2:4.83; % N=11.72:11.64; % Cl—=4.94:5.34; % C=66.99:66.19

EXAMPLE 12

6-(5-Chloro-2-{[(3R)-3-methyl-3,4-dihydroisoquinolin-2(1H)-yl]-carbonyl}phenyl)-N-(4-hydroxyphenyl)-N-(1-methyl-1H-indazol-5-yl)-1,2,3,4-tetrahydropyrrolo[1,2-a]pyrazine-8-carboxamide hydrochloride The procedure is in accordance with the process of Example 1, replacing, on the one hand, the compound of Preparation 1 used in Step A with the compound of Preparation 2 and, on the other hand, the compound of Preparation 1″ used in Step C with N-(4-{[tert-butyl(dimethyl)silyl]oxy}phenyl)-1-methyl-1H-indazol-5-amine, it being understood that the product thereby obtained is not subjected to a step of conversion into a salt in the presence of HCl in ether as is described in Step D of Example 1. The compound thereby obtained is deprotected in the presence of 10 equivalents of trifluoroacetic acid in dichloromethane (10 mL/mmol) at ambient temperature overnight. The product is then isolated by concentrating the reaction mixture to dryness. Finally, it is subjected to a step of conversion into a salt in the presence of HCl in ether.

Elemental Microanalysis: (%, Theoretical:Measured)
% C=66.19:65.83; % H=5.13:4.99; % N=11.88:11.85; % Cl—=5.01:5.36

EXAMPLE 13

N-(4-Hydroxyphenyl)-3-(6-{[(3S)-3-[2-(morpholin-4-yl)ethyl]-3,4-dihydroisoquinolin-2(1H)-yl]carbonyl}-1,3-benzodioxol-5-yl)-N-phenyl-5,6,7,8-tetrahydroindolizine-1-carboxamide hydrochloride Elemental Microanalysis: (%, Theoretical:Measured)
% C=69.42:69.47; % H=5.96:5.58; % N=7.36:7.36; % Cl—=4.66:4.42

EXAMPLE 14

N-(4-Hydroxyphenyl)-N-(1-methyl-1H-indazol-5-yl)-3-(6-{[(3S)-3-[2-(morpholin-4-yl)ethyl]-3,4-dihydroisoquinolin-2(1H)-yl]carbonyl}-1,3-benzodioxol-5-yl)-5,6,7,8-tetrahydroindolizine-1-carboxamide hydrochloride Elemental Microanalysis: (%, Theoretical:Measured)
% C=67.76:67.81; % H=5.81:5.63; % N=10.31:10.13; % Cl—=4.35:4.22

EXAMPLE 15

7-Amino-N-(4-hydroxyphenyl)-3-(6-{[(3R)-3-methyl-3,4-dihydroisoquinolin-2(1H)-yl]carbonyl}-1,3-benzodioxol-5-yl)-N-phenyl-5,6,7,8-tetrahydroindolizine-1-carboxamide hydrochloride Step A: Methyl 3'-(6-{[(3R)-3-methyl-3,4-dihydroisoquinolin-2(1H)-yl]carbonyl}-1,3-benzodioxol-5-yl)-5',6'-dihydro-8'H-spiro[1,3-dioxolane-2, 7'-indolizine]-1'-carboxylate The procedure is in accordance with the protocol of Step A of Example 1, replacing the compound of Preparation 1 with the compound of Preparation 8.

Step B: Methyl 3-(6-{[(3R)-3-methyl-3,4-dihydroisoquinolin-2(1H)-yl]carbonyl}-1,3-benzodioxol-5-yl)-7-oxo-5,6,7,8-tetrahydroindolizine-1-carboxylate 4.47 mmol of the compound of Step A dissolved in 75 mL of THF are stirred in the presence of 37 mL of 1M HCl at reflux for 15 hours. 100 mL of water and 100 mL of ethyl acetate are added to the reaction mixture. There are then added 4 g of NaHCO$_3$ (4.7 mmol) in the form of a powder until a basic pH is obtained. The compound is extracted with ethyl acetate; the organic phase is dried over MgSO$_4$, filtered and concentrated to dryness.

Step C: Methyl 7-hydroxy-3-(6-{[(3R)-3-methyl-3,4-dihydroisoquinolin-2(1H)-yl]-carbonyl}-1,3-benzodioxol-5-yl)-5, 6, 7,8-tetrahydroindolizine-1-carboxylate To a solution of 4.47 mmol of the compound obtained in Step B in 30 mL of methanol there are added, in portions, 558 mg (14.75 mmol) of sodium borohydride. The reaction mixture is stirred for 1 hour at ambient temperature. 50 mL of 1M HCl are then added and the methanol is evaporated off. The aqueous phase is then neutralised using NaHCO$_3$ and then extracted with dichloromethane. The organic phase is successively washed with H$_2$O, dried over MgSO$_4$, filtered and concentrated to dryness. The oil thereby obtained is purified by flash chromatography (dichloromethane/ethanol-ammonia gradient) to yield the expected product.

Step D: Methyl 3-(6-{[(3R)-3-methyl-3,4-dihydroisoquinolin-2(1H)-yl]carbonyl}-1,3-benzodioxol-5-yl)-7-(prop-2-en-1-yloxy)-5,6,7,8-tetrahydroindolizine-1-carboxylate To a suspension of 331 mg (8.26 mmol) of sodium hydride in 15 mL of anhydrous THF cooled to 0° C. there are added 4.13 mmol of the compound obtained in Step C. The resulting suspension is stirred for 15 minutes at 0° C. and then a solution of 790 µL (9.1 mmol) of allyl bromide in 10 mL of THF is slowly added (over 15 minutes). The reaction mixture is stirred for 1 hour at 0° C., and then for 15 hours at ambient temperature. The resulting solution is hydrolysed with saturated aqueous NH$_4$Cl solution. The compound is extracted with ethyl acetate; the organic phase is dried over MgSO$_4$, filtered and concentrated to dryness. The oil thereby obtained is purified by flash chromatography (cyclohexane/ethyl acetate gradient) to yield the expected product.

Step E: N-(4-{[tert-Butyl(dimethyl)silyl]oxy}phenyl)-3-(6-{[(3R)-3-methyl-3,4-dihydroisoquinolin-2(1H)-yl]carbonyl}-1,3-benzodioxol-5-yl)-N-phenyl-7-(prop-2-en-1-yloxy)-5,6,7,8-tetrahydroindolizine-1-carboxamide The procedure is in accordance with the processes described in Steps B and C of Example 1 using the appropriate reagents.

Step F: N-(4-{[tert-Butyl(dimethyl)silyl]oxy}phenyl)-7-hydroxy-3-(6-{[(3R)-3-methyl-3,4-dihydroisoquinolin-2(H)-yl]carbonyl}-1,3-benzodioxol-5-yl)-N-phenyl-5,6,7,8-tetrahydroindolizine-1-carboxamide There is then carried out a reaction deprotecting the allyl group in the presence of 1,3-dimethylpyrimidine-2,4,6(1H, 3H,5H)-trione (also called dimethylbarbiturate) and tetrakis(triphenylphosphine)palladium in a mixture of methanol and dichloromethane.

Step G: 7-Azido-N-(4-{[tert-butyl(dimethyl)silyl]oxy}phenyl)-3-(6-{[(3R)-3-methyl-3,4-dihydroisoquinolin-2(1H)-yl]carbonyl}-1,3-benzodioxol-5-yl)-N-phenyl-5,6,7,8-tetrahydroindolizine-1-carboxamide To a solution of the compound of Step F (550 mg; 0.72 mmol) in methylene chloride (6 mL) there are added, at ambient temperature, triethylamine (300 µL; 1.8 mmol) and mesyl chloride (0.14 mL; 1.8 mmol). After stirring for 20 minutes, the reaction mixture is concentrated to dryness and then diluted with 10 mL of DMSO. 470 mg of NaN$_3$ in powder form (7.2 mmol) are added thereto. The reaction mixture is left for 20 hours at ambient temperature and then for 20 hours at 50° C. It is then poured onto a mixture of dichloromethane and water. The organic phase is washed 3 times with water and then with brine, dried over MgSO$_4$, and then concentrated to dryness to yield the expected product which is used as is in the next Step.

Step H: 7-Amino-N-(4-hydroxyphenyl)-3-(6-{[(3R)-3-methyl-3,4-dihydroisoquinolin-2(1H)-yl]carbonyl}-1,3-benzodioxol-5-yl)-N-phenyl-5, 6,7,8-tetrahydroindolizine-1-carboxamide hydrochloride To a solution of 550 mg of the compound of Step G (0.7 mmol) in ethanol (10 mL) there are added, at ambient temperature, 20 mg of Pd/C 10%. After stirring for 15 hours under 1 bar of hydrogen, the reaction mixture is passed through a Whatman filter and concentrated to dryness. After purification by column chromatography over silica gel (dichloromethane/methanol gradient), the solid is then dissolved in dichloromethane, and 2 mL of 1N HCl in ether are added. The entire batch is stirred for 1 hour and then evaporated to dryness. The hydrochloride thereby obtained is dissolved in a mixture of water/acetonitrile until dissolution is complete and then lyophilised to yield the expected compound in the form of a powder.

Elemental Microanalysis: (%, Theoretical:Measured)
% C=69.17:68.68; % H=5.51:5.09; % N=8.27:8.41; % Cl—=5.24:5.28

EXAMPLE 16

3-(6-{[(3S)-3-(Hydroxymethyl)-3,4-dihydroisoquinolin-2(1H)-yl]-carbonyl}-1,3-benzodioxol-5-yl)-N-(4-hydroxyphenyl)-N-phenyl-5,6,7,8-tetrahydroindolizine-1-carboxamide Step A: Methyl 3-(6-{[(3S)-3-(hydroxymethyl)-3,4-dihydroisoquinolin-2(1H)-yl]-carbonyl}-1,3-benzodioxol-5-yl)-5,6,7,8-tetrahydroindolizine-1-carboxylate The procedure is in accordance with the process in Step A of Example 1 using (3S)-1,2,3,4-tetrahydroisoquinolin-3-ylmethanol.

Step B: Methyl 3-(6-{[(3S)-3-[(prop-2-en-1-yloxy)methyl]-3,4-dihydroisoquinolin-2(1H)-yl]carbonyl}-1,3-benzodioxol-5-yl)-5, 6, 7,8-tetrahydroindolizine-1-carboxylate To a suspension of NaH (703 mg; 17.6 mmol) in THF (20 mL) there is added a solution of 7.8 g of the compound of Step A (16 mmol) dissolved in a mixture of THF (50 mL) and DMF (30 mL). After stirring for 1 hour there is added allyl bromide (1.7 mL; 19 mmol). The reaction mixture is stirred for 48 hours at ambient temperature and is then poured onto a mixture of ethyl acetate and water. The organic phase is washed 3 times with water, and with saturated LiOH solution, dried over MgSO$_4$ and concentrated to dryness. After purification by chromatography over silica gel (dichloromethane/methanol gradient), the expected product is obtained in the form of a solid.

$^1$H NMR: δ: (500 MHz; dmso-d6; 300K): 7.2-6.9 (m, 4H); 7.05 (m, 1H); 6.9 (m, 1H); 6.45-6.1 (m, 1H); 6.15 (m, 2H); 5.9-5.65 (m, 1H); 5.2-5.0 (m, 2H); 5.05-3.8 (m, 1H); 4.85-4.25 (m, 2H); 4.3-3.45 (m, 7H); 3.4-2.4 (m, 6H); 1.95-1.45 (m, 4H)

Step C: N-[4-(Benzyloxy)phenyl]-N-phenyl-3-(6-{[(3S)-3-[(prop-2-n-1-yloxy)methyl]-3,4-dihydroisoquinolin-2(1H)-yl]carbonyl}-1,3-benzodioxol-5-yl)-5, 6, 7,8-tetrahydroindolizine-1-carboxamide The procedure is in accordance with the processes of Steps B and C of Example 1 using 4-(benzyloxy)-N-phenylaniline (cf. Preparation 9").

Step D: 3-(6-{[(3S)-3-(Hydroxymethyl)-3,4-dihydroisoquinolin-2(1H)-yl]carbonyl}-1,3-benzodioxol-5-yl)-N-(4-hydroxyphenyl)-N-phenyl-5,6,7,8-tetrahydroindolizine-1-carboxamide To a suspension of 5.1 g (6.65 mmol) of the compound of Step C in a mixture of dichloromethane (7 mL) and methanol (2 mL) there are added dimethylbarbituric acid (2.1 g; 13.3 mmol) and tetrakis(triphenylphosphine)palladium(0) (300 mg; 0.3 mmol). After stirring for 15 hours at 45° C., the reaction mixture is poured onto a mixture of ethyl acetate and water. The organic phase is washed twice with water, dried over MgSO$_4$, concentrated to dryness and diluted with methanol (5 mL). The batch is then stirred for 24 hours under a hydrogen atmosphere in the presence of Pd/C (100 mg). The reaction mixture is then passed through a Whatman filter, concentrated to dryness, then chromatographed over silica gel (dichloromethane/methanol gradient) and finally lyophilised to yield the expected product in the form of a powder.

Elemental Microanalysis: %, Measured (Theoretical)
% C=72.38 (73); % H=5.22 (5.5); % N=6.59 (6.55)

EXAMPLE 17

N-{3-Fluoro-4-[2-(morpholin-4-yl)ethoxy]phenyl}-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide hydrochloride Elemental Microanalysis: (%, Theoretical:Measured)
% C=67.12:66.79; % H=5.26:4.98; % N=6.96:7.17; % Cl—=4.4:4.77

EXAMPLE 18

3-[6-(3,4-Dihydroisoquinolin-2(1H)-ylcarbonyl)-1,3-benzodioxol-5-yl]-N-{3-fluoro-4-[2-(morpholin-4-yl)ethoxy]phenyl}-N-(4-hydroxyphenyl)indolizine-1-carboxamide hydrochloride Elemental Microanalysis: %, Measured (Theoretical)
% C=66.99 (66.79); % H=4.93 (5.1); % N=7.11 (7.08); % Cl—=4.46 (4.48)

EXAMPLE 19

N-(4-Hydroxyphenyl)-3-(5-methyl-2-{[(3S)-3-[2-(morpholin-4-yl)ethyl]-3,4-dihydroisoquinolin-2(1H)-yl]carbonyl}phenyl)-N-phenyl-5,6,7,8-tetrahydroindolizine-1-carboxamide hydrochloride Elemental Microanalysis: (%, Theoretical:Measured)
% C=72.26:72.51; % H=6.48:6.13; % N=7.66:7.71; % Cl=4.85:4.95; % Cl—=4.85:4.64

EXAMPLE 20

N-(4-Hydroxyphenyl)-3-(2-{[(3S)-3-[2-(morpholin-4-yl)ethyl]-3,4-dihydroisoquinolin-2(1H)-yl]carbonyl}phenyl)-N-phenyl-5,6,7,8-tetrahydroindolizine-1-carboxamide hydrochloride Elemental Microanalysis: (%, Theoretical:Measured)
% C=72:71.11; % H=6.32:5.94; % N=7.81:7.65; % Cl—=4.94:5.08

EXAMPLE 21

N-(4-Hydroxyphenyl)-3-(6-{[(3R)-3-methyl-3,4-dihydroisoquinolin-2(1H)-yl]carbonyl}-1,3-benzodioxol-5-yl)-N-(pyridin-4-yl)indolizine-1-carboxamide hydrochloride Elemental Microanalysis: (%, Theoretical:Measured)
% C=69.24:69.12; % H=4.74:4.23; % N=8.5:8.45; % Cl—=5.38:5.2

EXAMPLE 22

N-(4-Hydroxyphenyl)-6-(6-{[(3S)-3-[2-(morpholin-4-yl)ethyl]-3,4-dihydroisoquinolin-2(1H)-yl]carbonyl}-1,3-benzodioxol-5-yl)-N-phenylpyrrolo[1,2-a]-pyrimidine-8-carboxamide hydrochloride Elemental Microanalysis: (%, Theoretical:Measured)
% C=68.11:66.66; % H=5.32:4.93; % N=9.24:8.84; % Cl—=4.68:5.78
High-Resolution Mass Spectroscopy (ESI+):
Empirical formula: $C_{43}H_{39}N_5O_6$
$[M+H]^+$, calculated: 655.2915
$[M+H]^+$, measured: 655.2915

EXAMPLE 23

N-(3-Cyanophenyl)-N-(4-hydroxyphenyl)-3-(6-{[(3S)-3-[2-(morpholin-4-yl)ethyl]-3,4-dihydroisoquinolin-2(1H)-yl]carbonyl}-1,3-benzodioxol-5-yl)-5,6,78-tetrahydroindolizine-1-carboxamide hydrochloride Elemental Microanalysis: (%, Theoretical:Measured)
% C=68.74:68.59; % H=5.64:5.5; % N=8.91:8.98; % Cl—=4.51:4.48

EXAMPLE 24

N-(3-Fluorophenyl)-N-(4-hydroxyphenyl)-3-(6-{[(3S)-3-[2-(morpholin-4-yl)ethyl]-3,4-dihydroisoquinolin-2(1H)-yl]carbonyl}-1,3-benzodioxol-5-yl)-5,6,7,8-tetrahydroindolizine-1-carboxamide hydrochloride Elemental Microanalysis: (%, Theoretical:Measured)
% C=67.81:67.45; % H=5.69:5.61; % N=7.19:7.42; % Cl—=4.55:4.84

EXAMPLE 25

N-(3,4-Difluorophenyl)-N-(4-hydroxyphenyl)-3-(6-{[(3S)-3-[2-(morpholin-4-yl)ethyl]-3,4-dihydroisoquinolin-2(1H)-yl]carbonyl}-1,3-benzodioxol-5-yl)-5,6,7,8-tetrahydroindolizine-1-carboxamide hydrochloride Elemental Microanalysis: (%, Theoretical:Measured)
% C=66.28:66.56; % H=5.44:5.25; % N=7.03:7.21; % Cl—=4.45:4.32

EXAMPLE 26

N-(3-Fluorophenyl)-3-(6-{[(3S)-3-[2-(morpholin-4-yl)ethyl]-3,4-dihydroisoquinolin-2(1H)-yl]carbonyl}-1,3-benzodioxol-5-yl)-N-phenyl-5,6,7,8-tetrahydroindolizine-1-carboxamide hydrochloride Elemental Microanalysis: (%, Theoretical:Measured)
% C=69.24:70.16; % H=5.81:5.79; % N=7.34:7.47; % Cl—=4.64:4.58

EXAMPLE 27

3-(5-Chloro-2-{[(3S)-3-[2-(morpholin-4-yl)ethyl]-3,4-dihydroisoquinolin-2(1H)-yl]carbonyl}phenyl)-N-(3-fluorophenyl)-N-(4-hydroxyphenyl)-5,6,7,8-tetrahydroindolizine-1-carboxamide hydrochloride Elemental Microanalysis: (%, Theoretical:Measured)
% C=67.1:67.68; % H=5.63:5.4; % N=7.28:7.34; % Cl—=4.61:4.59

EXAMPLE 28

N-(4-Hydroxyphenyl)-3-(5-methoxy-2{[(3S)-3-[2-(morpholin-4-yl)ethyl]-3,4-dihydroisoquinolin-2(1H)-yl]carbonyl}phenyl)-N-phenyl-5,6,7,8-tetrahydroindolizine-1-carboxamide hydrochloride Elemental Microanalysis: (%, Theoretical:Measured)
% C=70.72:70.05; % H=6.34:5.95; % N=7.5:7.33; % Cl—=4.74:4.74

EXAMPLE 29

N-(4-Hydroxyphenyl)-3-(4-methoxy-2-{[(3S)-3-[2-(morpholin-4-yl)ethyl]-3,4-dihydroisoquinolin-2(1H)-yl]carbonyl}phenyl)-N-phenyl-5,6,7,8-tetrahydroindolizine-1-carboxamide hydrochloride Elemental Microanalysis: (%, Theoretical:Measured)
% C=70.72:68.96; % H=6.34:5.78; % N=7.5:7.24; % Cl—=4.74:4.62
High-Resolution Mass Spectroscopy (ESI+):
Empirical formula: $C_{44}H_{46}N_4O_5$
$[M+H]^+$, calculated: 711.3546
$[M+H]^+$, measured: 711.3540

EXAMPLE 30

N-{4-[(3,3-Difluoropiperidin-1-yl)methyl]phenyl}-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide hydrochloride Elemental Microanalysis: (%, Theoretical:Measured)
% C=68.31:69.12; % H=5.22:4.93; % N=7.08:6.96; % Cl—=4.48:4.07

EXAMPLE 31

N-(4-Hydroxyphenyl)-3-(6-{[(3R)-3-methyl-3,4-dihydroisoquinolin-2(1H)-yl]carbonyl}-1,3-benzodioxol-5-yl)-N-(quinolin-6-yl)indolizine-1-carboxamide hydrochloride Elemental Microanalysis: (%, Theoretical:Measured)
% C=71.13:71.29; % H=4.69:4.39; % N=7.9:8.14; % Cl—=5:4.5

EXAMPLE 32

N-(4-Hydroxyphenyl)-3-(6-{[(3R)-3-methyl-3,4-dihydroisoquinolin-2(1H)-yl]carbonyl}-1,3-benzodioxol-5-yl)-N-(2-methylpyridin-4-yl)indolizine-1-carboxamide hydrochloride Elemental Microanalysis: (%, Theoretical:Measured)
% C=69.59:69.81; % H=4.94:4.53; % N=8.32:8.59; % Cl—=5.27:5.01

EXAMPLE 33

N-(4-Hydroxyphenyl)-3-(6-{[(3R)-3-methyl-3,4-dihydroisoquinolin-2(1H)-yl]carbonyl}-1,3-benzodioxol-5-yl)-N-(1-methyl-1H-pyrrolo[2,3-b]pyridin-5-yl)indolizine-1-carboxamide hydrochloride Elemental Microanalysis: (%, Theoretical:Measured)
% C=69.14:70.09; % H=4.81:4.55; % N=9.83:10.09; % Cl—=4.98:3.26

EXAMPLE 34

N-(4-Hydroxyphenyl)-3(6-{[(3R)-3-methyl-3,4-di-hydroisoquinolin-2(1H)-yl]carbonyl}-1,3-benzodi-oxol-5-yl)-N-(pyridin-3-yl)indolizine-1-carboxamide hydrochloride Elemental Microanalysis: (%, Theoretical:Measured)
% C=69.24:70.21; % H=4.74:4.42; % N=8.5:8.51; % Cl—=5.38:3.33

EXAMPLE 35

N-{4-[2-(3,3-Difluoropiperidin-1-yl)ethyl]phenyl}-N-(4-hydroxyphenyl)-3-(6-{[(3R)-3-methyl-3,4-dihydroisoquinolin-2(1H)-yl]carbonyl}-1,3-benzodi-oxol-5-yl)indolizine-1-carboxamide hydrochloride Elemental Microanalysis: (%, Theoretical:Measured)
% C=68.61:67.96; % H=5.38:5.14; % N=6.96:6.76; % Cl—=4.4:4.36

EXAMPLE 36

N-{4-[2-(3,3-Difluoropyrrolidin-1-yl)ethyl]phenyl}-N-(4-hydroxyphenyl)-3-(6-{[(3R)-3-methyl-3,4-dihydroisoquinolin-2(1H)-yl]carbonyl}-1,3-benzodi-oxol-5-yl)indolizine-1-carboxamide hydrochloride Elemental Microanalysis: (%, Theoretical:Measured)
% C=68.31:68.51; % H=5.22:4.85; % N=7.08:6.83; % Cl—=4.48:4.48

EXAMPLE 37

3-(6-{[(3S)-3-(2-Aminoethyl)-3,4-dihydroisoquino-lin-2(1H)-yl]carbonyl}-1,3-benzodioxol-5-yl)-N-(4-hydroxyphenyl)-N-phenyl-5,6,7,8-tetrahydroindoliz-ine-1-carboxamide hydrochloride Step A: Methyl 3-(6-{[(3S)-3-{2-[(tert-butoxycarbo-nyl)amino]ethyl}-3,4-dihydroisoquinolin-2(1H)-yl]carbonyl}-1,3-benzodioxol-5-yl)-5, 6, 7,8-tetrahy-droindolizine-1-carboxylate To a solution of 2 g of the compound of Preparation 1 in 20 mL of dichloromethane there are added, at ambient temperature, 5.5 mL of N,N,N-triethylamine (6.96 mmol), the compound of Preparation 3' (6.96 mmol), and then 0.94 g of hydroxybenzotriazole (HOBT) and 1.34 g of 1-ethyl-3-(3'-dimethylaminopropyl)-carbodiimide (EDC) (6.96 mmol). The reaction mixture is then stirred at ambient temperature overnight, and it is then poured onto ammonium chloride solution and extracted with ethyl acetate. The organic phase is then dried over magnesium sulphate, and then filtered and evaporated to dryness. The crude product thereby obtained is then purified by chromatography over silica gel (heptane/AcOEt gradient) to yield the expected product.

$^1$H NMR: δ (400 MHz; dmso-d6; 300K): 7.2-6.8 (m, 4H, aromatic Hs, H tetrahydroisoquinoline); 7.15-6.90 (m, 4H, aromatic H, tetrahydroisoquinoline); 7.00-6.80 (m, 2H, aromatic H, benzodioxole); 6.68+6.55+6.25 (m, 1H, NH); 6.50-6.05 (m, 1H, aromatic H, tetrahydroindolizine); 6.12 (m, 2H, aliphatic Hs, OCH$_2$O); 4.95+4.20+4.10 (m, 2H, aliphatic H, CH$_2$N tetrahydroisoquinoline); 4.85+4.78+3.80 (m, 1H, aliphatic H, CH tetrahydroisoquinoline); 4.00-3.40 (m, 2H, aliphatic Hs, CH$_2$N tetrahydroindolizine); 3.70-3.50 (m, 3H, COOCH$_3$); 2.95-2.45 (m, 2H, aliphatic Hs, CH$_2$NHBoc); 2.98-2.30 (m, 2H, aliphatic Hs, CH$_2$C tetrahydroindolizine); 3.00+2.60+2.42 (m, 2H, aliphatic Hs, CH$_2$CH tetrahydroindolizine); 1.95-1.40 (m, 4H, aliphatic Hs, CH$_2$CH$_2$ tetrahydroindolizine); 1.35-1.25 (m, 9H, aliphatic Hs, tBu); 1.50-1.15 (m, 2H, aliphatic Hs, CH$_2$CH$_2$NHBoc)

Step B: Lithium 3-(6-{[(3S)-3-{2-[(tert-butoxycar-bonyl)amino]ethyl}-3,4-dihydroisoquinolin-2(1H)-yl]carbonyl}-1,3-benzodioxol-5-yl)-5,6,7,8-tetrahy-droindolizine-1-carboxylate To a solution containing 8.26 mmol of the compound of Step A in 24 mL of dioxane there is added a solution of lithium hydroxide (675 mg, 16.1 mmol). The batch is placed in a microwave oven at 140 W, 100° C. for a period of 2 hours 30 minutes. The reaction mixture is then filtered and evaporated. The solid thereby obtained is dried at 40° C. in an oven in the presence of P$_2$O$_5$.

Step C: tert-Butyl (2-{(3S)-2-[(6-{1-[(4-{[tert-butyl (dimethyl)silyl]oxy}phenyl)-(phenyl)carbamoyl]-5, 6,7,8-tetrahydroindolizin-3-yl}-1,3-benzodioxol-5-yl)carbonyl]-1,2,3,4-tetrahydroisoquinolin-3-yl}ethyl)carbamate To a solution containing 4.73 mmol of the compound of Step B in 47 mL of dichloromethane there are added, dropwise, 1.2 mL of oxalyl chloride at 0° C. The reaction mixture is stirred at ambient temperature for 11 hours and is then co-evaporated several times with dichloromethane. The product thereby obtained is suspended in 37 mL of dichloromethane, and is then added to a solution containing 7.1 mmol of the compound obtained in Preparation 8" in 10 mL of dichloromethane in the presence of 0.6 mL of pyridine (7.1 mmol). The batch is stirred at ambient temperature overnight.

The reaction mixture is concentrated and purified by chromatography over silica gel (dichloromethane/methanol gradient) to yield the expected product.

$^1$H NMR: δ (400 MHz; dmso-d6; 300K): 7.0 (m, 11H, aromatic Hs, Ph+4H, tetrahydroisoquinoline+2H, PhO); 6.80-6.65 (m, 2H, aromatic Hs, PhO); 6.95-6.85 (m, 2H, aromatic H, benzodioxole); 6.70+6.40 (3tl, 1H, NH); 6.10 (m, 2H, aliphatic Hs, OCH$_2$O); 5.25-4.85 (m, 1H, aromatic H, tetrahydroindolizine); 5.00+4.00 (m, 2H, aliphatic H, CH$_2$N tetrahydroisoquinoline); 4.90-3.60 (m, 1H, aliphatic H, CH tetrahydroisoquinoline); 4.10-3.40 (m, 2H, aliphatic Hs, CH$_2$N tetrahydroindolizine); 3.00-2.50 (m, 2H, aliphatic Hs, CH$_2$C tetrahydroindolizine); 3.00+2.40 (m, 2H, aliphatic Hs, CH$_2$CH tetrahydroindolizine); 3.00-2.50 (m, 2H, aliphatic Hs, CH$_2$NHBoc); 1.80-1.50 (m, 4H, aliphatic Hs, CH$_2$CH$_2$ tetrahydroindolizine); 1.50-1.30 (m, 2H, aliphatic Hs, CH$_2$CH$_2$NHBoc); 1.35 (2s, 9H, aliphatic Hs, tBu); 0.90 (s, 9H, aliphatic Hs, tBu-Si); 0.10 (m, 6H, aliphatic Hs, Me-Si)

Step D: 3-(6-{[(3S)-3-(2-Aminoethyl)-3,4-dihy-droisoquinolin-2(1H)-yl]carbonyl}-1,3-benzodioxol-5-yl)-N-(4-hydroxyphenyl)-N-phenyl-5,6,7,8-tetra-hydroindolizine-1-carboxamide hydrochloride To a solution of 800 mg (0.92 mmol) of the compound of Step C in 10 mL of methanol there are added 258 mg (4.60 mmol) of KOH. After stirring for 3 hours at ambient temperature, the reaction mixture is treated with 4M HCl solution in 6 mL of dioxane. After stirring for 2 hours at ambient temperature, the reaction mixture is concentrated and treated with saturated aqueous NaHCO$_3$ solution and extracted with methylene chloride. The organic phase is then dried over magnesium sulphate, and then filtered and evaporated to dryness. The crude product thereby obtained is then purified by chromatography over silica gel (dichloromethane/methanol gradient). The compound is then dissolved in 5 mL of dichloromethane, and 2.5 mL of 1M HCl in ether are added. The compound is filtered off and dried in vacuo. The expected product is obtained in the form of a foam.

Elemental Microanalysis: (%, Theoretical:Measured)

% C=69.51:69.53; % H=5.69:5.27; % N=8.11:8.04; % Cl—=5.13:5.2

High-Resolution Mass Spectroscopy (ESI+):

Empirical formula: C$_{40}$H$_{38}$N$_4$O$_5$

[M+H]$^+$, calculated: 655.2915

[M+H]$^+$, measured: 655.2915

$^1$H NMR: δ (400 MHz; dmso-d6; 300K): 9.55+9.45 (2s, 1H, OH); 7.80+7.75 (2s, 3H, NH$_3^+$); 7.46-6.55 (m, 11H, aromatic Hs, Ph+4H, tetrahydroisoquinoline+2H, PhO); 6.90-6.55 (m, 2H, aromatic Hs, PhO); 7.00-6.70 (several s, 2H, aromatic H, benzodioxole); 5.35-5.00 (several s, 1H, aromatic H, tetrahydroindolizine); 6.10 (several s, 2H, aliphatic Hs, OCH$_2$O); 5.00-3.35 (several m, 4H, aliphatic H, CH$_2$N tetrahydroisoquinoline+CH$_2$N tetrahydroindolizine); 4.85+4.75+3.60 (several m, 1H, aliphatic H, CH tetrahydroisoquinoline); 2.85-2.45 (several m, 2H, aliphatic Hs, CH$_2$NH$_2$); 3.00-2.45 (several m, 2H, aliphatic Hs, CH$_2$C tetrahydroindolizine); 3.05+2.30 (several m, 2H, aliphatic Hs, CH$_2$CH tetrahydroisoquinoline); 1.85-1.40 (several m, 2H, aliphatic Hs, CH$_2$ tetrahydroisoquinoline); 1.95-1.35 (several m, 2H, aliphatic Hs, CH$_2$ tetrahydroisoquinoline); 1.75-1.40 (several m, 2H, aliphatic Hs, CH$_2$CH$_2$NH$_2$)

IR: ν: —OH: 3375 cm$^{-1}$ (phenol); ν: —NH$_3^+$: 3500-2300 cm$^{-1}$ (salt of primary amine); ν: >C=O 1612 cm$^{-1}$+shoulder (amide)

EXAMPLE 38

N-(4-Hydroxyphenyl)-3-(6-{[(3R)-3-[3-(morpholin-4-yl)propyl]-3,4-dihydroisoquinolin-2(1H)-yl]carbonyl}-1,3-benzodioxol-5-yl)-N-phenyl-5,6,7,8-tetrahydroindolizine-1-carboxamide hydrochloride Elemental Microanalysis: (%, Theoretical:Measured)

% C=69.71:69.62; % H=6.11:5.67; % N=7.23:7.12; % Cl—=4.57:4.81

EXAMPLE 39

N-(2,6-Dimethylpyridin-4-yl)-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide hydrochloride Elemental Microanalysis: (%, Theoretical:Measured)

% C=69.91:69.68; % H=5.13:4.78; % N=8.15:8.03; % Cl—=5.16:5.16

EXAMPLE 40

N-(4-Hydroxyphenyl)-3-(6-{[(3R)-3-methyl-3,4-dihydroisoquinolin-2(1H)-yl]carbonyl}-1,3-benzodioxol-5-yl)-N-phenyl-5,6,7,8-tetrahydroindolizine-1-carboxamide Elemental Microanalysis: (%, Theoretical:Measured)

% C=74.86:74.88; % H=5.64:5.31; % N=6.72:6.78

EXAMPLE 41

3-(6-{[(3S)-3-[2-(3,3-Difluoropiperidin-1-yl)ethyl]-3,4-dihydroisoquinolin-2(1H)-yl]carbonyl}-1,3-benzodioxol-5-yl)-N-(4-hydroxyphenyl)-N-phenyl-5,6,7,8-tetrahydroindolizine-1-carboxamide hydrochloride Elemental Microanalysis: (%, Theoretical:Measured)

% C=67.96:68.34; % H=5.7:5.4; % N=7.04:6.97; % Cl—=4.46:4.27

EXAMPLE 42

N-(4-Hydroxyphenyl)-3-(6-{[(3R)-3-methyl-3,4-dihydroisoquinolin-2(1H)-yl]carbonyl}-1,3-benzodioxol-5-yl)-N-(pyridin-4-yl)-5,6,7,8-tetrahydroindolizine-1-carboxamide hydrochloride Elemental Microanalysis: (%, Theoretical:Measured)

% C=68.82:69.46; % H=5.32:4.95; % N=8.45:8.48; % Cl—=5.35:4.6

EXAMPLE 43

3-(6-{[(3S)-3-{2-[(2,2-Difluoroethyl)amino]ethyl}-3,4-dihydroisoquinolin-2(1H)-yl]carbonyl}-1,3-benzodioxol-5-yl)-N-(4-hydroxyphenyl)-N-phenyl-5,6,7,8-tetrahydroindolizine-1-carboxamide Step A: Ethyl 3-(6-{[(3S)-3-{2-[(tert-butoxycarbonyl)amino]ethyl}-3,4-dihydroisoquinolin-2(1H)-yl]carbonyl}-1,3-benzodioxol-5-yl)-5,6,7,8-tetrahydroindolizine-1-carboxylate The process is analogous to that described in Step A of Example 37.

Step B: Ethyl 3-(6-{[(3S)-3-{2-[(tert-butoxycarbonyl)(2,2-difluoroethyl)amino]-ethyl}-3,4-dihydroisoquinolin-2(1H)-yl]carbonyl}-1,3-benzodioxol-5-yl)-5, 6,7,8-tetrahydroindolizine-1-carboxylate To a suspension of 337 mg of NaH (60%) (8.41 mmol) in 13 mL of dimethylformamide there is added, dropwise, a solution of 1.01 g (1.68 mmol) of the compound of Step A in 13 mL of dimethylformamide. The resulting suspension is stirred at ambient temperature for 15 minutes and there are then added 1.08 g (5.04 mmol) of 2,2-difluoroethyl trifluoromethanesulphonate in 13 mL of dimethylformamide. The batch is stirred at ambient temperature for 2 hours. A solution of 20 mL of saturated ammonium chloride is added. The solution is extracted with ethyl acetate. The organic phase is then dried over MgSO$_4$, filtered and concentrated to dryness. After purification by column chromatography over silica gel (cyclohexane/ethyl acetate), the expected product is obtained in the form of an oil.

High-Resolution Mass Spectroscopy (ESI+):
Empirical formula: $C_{37}H_{43}CN_3O_7$
[M+H]$^+$, calculated: 680.3142
[M+H]$^+$, measured: 680.3145
$^1$H NMR: δ (400 MHz; dmso-d6; 300K): 7.25-6.90 (m, 4H, aromatic Hs, tetrahydroisoquinoline); 7.10-6.75 (m, 2H, aromatic H, benzodioxole); 0.40-6.05 (m, 1H, aromatic H, tetrahydroindolizine); 6.10 (m, 2H, aliphatic Hs, OCH$_2$O); 6.25-5.90 (m, 1H, aliphatic Hs, CHF$_2$); 4.95-4.10 (m, 2H, aliphatic H, CH$_2$N tetrahydroisoquinoline); 4.80+3.80 (2m, 1H, aliphatic H, CH tetrahydroisoquinoline); 4.10-4.00 (m, 2H, CH$_2$Et); 4.05-3.40 (m, 2H, aliphatic H, CH$_2$N tetrahydroindolizine); 3.60-2.60 (m, 4H, aliphatic H, CH$_2$CHF$_2$+CH$_2$NBoc); 3.00-2.35 (m, 2H, aliphatic Hs, CH$_2$C tetrahydroindolizine); 3.00+2.45 (m, 2H, aliphatic Hs, CH$_2$CH tetrahydroisoquinoline); 1.95+1.40 (m, 4H, aliphatic Hs, CH$_2$CH$_2$ tetrahydroindolizine); 1.40 (m, 9H, aliphatic Hs, $^t$Bu); 1.65-1.20 (m, 2H, aliphatic Hs, CH$_2$CH$_2$NBoc); 1.18+1.10 (2t, 3H, aliphatic Hs CH$_3$Et)

Step C: tert-Butyl (2-{(3S)-2-[(6-{1-[(4-{[tert-butyl(dimethyl)silyl]oxy}phenyl)(phenyl)-carbamoyl]-5,6,7,8-tetrahydroindolizin-3-yl}-1,3-benzodioxol-5-yl)carbonyl]-1,2,3,4-tetrahydroisoquinolin-3-yl}ethyl)(2,2-difluoroethyl)carbamate The process is analogous to that described in Steps B and C of Example 37.
$^1$H NMR: δ (400 MHz; dmso-d6; 300K): 7.30-6.60 (m, 9H, aromatic Hs, 4H tetrahydroisoquinoline+Ph); 6.90-6.70 (m, 2H, aromatic H, benzodioxole); 6.80-6.60 (m, 4H, PhO); 6.10 (m, 2H, aliphatic Hs, OCH$_2$O); 6.20-5.90 (m, 1H, aliphatic Hs, CHF$_2$); 5.50-4.80 (4s, 1H, aromatic H, tetrahydroindolizine); 5.20-4.00 (m, 2H, aliphatic H, CH$_2$N tetrahydroisoquinoline); 4.80+4.70+3.50 (3m, 1H, aliphatic H, CH tetrahydroisoquinoline); 4.20-3.40 (m, 2H, aliphatic H, CH$_2$N tetrahydroindolizine); 3.60-3.10 (m, 4H, aliphatic H, CH$_2$CHF$_2$+CH$_2$NBoc); 3.00+2.60 (m, 2H, aliphatic Hs, CH$_2$CH tetrahydroisoquinoline); 3.00-2.50 (m, 2H, aliphatic Hs, CH$_2$C tetrahydroindolizine); 1.80+1.50 (m, 4H, aliphatic Hs, CH$_2$CH$_2$ tetrahydroindolizine); 1.60-1.30 (m, 2H, aliphatic Hs, CH$_2$CH$_2$NBoc); 1.40-1.30 (m, 9H, aliphatic Hs, tBu); 0.90 (4s, 9H, aliphatic Hs, tBu-Si); 0.10 (4s, 6H, aliphatic Hs, Me-Si)

Step D: 3-(6-{[(3S)-3-{2-[(2,2-Difluoroethyl)amino]ethyl}-3,4-dihydroisoquinolin-2(1H)-yl]carbonyl}-1,3-benzodioxol-5-yl)-N-(4-hydroxyphenyl)-N-phenyl-5, 6, 7,8-tetrahydroindolizine-1-carboxamide To a solution of 933 mg (1.00 mmol) of the compound of Step C in 10 mL of methanol there are added 280 mg (5.00 mmol) of KOH. After stirring for 3 hours at ambient temperature, the reaction mixture is treated with 4M HCl solution in 6 mL of dioxane. After stirring for 2 hours at ambient temperature, the reaction mixture is concentrated and treated with aqueous saturated NaHCO$_3$ solution and then extracted with methylene chloride. The organic phase is then dried over magnesium sulphate, and then filtered and evaporated to dryness. The crude product thereby obtained is then purified by chromatography over silica gel (dichloromethane/methanol gradient) to yield the expected product in the form of a foam.
Elemental Microanalysis: (%, Theoretical:Measured)
% C=70.18:69.79; % H=5.61:5.67; % N=7.79:7.7
High-Resolution Mass Spectroscopy (ESI+):
Empirical formula: $C_{42}H_{40}F_2N_4O_5$
[M+H]$^+$, calculated: 655.2915
[M+H]$^+$, measured: 655.2915

EXAMPLE 44

N-(4-Hydroxyphenyl)-3-(6-{[(3S)-3-[2-(3-methoxyazetidin-1-yl)ethyl]-3,4-dihydroisoquinolin-2(1H)-yl]carbonyl}-1,3-benzodioxol-5-yl)-N-phenyl-5,6,7,8-tetrahydroindolizine-1-carboxamide Elemental Microanalysis: (%, Theoretical:Measured)
% C=72.91:72.73; % H=6.12:5.67; % N=7.73:7.74

EXAMPLE 45

N-(4-Hydroxyphenyl)-3-(6-{[(3R)-3-methyl-3,4-dihydroisoquinolin-2(1H)-yl]carbonyl}-1,3-benzodioxol-5-yl)-N-{t-[2-(morpholin-4-yl)ethyl]-1H-pyrazol-4-yl}indolizine-1-carboxamide hydrochloride Elemental Microanalysis: (%, Theoretical:Measured)
% C=66.27:66.05; % H=5.43:5.27; % N=11.04:11.07; % Cl—=4.66:4.61

EXAMPLE 46

N-(3-Fluoropyridin-4-yl)-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide hydrochloride High-resolution mass spectroscopy (ESI+):
Empirical formula: $C_{38}H_{29}FN_4O_5$
[M+H]$^+$, calculated: 641.2195
[M+H]$^+$, measured: 641.2195

EXAMPLE 47

3-(5-Chloro-2-{[(3R)-3-methyl-3,4-dihydroisoquinolin-2(1H)-yl]-carbonyl}phenyl)-N-(4-hydroxyphenyl)-N-(1-methyl-1H-pyrazol-4-yl)-5,6,7,8-tetrahydroindolizine-1-carboxamide Elemental Microanalysis: (%, Theoretical:Measured)
% C=69.72:69.53; % H=5.53:5.6; % N=11.29:10.85

EXAMPLE 48

N-(4-Hydroxyphenyl)-3-(7-{[(3R)-3-methyl-3,4-dihydroisoquinolin-2(1H)-yl]carbonyl}-2,3-dihydro-1,4-benzodioxin-6-yl)-N-(1-methyl-1H-pyrazol-4-yl)-5,6,7,8-tetrahydroindolizine-1-carboxamide Elemental Microanalysis: (%, Theoretical:Measured)
% C=70.9:70.89; % H=5.79:5.56; % N=10.88:10.8

EXAMPLE 49

3-(5-Chloro-2-{[(3R)-3-methyl-3,4-dihydroisoquinolin-2(1H)-yl]-carbonyl}phenyl)-N-(4-hydroxyphenyl)-N-(pyridin-4-yl)indolizine-1-carboxamide hydrochloride Elemental Microanalysis: (%, Theoretical:Measured)
% C=68.42:68.17; % H=4.65:4.48; % N=8.63:8.48; % Cl—=5.46:5.13

EXAMPLE 50

3-(5-Chloro-2-{[(3R)-3-methyl-3,4-dihydroisoquinolin-2(1H)-yl]-carbonyl}phenyl)-N-(4-hydroxyphenyl)-N-(1-methyl-1H-pyrrolo[2,3-b]pyridin-5-yl)indolizine-1-carboxamide Elemental Microanalysis: (%, Theoretical:Measured)
% C=72.12:71.58; % H=4.84:4.84; % N=10.51:10.48

EXAMPLE 51

N-(4-Hydroxyphenyl)-N-(imidazo[1,2-a]pyridin-7-yl)-3-(6-{[(3R)-3-methyl-3,4-dihydroisoquinolin-2(1H)-yl]carbonyl}-1,3-benzodioxol-5-yl)indolizine-1-carboxamide hydrochloride Elemental Microanalysis: (%, Theoretical:Measured)
% C=68.81:68.28; % H=4.62:4.59; % N=10.03:9.66; % Cl—=5.08:4.81

EXAMPLE 52

N-(4-Hydroxyphenyl)-3-(2-{[(3R)-3-methyl-3,4-dihydroisoquinolin-2(1H)-yl]carbonyl}phenyl)-N-(1-methyl-1H-pyrrolo[2,3-b]pyridin-5-yl)indolizine-1-carboxamide Elemental Microanalysis: (%, Theoretical:Measured)
% C=76.05:75.88; % H=5.26:5.24; % N=11.09:11.09

EXAMPLE 53

N-(4-Hydroxyphenyl)-3-(6-{[(3R)-3-methyl-3,4-dihydroisoquinolin-2(1H)-yl]carbonyl}-1,3-benzodioxol-5-yl)-N-(2-methylimidazo[1,2-a]pyridin-7-yl)indolizine-1-carboxamide hydrochloride Elemental Microanalysis: (%, Theoretical:Measured)
% C=69.14:69.65; % H=4.81:4.75; % N=9.83:9.79; % Cl—=4.98:4.7

EXAMPLE 54

N-(4-Hydroxyphenyl)-3-(6-{[(3R)-3-methyl-3,4-dihydroisoquinolin-2(1H)-yl]carbonyl}-1,3-benzodioxol-5-yl)-N-(6-methylpyridin-3-yl)indolizine-1-carboxamide hydrochloride Elemental Microanalysis: (%, Theoretical:Measured)
% C=69.59:68.78; % H=4.94:5; % N=8.32:8.33; % Cl—=5.27:5.18

EXAMPLE 55

N-(5-Fluoropyridin-3-yl)-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide Elemental Microanalysis: (%, Theoretical:Measured)
% C=71.24:70.77; % H=4.56:4.36; % N=8.75:8.82

EXAMPLE 56

N-(4-Hydroxyphenyl)-N-(2-methoxypyridin-4-yl)-3-(6-{[(3R)-3-methyl-3,4-dihydroisoquinolin-2(1H)-yl]carbonyl}-1,3-benzodioxol-5-yl)indolizine-1-carboxamide High-resolution mass spectroscopy (ESI+):
Empirical formula: $C_{39}H_{32}N_4O_6$
$[M+H]^+$, calculated: 653.2395
$[M+H]^+$, measured: 653.2385

EXAMPLE 57

3-[6-(3,4-Dihydroisoquinolin-2(1H)-ylcarbonyl)-1,3-benzodioxol-5-yl]-N-(4-hydroxyphenyl)-N-phenyl-5,6,7,8-tetrahydroindolizine-1-carboxamide Elemental Microanalysis: %, Measured (Theoretical)
% C=74.17 (74.62); % H=5.43 (5.44); % N=6.87 (6.87)

EXAMPLE 58

N-(4-Hydroxyphenyl)-3-(6-{[(3R)-3-methyl-3,4-dihydroisoquinolin-2(1H)-yl]carbonyl}-1,3-benzodioxol-5-yl)-N-[2-(propan-2-yl)pyridin-4-yl]indolizine-1-carboxamide hydrochloride Elemental Microanalysis: (%, Theoretical:Measured)
% C=70.23:69.95; % H=5.32:5.4; % N=7.99:7.99; % Cl—=5.06:4.92

EXAMPLE 59

N-(4-Hydroxyphenyl)-3-(6-{[(3R)-3-methyl-3,4-dihydroisoquinolin-2(1H)-yl]carbonyl}-1,3-benzodioxol-5-yl)-N-(pyrazolo[1,5-a]pyrimidin-6-yl)indolizine-1-carboxamide Elemental Microanalysis: (%, Theoretical:Measured)
% C=70.68:70.47; % H=4.56:4.61; % N=12.68:12.45

EXAMPLE 60

3-(5-Fluoro-2-{[(3R)-3-methyl-3,4-dihydroisoquinolin-2(1H)-yl]-carbonyl}phenyl)-N-(4-hydroxyphenyl)-N-(1-methyl-1H-pyrazol-4-yl)indolizine-1-carboxamide Elemental Microanalysis: %, Measured (Theoretical)
% C=71.85 (72.11); % H=4.78 (5.04); % N=10.79 (11.68)

EXAMPLE 61

3-(5-Fluoro-2-{[(3R)-3-methyl-3,4-dihydroisoquinolin-2(1H)-yl]-carbonyl}phenyl)-N-(4-hydroxyphenyl)-N-(1-methyl-1H-pyrazol-4-yl)-5,6,7,8-tetrahydroindolizine-1-carboxamide Elemental Microanalysis: %, Measured (Theoretical)
% C=72.31 (71.62); % H=5.6 (5.68); % N=10.94 (11.6)

EXAMPLE 62

3-(5-Fluoro-2-{[(3R)-3-methyl-3,4-dihydroisoquinolin-2(1H)-yl]-carbonyl}phenyl)-N-(4-hydroxyphenyl)-N-(pyridin-4-yl)indolizine-1-carboxamide Elemental Microanalysis: %, Measured (Theoretical)
% C=74.08 (74.48); % H=4.82 (4.9); % N=8.59 (9.39)

EXAMPLE 63

3-(5-Fluoro-2-{[(3R)-3-methyl-3,4-dihydroisoquinolin-2(1H)-yl]-carbonyl}phenyl)-N-(4-hydroxyphenyl)-N-(1-methyl-1H-pyrrolo[2,3-b]pyridin-5-yl)indolizine-1-carboxamide Elemental Microanalysis: %, Measured (Theoretical)
% C=73.14 (73.95); % H=4.83 (4.96); % N=10.29 (10.78)

EXAMPLE 64

3-(5-Fluoro-2-{[(3R)-3-r ethyl-3,4-dihydroisoquinolin-2(1H)-yl]-carbonyl}phenyl)-N-(4-hydroxyphenyl)-N-(pyridin-4-yl)-5,6,7,8-tetrahydroindolizine-1-carboxamide Elemental Microanalysis: %, Measured (Theoretical)
% C=74.61 (73.98); % H=5.26 (5.54); % N=8.94 (9.33)

EXAMPLE 65

3-(5-Fluoro-2-{[(3R)-3-methyl-3,4-dihydroisoquinolin-2(1H)-yl]-carbonyl}phenyl)-N-(4-hydroxyphenyl)-N-(1-methyl-1H-pyrrolo[2,3-b]pyridin-5-yl)-5,6,7,8-tetrahydroindolizine-1-carboxamide Elemental Microanalysis: %, Measured (Theoretical)
% C=73.59 (73.49); % H=5.22 (5.55); % N=9.93 (10.71)

EXAMPLE 66

N-(4-Hydroxyphenyl)-3-(6-{[(3R)-3-methyl-3,4-dihydroisoquinolin-2(1H)-yl]carbonyl}-1,3-benzodioxol-5-yl)-N-([1,2,4]triazolo[1,5-a]pyrimidin-6-yl)-indolizine-1-carboxamide Elemental Microanalysis: %, Measured (Theoretical)
% C=68.57 (68.77); % H=3.92 (4.4); % N=14.21 (14.77)
High-resolution mass spectroscopy (ESI+):
Empirical formula: $C_{38}H_{29}N_7O_5$
[M+H]$^+$, calculated: 664.2303
[M+H]$^+$, measured: 664.2310

EXAMPLE 67

N-(4-Hydroxyphenyl)-3-(6-{[(3R)-3-methyl-3,4-dihydroisoquinolin-2(1H)-yl]carbonyl}-1,3-benzodioxol-5-yl)-N-(1-oxidopyridin-4-yl)indolizine-1-carboxamide Elemental Microanalysis: %, Measured (Theoretical)
% C=69.7 (71.46); %% H=4.43 (4.73); % N=8.54 (8.77)
High-Resolution Mass Spectroscopy (ESI+):
Empirical formula: $C_{38}H_{30}N_4O_6$
[M+H]$^+$, calculated: 639.2238
[M+H]$^+$, measured: 639.2234

EXAMPLE 68

N-(4-Hydroxyphenyl)-3-(2-{[(3R)-3-methyl-3,4-dihydroisoquinolin-2(1H)-yl]carbonyl}phenyl)-N-(pyridin-4-yl)indolizine-1-carboxamide hydrochloride Elemental Microanalysis: %, Measured (Theoretical)
% C=71.97 (72.25); % H=5.21 (5.08); % N=8.99 (9.11); % Cl—=5.32 (5.76)
High-Resolution Mass Spectroscopy (ESI+):
Empirical formula: $C_{37}H_{30}N_4O_3$
[M+H]$^+$, calculated: 579.2391
[M+H]$^+$, measured: 579.2403

EXAMPLE 69

N-(4-Hydroxyphenyl)-N-(1-methyl-1H-pyrrolo[2,3-b]pyridin-5-yl)-3-(6-{[(3R)-3-[3-(morpholin-4-yl)propyl]-3,4-dihydroisoquinolin-2(1H)-yl]carbonyl}-1,3-benzodioxol-5-yl)-5,6,7,8-tetrahydroindolizine-1-carboxamide hydrochloride Elemental Microanalysis: %, Measured (Theoretical)
% C=67.63 (68.06); % H=5.27 (5.95); % N=10.08 (10.13); % Cl—=4.53 (4.27)
High-Resolution Mass Spectroscopy (ESI+):
Empirical formula: $C_{47}H_{48}N_6O_6$
[M+H]$^+$, calculated: 793.3708
[M+H]$^+$, measured: 793.3704

EXAMPLE 70

N-(4-Hydroxyphenyl)-3-(6-{[(3R)-3-methyl-3,4-dihydroisoquinolin-2(1H)-yl]carbonyl}-1,3-benzodioxol-5-yl)-N-(1-methyl-1H-pyrazolo[3,4-b]pyridin-5-yl)indolizine-1-carboxamide Step A: N-[4-[tert-Butyl(dimethyl)silyl]oxyphenyl]-3-[6-[(3R)-3-methyl-3,4-dihydro-1H-isoquinoline-2-carbonyl]-1, 3-benzodioxol-5-yl]-N-(1-methyl-1H-pyrazolo[3,4-b]pyridin-5-yl)indolizine-1-carboxamide The title product is obtained in accordance with the process of Step A of Example 86, replacing the compound of Preparation 36" with that of Preparation 35".
LCMS: [M+H]$^+$=791.4 vs. 791.3 calculated Step B: N-(4-Hydroxyphenyl)-3-(6-{[(3R)-3-methyl-3,4-dihydroisoquinolin-2(1H)-yl]-carbonyl}-1,3-benzodioxol-5-yl)-N-(1-methyl-1H-pyrazolo[3,4-b]pyridin-5-yl)indolizine-1-carboxamide The procedure is in accordance with a protocol analogous to that described in Step D of Example 1. The product thereby obtained is subjected to a step of conversion into a salt in the presence of HCl in ether.
IR (ATR) cm$^{-1}$: 2500 to 3000 ν —OH, 1614 ν>C=O amides, 1236 ν>C—O—C<, 740 γ >CH—Ar
Elemental Microanalysis: %, Measured (Theoretical)
% C=71.07 (70.99); % H=4.45 (4.77); % N=12.37 (12.42)
High-Resolution Mass Spectroscopy (ESI+):
Empirical formula: $C_{40}H_{32}N_6O_5$
[M+H]$^+$, calculated: 677.2507
[M+H]$^+$, measured: 677.2510

EXAMPLE 71

4-[(4-Hydroxyphenyl){[3-(6-{[(3R)-3-methyl-3,4-dihydroisoquinolin-2(1H)-yl]carbonyl}-1,3-benzodioxol-5-yl)indolizin-1-yl]carbonyl}amino]-1-methyl-pyridinium chloride

Step A: 4-[(4-Hydroxyphenyl){[3-(6-{[(3R)-3-methyl-3,4-dihydroisoquinolin-2(1H)-yl]-carbonyl}-1,3-benzodioxol-5-yl)indolizin-1-yl]carbonyl}amino]-1-methyl pyridinium iodide The compound of Example 21 (311 mg, 0.5 mmol) is dissolved in dichloromethane and washed with saturated aqueous sodium hydrogen carbonate solution. After drying the organic phase over magnesium sulphate and evaporating to dryness, the residue is dissolved in ethanol (30 mL). Methyl iodide (45 μL, 0.7 mmol) is then added and the reaction mixture is heated to 40° C. The solution thereby obtained is evaporated to dryness. The crude reaction product is purified over a silica gel column using dichloromethane and methanol as solvents. The compound is obtained in the form of a white powder which is used directly in the next Step.

$^1$H NMR (500 MHz, dmso-d6) δ ppm: 9.95 (bs, 1H), 8.6-8.45 (m, 2H), 8.35-8.05 (several m, 1H), 8.3-8 (several m, 1H), 7.45-6.7 (several m, 8H), 7.4-6.9 (several m, 4H), 6.45-6.3 (several s, 1H), 6.45-6.3 (m, 2H), 6.15 (s, 2H), 5.05-3.55 (several d, 2H), 4.75/3.8 (m+m, 1H), 4.15 (2*s, 3H), 2.95-2.1 (several m, 2H), 1-0.15 (several m, 3H)

Step B: 4-[(4-Hydroxyphenyl){[3-(6-{[(3R)-3-methyl-3,4-dihydroisoquinolin-2(1H)-yl]-carbonyl}-1,3-benzodioxol-5-yl)indolizin-1-yl]carbonyl}amino]-1-methyl pyridinium chloride The compound of the preceding Step (320 mg, 0.42 mmol) is dissolved in methanol (20 mL), and then silver carbonate (173 mg, 0.628 mmol) is added, in portions, over 10 minutes. The resulting suspension is stirred for 1 hour at ambient temperature; the precipitate is filtered off and washed with methanol. The filtrate is concentrated to dryness, and then treated with 50 mL of 2N hydrochloric acid solution, heated at 60° C. for 30 minutes and then evaporated to dryness. The final product is obtained after purification over a silica C18 column using a 0.1% hydrochloric acid solution and acetonitrile as solvents. The title compound is obtained in the form of a white powder which is lyophilised in a mixture of water/acetonitrile.

IR (ATR) cm$^{-1}$: 3388 ν —OH phenol, 1650+1627 ν>C═O amides

High-Resolution Mass Spectroscopy (ESI+):

Empirical formula: $C_{39}H_{33}N_4O_5$

[M]$^+$, calculated=637.2445.

[M]$^+$, measured=637.2431

The compounds of Examples 72, 73, 77, 78-80, 84 and 85 are synthesised in accordance with the process of Example 3 using the acid of Preparation 7, the appropriate 1,2,3,4-tetrahydroisoquinoline or the appropriate compound obtained in accordance with one of Preparations 1' to 7', and the suitable NHR$_3$R$_4$ amine.

EXAMPLE 72

N-(4-Hydroxyphenyl)-N-methyl-6-(6-{[(3R)-3-methyl-3,4-dihydroisoquinolin-2(1H)-yl]carbonyl}-1,3-benzodioxol-5-yl)-1,2,3,4-tetrahydropyrrolo[1,2-a]-pyrazine-8-carboxamide LC/MS ($C_{33}H_{32}N_4O_5$) 565 [M+H]$^+$; RT 1.47 (Method B), it being understood that RT denotes retention time

EXAMPLE 73

N-Ethyl-N-(4-hydroxyphenyl)-6-(6-{[(3R)-3-methyl-3,4-dihydroisoquinolin-2(1H)-yl]carbonyl}-1,3-benzodioxol-5-yl)-1,2,3,4-tetrahydropyrrolo[1,2-a]-pyrazine-8-carboxamide LC/MS ($C_{34}H_{34}N_4O_5$) 579 [M+H]$^+$; RT 1.55 (Method B)

EXAMPLE 74

3-[6-(3,4-Dihydroisoquinolin-2(1H)-ylcarbonyl)-1,3-benzodioxol-5-yl]-N-(4-hydroxyphenyl)-N-methyl-5,6,7,8-tetrahydroindolizine-1-carboxamide LC/MS ($C_{33}H_{31}N_3O_5$) 550 [M+H]$^+$; RT 1.24 (Method B)

EXAMPLE 75

3-[6-(3,4-Dihydroisoquinolin-2(1H)-ylcarbonyl)-1,3-benzodioxol-5-yl]-N-ethyl-N-(4-hydroxyphenyl)-5,6,7,8-tetrahydroindolizine-1-carboxamide LC/MS ($C_{34}H_{33}N_3O_5$) 564 [M+H]$^+$; RT 1.30 (Method B)

EXAMPLE 76

N-Butyl-3-[6-(3,4-dihydroisoquinolin-2(1H)-ylcarbonyl)-1,3-benzodioxol-5-yl]-N-(4-hydroxyphenyl)-5,6,7,8-tetrahydroindolizine-1-carboxamide LC/MS ($C_{36}H_{37}N_3O_5$) 592 [M+H]$^+$; RT 1.39 (Method B)

EXAMPLE 77

N-Ethyl-N-(4-hydroxyphenyl)-6-(6-{[(3S)-3-methyl-3,4-dihydroisoquinolin-2(1H)-yl]carbonyl}-1,3-benzodioxol-5-yl)-1,2,3,4-tetrahydropyrrolo[1,2-a]-pyrazine-8-carboxamide LC/MS ($C_{34}H_{34}N_4O_5$) 579 [M+H]$^+$; RT 1.50 (Method B)

EXAMPLE 78

N,N-Dibutyl-6-(6-{[(3R)-3-methyl-3,4-dihydroisoquinolin-2(1H)-yl]-carbonyl}-1,3-benzodioxol-5-yl)-1,2,3,4-tetrahydropyrrolo[1,2-a]pyrazine-8-carboxamide LC/MS ($C_{34}H_{42}N_4O_4$) 571 [M+H]$^+$; RT 1.79 (Method B)

EXAMPLE 79

N-Butyl-N-(4-hydroxyphenyl)-6-(6-{[(3R)-3-methyl-3,4-dihydroisoquinolin-2(1H)-yl]carbonyl}-1,3-benzodioxol-5-yl)-1,2,3,4-tetrahydropyrrolo[1,2-a]-pyrazine-8-carboxamide LC/MS ($C_{36}H_{38}N_4O_5$) 607 [M+H]$^+$; RT 1.65 (Method B)

EXAMPLE 80

N-(4-Hydroxyphenyl)-6-(6-{[(3R)-3-methyl-3,4-dihydroisoquinolin-2(1H)-yl]carbonyl}-1,3-benzodioxol-5-yl)-N-(propan-2-yl)-1,2,3,4-tetrahydropyrrolo[1,2-a]pyrazine-8-carboxamide LC/MS ($C_{35}H_{36}N_4O_5$) 593 [M+H]$^+$; RT 1.58 (Method B)

EXAMPLE 81

N-(4-Hydroxyphenyl)-N-methyl-3-(6-{[(3R)-3-methyl-3,4-dihydroisoquinolin-2(1H)-yl]carbonyl}-1,3-benzodioxol-5-yl)-5,6,7,-tetrahydroindolizine-1-carboxamide LC/MS ($C_{34}H_{33}N_3O_5$) 564 [M+H]$^+$; RT 2.48 (Method A)

EXAMPLE 82

N-(4-Hydroxyphenyl)-N-methyl-3-(6-{[(3S)-3-methyl-3,4-dihydroisoquinolin-2(1H)-yl]carbonyl}-1,3-benzodioxol-5-yl)-5,6,7,8-tetrahydroindolizine-1-carboxamide LC/MS ($C_{34}H_{33}N_3O_5$) 564 [M+H]$^+$; RT 2.55 (Method A)

EXAMPLE 83

3-[6-(3,4-Dihydroisoquinolin-2(1H)-ylcarbonyl)-1,3-benzodioxol-5-yl]-N-(4-hydroxyphenyl)-N-methyl-indolizine-1-carboxamide LC/MS ($C_{33}H_{27}N_3O_5$) 546 [M+H]$^+$; RT 2.40 (Method A)

EXAMPLE 84

6-[6-(3,4-Dihydroisoquinolin-2(1H)-ylcarbonyl)-1,3-benzodioxol-5-yl]-N-(4-hydroxyphenyl)-N-methyl-1,2,3,4-tetrahydropyrrolo[1,2-a]pyrazine-8-carboxamide LC/MS ($C_{32}H_{30}N_4O_5$) 551 [M+H]$^+$; RT 1.45 (Method B)

EXAMPLE 85

6-[6-(3,4-Dihydroisoquinolin-2(1H)-ylcarbonyl)-1,3-benzodioxol-5-yl]-N-ethyl-N-(4-hydroxyphenyl)-1,2,3,4-tetrahydropyrrolo[1,2-a]pyrazine-8-carboxamide LC/MS ($C_{33}H_{32}N_4O_5$) 565 [M+H]$^+$; RT 1.49 (Method B)

EXAMPLE 86

N-(4-Hydroxyphenyl)-3-[6-[(3R)-3-methyl-3,4-dihydro-1H-isoquinoline-2-carbonyl]-1,3-benzodioxol-5-yl]-N-(3-methylpyrazolo[1,5-a]pyrimidin-6-yl)-indolizine-1-carboxamide hydrochloride Step A: N-[4-[tert-Butyl(dimethyl)silyl]oxyphenyl]-3-[6-[(3R)-3-methyl-3,4-dihydro-1H-isoquinoline-2-carbonyl]-1, 3-benzodioxol-5-yl]-N-(3-methylpyrazolo[1,5-a]pyrimidin-6-yl)indolizine-1-carboxamide To a solution of 0.6 g of 3-(6-{[(3R)-3-methyl-3,4-dihydroisoquinolin-2(1H)-yl]carbonyl}-1,3-benzodioxol-5-yl) indolizine-1-carboxylic acid (1.3 mmol) in 6 mL of dichloroethane there is added 0.18 mL of 1-chloro-N,N,2-trimethyl-prop-1-en-1-amine (2 mmol). The reaction mixture is stirred at ambient temperature for 2 hours and there is then added 0.8 g of the compound of Preparation 36" (2.2 mmol). The batch is refluxed for 20 hours and is then cooled and diluted with a mixture of dichloromethane and saturated NaHCO$_3$ solution. After separation of the phases, the organic phase is dried over MgSO$_4$ and concentrated to dryness The crude product thereby obtained is purified by chromatography over silica gel (dichloromethane/methanol gradient).

LC/MS: [M+H]$^+$=791.4 vs. 791.3 calculated

Step B: N-(4-Hydroxyphenyl)-3-[6-[(3R)-3-methyl-3,4-dihydro-1H-isoquinoline-2-carbonyl]-1, 3-benzodioxol-5-yl]-N-(3-methylpyrazolo[1,5-a]pyrimidin-6-yl)indolizine-1-carboxamide hydrochloride The procedure is in accordance with a protocol analogous to that described in Step D of Example 1. The product thereby obtained is subjected to a step of conversion into a salt in the presence of HCl in ether.

IR (ATR) cm$^{-1}$: 2500 to 3000 ν —OH, 1614 ν>C═O amides, 1236 ν>C—O—C<, 740 γ >CH—Ar High-Resolution Mass Spectroscopy (ESI+):
Empirical formula: $C_{40}H_{32}N_6O_5$
[M+H]$^+$, calculated: 677.2507
[M+H]$^+$, measured: 677.2506

Pharmacological Study

EXAMPLE A

Inhibition of Bcl-2 by the Fluorescence Polarisation Technique

The fluorescence polarisation tests were carried out on microplates (384 wells). The Bcl-2 protein, labelled (histag-Bcl-2 such that Bcl-2 corresponds to the UniProtKB® primary accession number: P10415), at a final concentration of 2.50×10$^{-8}$ M, is mixed with a fluorescent peptide (Fluorescein-REIGAQLRRMADDLNAQY), at a final concentration of 1.00×10$^{-8}$ M in a buffer solution (Hepes 10 mM, NaCl 150 mM, Tween20.05%, pH 7.4), in the presence or absence of increasing concentrations of test compounds. After incubation for 2 hours, the fluorescence polarisation is measured.

The results are expressed in IC$_{50}$ (the concentration of compound that inhibits fluorescence polarisation by 50%) and are presented in Table 1 below.

The results show that the compounds of the invention inhibit interaction between the Bcl-2 protein and the fluorescent peptide described hereinbefore.

EXAMPLE B

In Vitro Cytotoxicity

The cytotoxicity studies were carried out on the RS4; 11 leukaemia tumour line.

The cells are distributed onto microplates and exposed to the test compounds for 48 hours.

The cell viability is then quantified by a colorimetric assay, the Microculture Tetrazolium Assay (Cancer Res., 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

$IC_{50}$ of Bcl-2 inhibition (fluorescence polarisation test) and of cytotoxicity for RS4;11 cells

| | $IC_{50}$ (nM) Bcl-2 FP | $IC_{50}$ (nM) MTT RS4;11 |
|---|---|---|
| Example 1 | 17.9 | 11.3 |
| Example 2 | 17.0 | 36 |
| Example 3 | 33.6 | 66.5 |
| Example 4 | 56.4 | 251 |
| Example 5 | 55.9 | 416 |
| Example 6 | 60.3 | 161 |
| Example 7 | 46.4 | 108 |
| Example 8 | 24.5 | 20.5 |
| Example 9 | 40.6 | 780 |
| Example 10 | 24.7 | 439 |
| Example 11 | 10.9 | 83.7 |
| Example 12 | 10.4 | 116 |
| Example 13 | 5.8 | 33.65 |
| Example 14 | 3.7 | 7.6 |
| Example 15 | 5.7 | 166 |
| Example 16 | 7.5 | 252 |
| Example 17 | 3.4 | 11.8 |
| Example 18 | 7.5 | 47.7 |
| Example 19 | 8.0 | 235 |
| Example 20 | 11.1 | 205 |
| Example 21 | 4.6 | 25.3 |
| Example 22 | 12.9 | 263 |
| Example 23 | 3.8 | 9.99 |
| Example 24 | 6.2 | 28.4 |
| Example 25 | 7.9 | 30 |
| Example 26 | 16.6 | 300 |
| Example 27 | 7.7 | 44.1 |
| Example 28 | 8.8 | 112 |
| Example 29 | 19.0 | 163 |
| Example 30 | 10.4 | 52.3 |
| Example 31 | 5.4 | 13.7 |
| Example 32 | 5.0 | 32.7 |
| Example 33 | 4.6 | 6.33 |
| Example 34 | 5.6 | 27.3 |
| Example 35 | 15.1 | 62.2 |
| Example 36 | 12.6 | 49.7 |
| Example 37 | 2.9 | 24.7 |
| Example 38 | 4.6 | 9.52 |
| Example 39 | 4.6 | 26.3 |
| Example 40 | 6.0 | 49 |
| Example 41 | 41.5 | 294 |
| Example 42 | 5.1 | 57.6 |
| Example 43 | 4.8 | 26 |
| Example 44 | 2.9 | 8.56 |
| Example 45 | 3.8 | 63.8 |
| Example 46 | 4.1 | 27.9 |
| Example 47 | 4.3 | 90.1 |
| Example 48 | 3.6 | 24.7 |
| Example 49 | 3.7 | 84.7 |

TABLE 1-continued $IC_{50}$ of Bcl-2 inhibition (fluorescence polarisation test) and of cytotoxicity for RS4;11 cells

| | $IC_{50}$ (nM) Bcl-2 FP | $IC_{50}$ (nM) MTT RS4;11 |
|---|---|---|
| Example 50 | 2.2 | 28.2 |
| Example 51 | 4.8 | 68.8 |
| Example 52 | 7.9 | 20.9 |
| Example 53 | 5.4 | 70.9 |
| Example 54 | 6.6 | 45 |
| Example 55 | 5.5 | 22.8 |
| Example 56 | 4.7 | 36.7 |
| Example 57 | 21.2 | 282 |
| Example 58 | 6.4 | 68.5 |
| Example 59 | 4.0 | 21.2 |
| Example 60 | 5.4 | 60.3 |
| Example 61 | 7.0 | 61.3 |
| Example 62 | 5.6 | 96.6 |
| Example 63 | 6.2 | 25.4 |
| Example 64 | 7.8 | 282 |
| Example 65 | 5.3 | 62.8 |
| Example 66 | 4.7 | 42 |
| Example 67 | ND | ND |
| Example 68 | 8.3 | 82.4 |
| Example 69 | 4.6 | 1.38 |
| Example 70 | 5.2 | 6.17 |
| Example 71 | 49 | ND |
| Example 72 | 90.2 | 1520 |
| Example 73 | 83.6 | 1320 |
| Example 74 | 68.7 | 1340 |
| Example 75 | 67.7 | 1360 |
| Example 76 | 77.6 | 1630 |
| Example 77 | 25.1% @ 10 µM | 1880 |
| Example 78 | 823.3 | 1880 |
| Example 79 | 99.1 | 1010 |
| Example 80 | 299.3 | 1880 |
| Example 81 | 12.1 | 778 |
| Example 82 | 42% @ 10 µM | 1880 |
| Example 83 | 35.8 | 1500 |
| Example 84 | 524.9 | ND |
| Example 85 | 242.7 | ND |
| Example 86 | 5 | 20.1 |

ND: not determined

For partial inhibitors, the percentage fluorescence polarisation inhibition for a given concentration of the test compound is indicated. Accordingly, 25.1% @10 µM means that 25.1% fluorescence polarisation inhibition is observed for a concentration of test compound equal to 10 µM.

EXAMPLE C

Induction of Caspase Activity In Vivo

The ability of the compounds of the invention to activate caspase 3 is evaluated in a xenograft model of RS4; 11 leukaemia cells.

$1 \times 10^7$ RS4;11 cells are grafted sub-cutaneously into immunosuppressed mice (SCID strain). 25 to 30 days after the graft, the animals are treated orally with the various compounds. Sixteen hours after treatment, the tumour masses are recovered and lysed, and the caspase 3 activity is measured in the tumour lysates.

This enzymatic measurement is carried out by assaying the appearance of a fluorigenic cleavage product (DEVDase activity, Promega). It is expressed in the form of an activation factor corresponding to the ratio between the two caspase activities:the activity for the treated mice divided by the activity for the control mice.

The results obtained show that the compounds of the invention are capable of inducing apoptosis in RS4; 11 tumour cells in vivo.

EXAMPLE D

Quantification of the Cleaved Form of Caspase 3 In Vivo

The ability of the compounds of the invention to activate caspase 3 is evaluated in a xenograft model of RS4; 11 leukaemia cells.

$1 \times 10^7$ RS4;11 cells are grafted sub-cutaneously into immunosuppressed mice (SCID strain). 25 to 30 days after the graft, the animals are treated orally with the various compounds. After treatment, the tumour masses are recovered (after a time period T) and lysed, and the cleaved (activated) form of caspase 3 is quantified in the tumour lysates.

The quantification is carried out using the "Meso Scale Discovery (MSD) ELISA platform" test, which specifically assays the cleaved form of caspase 3. It is expressed in the form of an activation factor corresponding to the ratio between the quantity of cleaved caspase 3 in the treated mice divided by the quantity of cleaved caspase 3 in the control mice.

The results show that the compounds of the invention are capable of inducing apoptosis in RS4;11 tumour cells in vivo.

TABLE 2

Caspase activation factors (cleaved caspase 3 MSD test in the tumours of treated mice versus control mice) in vivo, after treatment by the oral route (exact doses in brackets)

| Compound tested | Time period after which the tumour is removed (T) | Activation factor ± SEM (versus control) |
| --- | --- | --- |
| Example 2 | 6 hours | 14.6 (50 mg/kg) |
| Example 13 | 2 hours | 23.1 (50 mg/kg) |
| Example 17 | 2 hours | 15.3 (50 mg/kg) |
| Example 21 | 2 hours | 24.8 ± 1.4 (50 mg/kg) |
| Example 32 | 2 hours | 54.4 ± 2.8 (25 mg/kg) |
| Example 33 | 2 hours | 31.1 ± 10.8 (25 mg/kg) |
| Example 38 | 2 hours | 27.5 ± 2.6 (25 mg/kg) |
| Example 39 | 2 hours | 34.1 ± 2.4 (25 mg/kg) |
| Example 42 | 2 hours | 77.5 ± 4.8 (25 mg/kg) |
| Example 50 | 2 hours | 45.2 ± 3.9 (25 mg/kg) |
| Example 56 | 2 hours | 10.3 ± 4.2 (25 mg/kg) |

EXAMPLE E

Anti-Tumour Activity In Vivo

The anti-tumour activity of the compounds of the invention is evaluated in a xenograft model of RS4; 11 leukaemia cells.

$1 \times 10^7$ RS4;11 cells are grafted sub-cutaneously into immunosuppressed mice (SCID strain). 25 to 30 days after the graft, when the tumour mass has reached about 150 mm³, the mice are treated orally with the various compounds in two different regimes (daily treatment for five days per week for two weeks, or two treatments weekly for two weeks).

The tumour mass is measured twice weekly from the start of treatment.

The results obtained accordingly show that the compounds of the invention are capable of inducing significant tumour regression during the treatment period.

EXAMPLE F

Pharmaceutical Composition: Tablets

| | |
| --- | --- |
| 1000 tablets containing a dose of 5 mg of a compound selected from Examples 1 to 86 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:
1. A compound of formula (I):

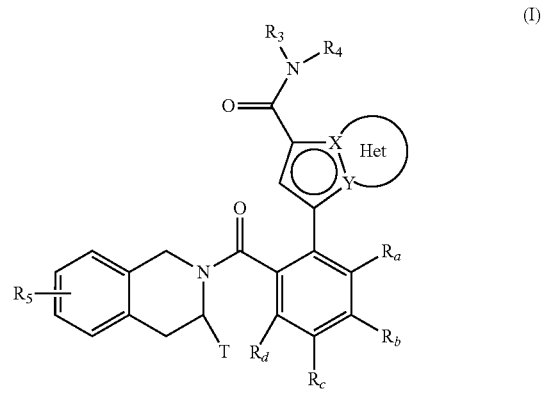

wherein:
X and Y represent a carbon atom or a nitrogen atom, it being understood that they may not simultaneously represent two carbons atoms or two nitrogen atoms;
the group

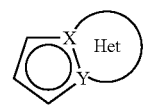

represents a group selected from 5,6,7,8-tetrahydroindolizine optionally substituted by an amino group; indolizine; 1,2,3,4-tetrahydropyrrolo[1,2-a]pyrazine optionally substituted by a methyl; and pyrrolo[1,2-a]pyrimidine;
T represents a hydrogen atom, a linear or branched $(C_1-C_6)$alkyl group optionally substituted by from one to three halogen atoms, a $(C_2-C_4)$alkyl-$NR_1R_2$ group, or a $(C_1-C_4)$alkyl-$OR_6$ group;
$R_1$ and $R_2$ independently of one another represent a hydrogen atom or a linear or branched $(C_1-C_6)$alkyl group,
or $R_1$ and $R_2$, together with the nitrogen atom carrying them, form a heterocycloalkyl;
$R_3$ represents a linear $(C_1-C_6)$alkyl, aryl or heteroaryl group, wherein the latter two groups can be substituted by from one to three groups selected from halogen, linear or branched $(C_1-C_6)$alkyl, linear or branched $(C_1-C_6)$alkoxy and cyano, wherein one or more of the carbon atoms of the preceding groups, or of their possible substituents, may be deuterated;

R$_4$ represents a 4-hydroxyphenyl group, wherein one or more of the carbon atoms of the preceding group may be deuterated;

R$_5$ represents a hydrogen or halogen atom, a linear or branched (C$_1$-C$_6$)alkyl group, or a linear or branched (C$_1$-C$_6$)alkoxy group;

R$_6$ represents a hydrogen atom or a linear or branched (C$_1$-C$_6$)alkyl group;

R$_a$ and R$_d$, each represent a hydrogen atom and (R$_b$, R$_c$), together with the carbon atoms carrying them, form a 1,3-dioxolane group or a 1,4-dioxane group; or R$_a$, R$_c$ and R$_d$ each represent a hydrogen atom and R$_b$ represents a hydrogen, a halogen, a methyl or a methoxy; or R$_a$, R$_b$ and R$_d$ each represent a hydrogen atom and R$_c$ represents a hydroxy or methoxy group;

wherein the aryl, heteroaryl, cycloalkyl and heterocycloalkyl groups so defined and the groups alkyl, alkenyl, alkynyl and alkoxy may be optionally substituted by from 1 to 3 groups selected from, linear or branched (C$_1$-C$_6$)alkyl, (C$_3$-C$_6$)spiro, linear or branched (C$_1$-C$_6$)alkoxy, (C$_1$-C$_6$) alkyl-S—, hydroxy, oxo (or N-oxide), nitro, cyano, —COOR', —OCOR', NR'R'', linear or branched (C$_1$-C$_6$) polyhaloalkyl, trifluoromethoxy, (C$_1$-C$_6$)alkylsulphonyl, halogen, optionally substituted aryl, heteroaryl, aryloxy, arylthio, cycloalkyl, heterocycloalkyl optionally substituted by one or more halogen atoms or alkyl groups, wherein R' and R'', each independently of the other, represent a hydrogen atom Or an optionally substituted, linear or branched (C$_1$-C$_6$)alkyl group, it being understood that:
"aryl" means a phenyl, naphthyl, biphenyl or indenyl group,
"heteroaryl" means any mono- or bi-cyclic group composed of from 5 to 10 ring members, having at least one aromatic moiety and containing from 1 to 4 hetero atoms selected from oxygen, sulphur and nitrogen (including quaternary nitrogens),
"cycloalkyl" means any mono- or bi-cyclic, non-aromatic, carbocyclic group containing from 3 to 10 ring members,
"heterocycloalkyl" means any mono- or bi-cyclic, non-aromatic, condensed or spiro group containing from 3 to 10 ring members and containing from 1 to 3 hetero atoms selected from oxygen, sulphur, SO, SO$_2$ and nitrogen, its enantiomers and diastereoisomers, and addition salts thereof with a pharmaceutically acceptable acid or base.

2. The compound according to claim 1, wherein T represents hydrogen, methyl, 2-(morpholin-4-yl)ethyl, 3-(morpholin-4-yl)propyl, —CH$_2$—H, 2-aminoethyl, 2-(3,3-difluoropiperidin-1-yl)ethyl, 2[(2,2-difluoroethyl)amino]ethyl or 2-(3-methoxyazetidin-1-yl)ethyl.

3. The compound according to claim 1, wherein R$_3$ represents a heteroaryl group selected front 1H-indole, 2,3-dihydro-1H-indole, 1H-indazole, pyridine, 1H-pyrrolo[2,3-b]pyridine, 1H-pyrazole, imidazo[1,2-a]pyridine, pyrazolo[1,5-a]pyrimidine, [1,2,4]triazolo[1,5-a]pyrimidine, and 1H-pyrazolo[3,4-b]pyridine, all of which may be optionally substituted by a linear or branched (C$_1$-C$_6$)alkyl group.

4. The compound according to claim 1, which is selected from:
N-(4-hydroxyphenyl)-3-(6-{[(3R)-3-methyl-3,4-dihydroisoquinolin-2(1H)-yl]-carbonyl}-1,3-benzodioxol-5-yl)-N-{1-[2-(morpholin-4-yl)ethyl]-1H-indol-5-yl}-5,6,7,8-tetrahydroindolizine-1-carboxamide,
N-(4-hydroxyphenyl)-3-(6-{[(3S)-3-[2-(morpholin-4-yl)ethyl]-3,4-dihydroisoquinolin-2(1H)-yl]carbonyl}-1,3-benzodioxol-5-yl)-N-phenyl-5,6,7,8-tetrahydroindolizine-1-carboxamide,
N-{3-fluoro-4-[2-(morpholin-4-yl)ethoxy]phenyl}-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide,
N-(4-hydroxyphenyl)-3-(6-{[(3R)-3-methyl-3,4-dihydroisoquinolin-2(1H)-yl]-carbonyl}-1,3-benzodioxol-5-yl)-N-(pyridin-4-yl)indolizine-1-carboxamide,
N-(4-hydroxyphenyl)-3-(6-{[(3R)-3-methyl-3,4-dihydroisoquinolin-2(1H)-yl]-carbonyl}-1,3-benzodioxol-5-yl)-N-(2-methylpyridin-4-yl)indolizine-1-carboxamide,
N-(4-hydroxyphenyl)-3-(6-{[(3R)-3-methyl-3,4-dihydroisoquinolin-2(1H)-yl]-carbonyl}-1,3-benzodioxol-5-yl)-N-(1-methyl-1H-pyrrolo[2,3-b]pyridin-5-yl)-indolizine-1-carboxamide,
N-(4-hydroxyphenyl)-3-(6-{[(3R)-3-[3-(morpholin-4-yl)propyl]-3,4-dihydroisoquinolin-2(1H)-yl]carbonyl}-1,3-benzodioxol-5-yl)-N-phenyl-5,6,7,8-tetrahydroindolizine-1-carboxamide,
N-(2,6-dimethylpyridin-4-yl)-N-(4-hydroxyphenyl)-3-(6-{[(3R)-3-methyl-3,4-dihydroisoquinolin-2(1H)-yl]carbonyl}-1,3-benzodioxol-5-yl)indolizine-1-carboxamide,
N-(4-hydroxyphenyl)-3-(6-{[(3R)-3-methyl-3,4-dihydroisoquinolin-2(1H)-yl]-carbonyl}-1,3-benzodioxol-5-yl)-N-(pyridin-4-yl)-5,6,7,8-tetrahydroindolizine-1-carboxamide,
3-(5-chloro-2-{[(3R)-3-methyl-3,4-dihydroisoquinolin-2(1H)-yl]carbonyl}phenyl)-N-(4-hydroxyphenyl)-N-(1-methyl-1H-pyrrolo[2,3-b]pyridin-5-yl)indolizine-1-carboxamide,
N-(4-hydroxyphenyl)-N-(2-methoxypyridin-4-yl)-3-(6-{[(3R)-3-methyl-3,4-dihydroisoquinolin-2(1H)-yl]carbonyl}-1,3-benzodioxol-5-yl)indolizine-1-carboxamide, and their enantiomers and diastereoisomers, and addition salts thereof with a pharmaceutically acceptable acid or base.

5. A pharmaceutical composition comprising the compound according to claim 1, in combination with one or more pharmaceutically acceptable excipients.

* * * * *

UNITED STATES PATENT AND TRADEMARK OFFICE
CERTIFICATE OF CORRECTION

PATENT NO. : 9,944,620 B2  Page 1 of 1
APPLICATION NO. : 14/906330
DATED : April 17, 2018
INVENTOR(S) : Arnaud Le Tiran et al.

It is certified that error appears in the above-identified patent and that said Letters Patent is hereby corrected as shown below:

On the Title Page

Column 1, under Inventors, Line 2; "Sanit" should read -- Saint --

Column 1, under Inventors, Line 3; "Jérôme" should read -- Jérôme --

Column 1, under Assignees, Line 3; delete "Berkshire"

Column 1, Page 2, under FOREIGN PATENT DOCUMENTS, Line 4; "WO 2009/102488" should read -- WO 2009/102468 --

Column 1, Page 2, under FOREIGN PATENT DOCUMENTS, Line 10; "WO 2013/098049" should read -- WO 2013/096049 --

In the Claims

Column 63, Line 28; "Or" should read -- or --

Column 63, Line 50; "-$CH_2$-H," should read -- "-$CH_2$-OH, --

Column 63, Line 51; "2[" should read -- 2-[ --

Column 63, Line 54; "front" should read -- from: --

Signed and Sealed this
Twenty-sixth Day of June, 2018

Andrei Iancu
*Director of the United States Patent and Trademark Office*